United States Patent [19]
Saika et al.

[11] Patent Number: 5,780,498
[45] Date of Patent: Jul. 14, 1998

[54] ENDOTHELIN RECEPTOR ANTAGONISTS

[75] Inventors: Hideyuki Saika, Kobe; Toshiki Murata, Ikoma, both of Japan; Thomas Pitterna, Basel; Thomas Früh, Magden, both of Switzerland; Lene D. Svensson, Hellerup, Denmark; Yoshihiro Urade, Nakagyo-ku, Japan; Takaki Yamamura, Nishinomiya, Japan; Toshikazu Okada, Takarazuka, Japan

[73] Assignee: Ciba-Geigy Japan Limited, Hyogo-ken, Japan

[21] Appl. No.: 637,720

[22] PCT Filed: Oct. 17, 1994

[86] PCT No.: PCT/EP94/03418

§ 371 Date: Apr. 30, 1996

§ 102(e) Date: Apr. 30, 1996

[87] PCT Pub. No.: WO95/12611

PCT Pub. Date: May 11, 1995

[30] Foreign Application Priority Data

Nov. 1, 1993 [EP] European Pat. Off. ............. 93810760

[51] Int. Cl.$^6$ .................. A61K 31/40; A61K 31/47; A61K 31/44; C07D 401/12; C07D 215/38; C07D 209/12; C07D 333/02; C07C 233/00

[52] U.S. Cl. .................. 514/419; 514/75; 514/80; 514/309; 514/314; 514/337; 514/378; 514/381; 514/385; 514/418; 514/443; 514/616; 546/22; 546/141; 546/175; 546/277.4; 548/112; 548/247; 548/253; 548/312.1; 548/413; 548/485; 548/486; 548/492; 548/494; 548/495; 549/6; 549/57; 549/58; 564/15; 564/155

[58] Field of Search .................. 546/277.4, 175, 546/141, 22; 548/495, 312.1, 253, 247, 112, 413, 485, 486, 494, 492; 549/58, 57, 6; 564/155; 514/616, 443, 419, 385, 381, 378, 337, 314, 309, 75, 80, 418

[56] References Cited

FOREIGN PATENT DOCUMENTS

| | | |
|---|---|---|
| 0 013 891 | 8/1980 | European Pat. Off. |
| 0 337 774 | 10/1980 | European Pat. Off. |
| 0 074 787 | 3/1983 | European Pat. Off. |
| 0 212 550 | 3/1987 | European Pat. Off. |
| 217 286 | 4/1987 | European Pat. Off. |
| 237 082 | 9/1987 | European Pat. Off. |
| 0 333 174 | 9/1989 | European Pat. Off. |
| 0 405 421 | 1/1991 | European Pat. Off. |
| 0 436 189 | 7/1991 | European Pat. Off. |
| 0 457 195 | 11/1991 | European Pat. Off. |
| 0 460 679 | 12/1991 | European Pat. Off. |
| 0 510 526 | 10/1992 | European Pat. Off. |
| 0 526 708 | 2/1993 | European Pat. Off. |
| 0 558 258 | 9/1993 | European Pat. Off. |
| 0 562 599 | 9/1993 | European Pat. Off. |
| 0 569 193 | 11/1993 | European Pat. Off. |
| 2 294 694 | 7/1976 | France |
| 3 332 633 | 4/1985 | Germany |
| WO 92/05271 | 4/1992 | WIPO |
| WO92/19254 | 11/1992 | WIPO |
| WO92/20706 | 11/1992 | WIPO |
| WO93/08799 | 5/1993 | WIPO |
| WO 94/02474 | 2/1994 | WIPO |

OTHER PUBLICATIONS

Breu et al., Third International Conference on Endothelin, Feb. 15–17, 1993, pp. 11 and 17.

Doherty et al., Journal of Medicinal Chemistry, vol. 36, No. 18, pp. 2585–2594 (1993).

Steinke et al., Formation of Peptide Bonds by Carboxypeptidase c from Orange Leaves, Enzyme Microbial Technology, vol. 13, No. 3, pp. 262–266, Mar. 1991.

Imai et al., Photoaffinity Heterobifunctional Cross–Linking Reagents Based on N–(Azidobenzoyl)tyrosines, Bioconjugate Chemistry, vol. 1, No. 2, pp. 138–143, Mar. 1990.

*Primary Examiner*—Mukund J. Shah
*Assistant Examiner*—Brenda Coleman
*Attorney, Agent, or Firm*—Wenderoth, Lind & Ponack

[57] ABSTRACT

The present invention provides novel compounds represented by the general formula I:

$$R_1-\overset{O}{\overset{\|}{C}}-\underset{R_2}{\overset{}{N}}-CH-\overset{X}{\overset{\|}{C}}-Y-\underset{R_4}{\overset{}{CH}}-R_5 \quad (I)$$
$$\underset{R_3}{\overset{}{|}}$$
$$R_3''-C-R_3'$$

wherein $R_1$ is a straight or branched lower alkyl, a cycloalkyl-lower alkyl, an aryl-lower alkyl, a cycloalkyl, an aryl an aryl-cycloalkyl, lower alkoxy, an aryloxy, or a heteroaryl;

$R_2$ is hydrogen, a straight or branched lower alkyl, a cycloalkyl, or a cycloalkyl-lower alkyl;

$R_3$ and $R_3'$ are each the same or different and each is hydrogen atom, a straight or branched lower alkyl, a cycloalkyl, an aryl-lower alkyl, an aryl, or a heteroaryl; or $R_3$ and $R_3'$ together form a ring structure;

$R_3''$ is hydrogen, lower alkyl or an aryl; or $R_2$ and $R_3''$ together form a lower alkylene group —$(CH_2)_n$— wherein n is an integer of 1, 2 or 3; or $R_2$ and $R_3''$ together form a group represented by the formula: —$(CH_2)_p$—Ar— or —Ar—$(CH_2)_p$—, respectively, wherein p is zero or an integer of 1 or 2, and Ar is an arylene or heteroarylene;

$C(=X)$ is $C(=O)$, $C(=S)$, $C(=NH)$, $C(=N$-lower alkyl); $C=NH$—OH, or $CH_2$;

Y is a direct bond, —NH—, a lower alkyl-N<, an oxygen atom, or methylene; or $C(=X)$ is CHOH and Y is a direct bond or methylene;

$R_4$ is —$(CH_2)_s$—Ar' wherein s is zero or an integer of 1, 2 or 3; and Ar' is an aryl, or a heteroaryl; and $R_5$ is carboxy, substituted or unsubstituted carboxamide, $PO(OH)_2$, tetrazole, $CH_2OH$, CN, or hydrogen;
and salts thereof.

15 Claims, No Drawings

ENDOTHELIN RECEPTOR ANTAGONISTS

This application is a 371 of PCT/EP94/03418 filed Oct. 17, 1994.

BACKGROUND OF THE INVENTION

1. Field of the Invention

The present invention relates to novel compounds as antagonists of endothelin (ET) receptors, processes for their preparation, their use and pharmaceutical compositions.

2. Description of Related Art

ETs are a family of vasoactive peptides with 21 amino acid residues and two intramolecular disulfide bonds. They comprise ET-1, the original ET isolated from the culture media of porcine endothelial cells, ET-2 and ET-3.

ETs, of which biosynthesis is enhanced by many biological and pathological factors, are widely distributed in both peripheral and brain tissues of mammalians, and elicit a number of biological responses by binding to at least two distinct ET receptor subtypes, $ET_A$ and $ET_B$ receptors.

ET receptors are present in cardiovascular, renal, hepatic and neural tissues. ET receptors are also found in the respiratory, gastrointestinal, endocrine, central nervous and genito-urinary systems, the blood and blood forming organs, the sensory organs, and other tissues in the body.

ETs are the most potent and longest acting endogeneous constrictors of blood vessels identified to date. ETs also cause contraction of various non-vascular smooth muscles including the air-way, and the cardiac muscle. In addition, ETs are ulcerogenic and pro-intlammatory. ETs have regulatory functions on hormone- or peptide-secretion, neurotransmission, ion-transport and metabolism.

EP 436189A describes endothelin antagonistic cyclic pentapeptides. EP 457195A describes endothelin antagonistic oligopeptides comprising L-leucine and D-tryptophan. They could not be orally administered. EP 460679A describes endothelin antagonistic peptide derivatives, specifically tripeptides are disclosed. WO 92/20706 describes endothelin antagonists, specifically hexapeptides are disclosed. EP 526708 describes endothelin antagonistic benzosulfonamide derivatives. EP 510526A also describes endothelin antagonistic benzosulfonamide derivatives. Although the benzosulfonamide derivatives can be administered orally, their antagonistic activity is not high. In EP 13891A dipeptide derivatives of phenylalanine and trypthophan are disclosed having tumor tissue destroying properties. FR 2294694 describes phenylalanylphenylalanyl derivatives having anti-ulcer effects.

SUMMARY OF THE INVENTION

The present invention provides novel compounds represented by the general formula I:

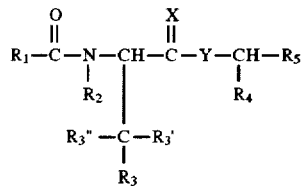

wherein $R_1$ is a straight or branched lower alkyl, a cycloalkyl-lower alkyl, an aryl-lower alkyl, a cycloalkyl, an aryl, an aryl-cycloalkyl, lower alkoxy, an aryloxy, or a heteroaryl;

$R_2$ is hydrogen, a straight or branched lower alkyl, a cycloalkyl, or a cycloalkyl-lower alkyl;

$R_3$ and $R_3'$ are each the same or different and each is hydrogen, a straight or branched lower alkyl, a cycloalkyl, an aryl-lower alkyl, an aryl, or a heteroaryl; or $R_3$ and $R_3'$ together form a ring structure;

$R_3''$ is hydrogen, lower alkyl or an aryl; or $R_2$ and $R_3''$ together form a lower alkylene group —(CH$_2$)$_n$— wherein n is an integer of 1, 2 or 3; or $R_2$ and $R_3''$ together form a group represented by the formula: —(CH$_2$)$_p$—Ar— or —Ar—(CH$_2$)$_p$—, respectively, wherein p is zero or an integer of 1 or 2, and Ar is an arylene or heteroarylene;

C(=X) is C(=O), C(=S), C(=NH), C(=N-lower alkyl); C=NH—OH, or CH$_2$;

Y is a direct bond, —NH—, a lower alkyl-N<, an oxygen atom, or methylene; or

C(=X) is CHOH and Y is a direct bond or methylene;

$R_4$ is —(CH$_2$)$_s$—Ar' wherein s is zero or an integer of 1, 2 or 3; and Ar' is an aryl, or a heteroaryl; and $R_5$ is carboxy, substituted or unsubstituted carboxamide, PO(OH)$_2$, tetrazole, CH$_2$OH, CN, or hydrogen;

and salts thereof;

with the proviso that, when $R_1$ is phenyl or phenyl substituted by lower alkoxy; $R_3$ is phenyl; $R_3'$ and $R_3''$ each are hydrogen; X is oxygen; Y is NH; $R_4$ is 4-hydroxybenzyl; $R_5$ is carboxy; $R_2$ is different from hydrogen; and with the further proviso that, when $R_1$ is lower alkyl; $R_3$ is phenyl; $R_3'$ and $R_3''$ each are hydrogen; X is oxygen; Y is NH; $R_4$ is indol-3-ylmethyl; $R_5$ is carboxy; carbamoyl, or carbamoyl which is mono- or di-substituted by lower alkyl; $R_2$ is different from hydrogen; or a pharmaceutically acceptable salt thereof.

All of the compounds of the present invention possess two or more chiral centers and each center may exist e.g. in the R(D), S(L), S,R and/or S,S configuration. The present invention includes all essentially pure enantiomeric and diastereomeric forms as well as appropriate mixtures of corresponding enantiomers and diastereomers, e.g. racemates. Preferred are those compounds of formula I, in which Y is different from CH$_2$ and the carbon atom, to which the structural element —C(R$_3$)(R$_3'$)(R$_3''$) is attached, has the D(R) configuration and in which the carbon atom, to which the variable R$_4$ is attached, has the L(S) configuration.

The term "aryl" represents for example carbocyclic aryl and includes phenyl, biphenylyl such as 2-, 3- or especially 4-biphenylyl, and naphthyl, such as 2-naphthyl or 3-naphthyl. The aryl may be unsubstituted, or mono- or poly-, for example, di- or tri-substituted. The substituents are selected from the group consisting of, for example, halogen such as fluorine, chlorine, bromine or iodine, a lower alkyl such as methyl or ethyl, a lower alkoxy such as methoxy or ethoxy, substituted lower alkyl such as halo-lower alkyl, for example, trifluoromethyl, hydroxy, aryl-substituted lower alkoxy such as a phenyl-lower alkoxy, for example, benzyloxy, carboxy, lower alkoxycarbonyl, amino, cyano, cyano-lower alkanoyl such as cyanoacetyl, and nitro. Where the aryl, such as phenyl, is polysubstituted, the substituents may be different or same. Aryl preferably is unsubstituted or substituted phenyl or biphenylyl, especially 4-biphenylyl, respectively.

The term "heteroaryl" represents, for example, mono- or bicyclic heteroaryl having up to and including 4 identical or different hetero atoms such as nitrogen, oxygen or sulfur, preferably one, two, three, or four nitrogen atoms, a nitrogen and an oxygen or a sulfur, an oxygen or a sulfur atom. Preferred are corresponding 5- or 6-membered monocyclic heteroaryl radicals which may also be attached to a carbocyclic aryl radical, especially phenyl. Appropriate monocyclic 5-membered heteroaryl radicals are, for example, monoaza-, diaza-, triaza-, tetraaza-, monooxa-, monothia-, oxaza- or thiaza-cyclic aryl radicals, whereas an appropriate monocyclic 6-membered radicals is in particular an azaaryl or an oxaaryl radical such as pyridyl or pyranyl. A corresponding monocyclic heteroaryl radical includes, for example, thienyl such as 2-thienyl or 3-thienyl, furanyl such as 2-furanyl or 3-furanyl, pyrrolyl such as 2- or 3-pyrrolyl, triazolyl such as 1,3,5-1H-triazol-2-yl or 1,3,4-triazol-2-yl, tetrazolyl such as 1H-tretrazol-5-yl, imidazolyl such as 1-, 2-, 4- or 5-imidazolyl, oxazolyl such as 2-, 4- or 5 oxazolyl, isoxazolyl such as 3-, 4- or 5-isoxazolyl, thiazolyl such as 2-, 4- or 5-thiazolyl, isothiazolyl such as 3-, 4- or 5-isothiazolyl, pyridyl such as 2-pyridyl, 3-pyridyl, 4-pyridyl, or pyranyl such as 2-pyranyl or 3-pyranyl. Especially preferred are 5- or 6-membered monocyclic heteroaryl radicals which are attached to a carbocyclic radical and comprise, for example, pyridyl-phenyl such as 4-(2-pyridyl)-phenyl, thienyl-phenyl, such as 2-thienyl-4-phenyl or 3-thienyl-4-phenyl, furyl-phenyl such as 2-furyl-4-phenyl or 3-furyl-4-phenyl, pyrrolylphenyl such as 1-, 2- or 3-pyrrolyl-4-phenyl, imidazolyl-phenyl such as 1-, 3- or 5-imidazolyl-4-phenyl, oxazolylphenyl such as 2-, 4- or 5-oxazolyl-4-phenyl, isoxazolyl-phenyl such as 5-isoxazolyl-4-phenyl, thiazolyl-phenyl such as 2-, 4- or 5-thiazolyl-phenyl, isothiazolyl-phenyl such as 3-, 4- or 5-isothiazolyl-phenyl, triazolyl-phenyl such as 1,3,5-1H-triazol-2-yl-4-phenyl or 1,3,4-triazol-2-yl-4-phenyl, tetrazolyl-phenyl such 5-1H-tetrazolyl-4-phenyl. Preferred is corresponding 4-(heteroaryl)-phenyl. Bicyclic heteroaryl represents, for example, a benzo-fused 5- or 6-membered heteroarylradical. A corresponding radical includes, for example, indolyl such as 2- or especially 3-indolyl, 1-lower alkyl-indolyl such as 1-methyl-3-indolyl, benzothiophenyl such as 2- or especially 3-benzothiophenyl, benzofuranyl such as 2- or 3-benzofuranyl, quinolinyl such 2-, 3- or especially 4-quinolinyl, and isoquinolinyl such as 1-, 3- or 4-isoquinolinyl. The heteroaryl group may be unsubstituted, or mono- or poly-, for example di- or tri-substituted. The substituents for the heteroaryl group are, for example, those described for the aryl group above. The substituted heteroaryl is, for example, 3-methyl-2-thienyl, and 5-methyl-2-thienyl.

The ring structure formed by $R_3$ and $R_3'$ is fluorenyl such as 9-fluorenyl, anthryl such as 9-anthryl, or preferably dibenzosuberyl such as 5-dibenzosuberyl.

In the aryl-lower alkyl, the aryl moiety has the same meaning as described for the aryl; and the lower alkyl moiety has the same meaning as described for the lower alkyl. Aryl preferably is unsubstituted or furthermore substituted phenyl.

In the aryl-cycloalkyl, the aryl moiety has the same meaning as described for the aryl group; and the cycloalkyl moiety has the same meaning as described for the cycloalkyl group. The aryl-cycloalkyl is, for example, phenyl-cyclopropyl. Aryl preferably is unsubstituted or furthermore substituted phenyl.

In the aryloxy, the aryl moiety has the same meaning as described for the aryl group. Aryl preferably is unsubstituted or furthermore substituted phenyl.

Where $R_2$ and $R_3''$ together form a group represented by the formula: —(CH$_2$)$_p$—Ar—, the Ar is an arylene or a heteroarylene. The preferred arylene is, for example, 1,2-phenylene, whereas preferred heteroarylene is, for example, 2,3-pyridylene.

The aryl for Ar' of $R_4$ is, for example, phenyl, naphthyl such as 1-naphthyl or 2-naphthyl, or biphenylyl such as 2- or preferably 4-biphenylyl.

The heteroaryl for Ar' of $R_4$ is for example, pydridyl such as 4-pyridyl, thienyl such as 2-thienyl, indolyl such as 3-indolyl, or 1-lower alkyl-indolyl such as 1-methyl-3-indolyl.

The aryl and heteroaryl for Ar' may be unsubstituted, or substituted. The substituent for Ar' is for example, a lower alkyl such as methyl.

The substituted or unsubstituted amide group for $R_5$ is, for example, —CONH$_2$ or —CONHOH.

Especially preferred are compounds of formula I or pharmaceutically acceptable salts thereof, wherein, independently of one another, $R_1$ is 3,5-di-$C_1$–$C_4$-alkyl-dibenzoyl such as 3,5-dimethyl-benzoyl;

$R_2$ is $C_1$–$C_4$-alkyl;

$R_3$ is 4-biphenylyl, thienyl-4-phenyl such as 2-thienyl-4-phenyl or 3-thienyl-4-phenyl, or isoxazolyl-4-phenyl such as 4-(3-isoxazolyl)-phenyl or 4-(5-isoxazolyl)-phenyl;

$R_3'$ and $R_3''$ each are hydrogen;

$R_4$ is 3-indolylmethyl;

$R_5$ is carboxy;

$C(=X)$ is $C(=O)$;

Y is NH.

The compounds represented by the formula (I) are capable of forming pharmaceutically acceptable acid addition salts and/or base addition salts. Pharmaceutically acceptable acid addition salts of the compound (I) include those of inorganic acids, for example, hydrohalic acid such as hydrofluoric acid, hydrochloric acid, hydrodromic acid or hydroiodic acid, nitric acid, sulfuric acid, phosphoric acid; organic acids such as formic acid, acetic acid, propionic acid, butylic acid, hydroxy acid such as lactic acid, citric acid or malic acid, dicarboxylic acid such as maleic acid or succinic acid, sulfonic acid such as methanesulfonic acid or benzenesulfonic acid.

Salts of the present compounds (I) with bases are, for example, those with bases, for example, inorganic bases such as ammonium hydroxide or metal hydroxide, such as lithium hydroxide, such as alkaline metal hydroxide such as sodium hydroxide, potassium hydroxide, alkaline earth metal hydroxide, such as calcium hydroxide; or those with organic bases, for example, amines, for example, mono-, di- or tri-lower alkylamines, such as mono-, di- or tri-methylamine or -ethyl-amine.

The general definitions used above and below, unless defined differently, have the following meanings:

The expression "lower" means that corresponding groups and compounds in each case in particular comprise not more than 7, preferably not more than 4, carbon atoms.

The term "lower alkyl" means an alkyl having 1 up to and including 7 carbon atoms, preferably 1 up to and including 4 carbon atoms, and for example, is methyl, ethyl, n-propyl, isopropyl, n-butyl, isobutyl, tert-butyl, straight or branched pentyl, straight or branched hexyl, or straight or branched heptyl. Preferred is $C_1$–$C_4$alkyl.

The "cycloalkyl" has preferably 3 up to and including 8 carbon atoms, and is cyclopropyl, cyclobutyl, cyclopentyl, cyclohexyl, cyclopentyl, or cycloheptyl, or cyclooctyl. The cycloalkyl is preferably a cyclohexyl. The cycloalkyl may be substituted. Substituent for the cyclohexyl is, for example, a lower alkyl such as methyl or ethyl.

In the "cycloalkyl-lower alkyl", the cycloalkyl moiety has the same meanings as described above for the cycloalkyl;

and the lower alkyl moiety has the same meaning as described for the lower alkyl.

Substituted lower alkyl is, for example, halo-lower alkyl.

The substituted phenyl is, for example, 3-methylphenyl, 4-methylphenyl, 3,5-dimethylphenyl, 3,5-difluorophenyl, 3,5-dichlorophenyl, 3,5-dibromophenyl, 3,5-ditrifluoromethyl-phenyl, 3,5-dihydroxyphenyl, 2,5-dihydroxyphenyl, 2-, 3- or 4-methoxyphenyl, 3,5-dimethoxyphenyl, 3,5-dinitrophenyl.

In the definition for $R_2$, $R_3$ and $R_3'$ lower alkyl, cycloalkyl, cycloalkyl-lower alkyl, aryl and heteroaryl have the same meanings as defined for corresponding substituent groups for $R_1$. In addition, the aryl includes a phenyl-lower alkoxy-phenyl-lower alkyl.

Tetrazole is especially 1H-tetrazol-5-yl.

Lower alkylene is, for example, $C_1$–$C_7$alkylene, and is straight-chain or branched and is in particular methylene, ethylene, propylene and butylene and also 1,2-propylene, 2-methyl-1,3-propylene and 2,2-dimethyl-1,3-propylene. $C_1$–$C_5$alkylene is preferred.

Lower alkoxy is in particular $C_1$–$C_7$alkoxy and is, for example, methoxy, ethoxy, n-propyloxy, isopropyloxy, n-butyloxy, isobutyloxy, sec-butyloxy, tert-butyloxy and also includes corresponding pentyloxy, hexyloxy and heptyloxy radicals. $C_1$–$C_4$alkoxy is preferred.

Phenyl-lower alkoxy is in particular phenyl-$C_1$–$C_4$alkoxy, such as benzyloxy, 1- or 2-phenylethoxy, 3-phenylpropyloxy or 4-phenylbutyloxy.

Halogen is in particular halogen of atomic number not more than 35, such as fluorine, chlorine or bromine, and also includes iodine.

Halo-lower alkyl is in particular halo-$C_1$–$C_4$alkyl, such as trifluoromethyl, 1,1,2-trifluoro-2-chloroethyl or chloromethyl.

Lower alkoxycarbonyl is in particular $C_2$–$C_8$alkoxycarbonyl and is, for example, methoxy-, ethoxy-, propyloxy- or pivaloyloxy-carbonyl. $C_2$–$C_5$alkoxycarbonyl is preferred.

Cyano-lower alkanoyl is in particular ω-cyano-$C_2$–$C_5$-alkanoyl and is, for example, cyano-acetyl, 3-cyano-propionyl or 4-cyano-butyryl.

Extensive pharmacological investigations have shown that the compounds I and their pharmaceutically acceptable salts, for example, have pronounced pharmaceutical, for example, endothelin receptor antagonistic, properties and a beneficial pharmacological profile. The compounds of the present invention bind to both the $ET_A$ and $ET_B$ receptors. Compared to prior art endothelin receptor antagonists, the compounds according to the present invention comprise at most two peptidic bonds. Furthermore, they are distinguished from prior art compounds not only by their unexpected and favorable stability.

The ET receptor antagonists of the present invention are useful for various human diseases caused by ETs, either directly or in concert with other factors. In particular, they are useful for various cardiovascular diseases such as cerebral and coronary vasospasm, cerebral and coronary ischemia, subarachnoidal haemorrhage, various types of hypertension, pulmonary hypertention, cardiac failure, Raynand-syndrome, diabetes, atherosclerosis or restenosis due to denudation following angioplasty.

The compounds of the present invention also provide a new therapeutic potential for asthma, renal failure, dialysis, glomerular injury, hepatic failure, stomach and duodenal ulcer, ulcus cruris, various brain dysfunctions including migraine, benign prostatic hyperplasia, and occular diseases, glaucoma in particular.

They are also useful to overcome the adverse effects of cyclosporin and can be used for endotoxin shock, or disseminated intravascular coagulation.

The compounds of the formula I and their pharmaceutically acceptable salts can therefore be used, for example, as pharmaceutical active ingredients which are employed, for example, for the treatment of various cardiovascular diseases such as cerebral and coronary vasospasm, cerebral and coronary ischemia, subarachnoidal haemorrhage, various types of hypertension, pulmonary hypertention, cardiac failure, Raynand-syndrome, diabetes, atherosclerosis or restenosis due to denudation following angioplasty and also for the treatment of asthma, renal failure, dialysis, glomerular injury, hepatic failure, stomach and duodenal ulcer, ulcus cruris, various brain dysfunctions including migraine, benign prostatic hyperplasia, and occular diseases, glaucoma in particular. The invention thus relates to the use of the compounds according to the invention and their pharmaceutically acceptable salts for the production of appropriate medicaments and to the therapeutic treatment of various cardiovascular diseases such as cerebral and coronary vasospasm, cerebral and coronary ischemia, subarachnoidal haemorrhage, various types of hypertension, pulmonary hypertention, cardiac failure, Raynand-syndrome, diabetes, atherosclerosis or restenosis due to denudation following angioplasty also for the treatment of asthma, renal failure, dialysis, glomerular injury, hepatic failure, stomach and duodenal ulcer, ulcus cruris, various brain dysfunctions including migraine, benign prostatic hyperplasia, and occular diseases, glaucoma in particular. The industrial production of the active substances is also included in the production of the pharmaceuticals.

Furthermore, the compounds of the present invention can be used as research tools, e.g. for determining lead compounds which have an excellent binding profile to both the $ET_A$ and $ET_B$ receptors.

The invention relates especially to a compound of formula I wherein $R_1$ is a cycloalkyl, an aryl, an aryl-cycloalkyl, lower alkoxy, an aryloxy, or an heteroaryl; $R_2$, $R_3$, $R_3'$, $R_3''$, $R_4$, $R_5$, $C(=X)$, and Y have the meanings given above; or a salt thereof.

The invention relates to a compound of formula I wherein $R_1$ is a straight of branched lower alkyl, a cycloalkyl-lower alkyl, an aryl-lower alkyl, a cycloalkyl, an aryl, an aryl-cycloalkyl, lower alkoxy, an aryloxy, or a heteroaryl;

$R_2$ is hydrogen, a straight or branched lower alkyl, a cycloalkyl, or a cycloalkyl-lower alkyl;

$R_3$ is hydrogen atom, a straight or branched lower alkyl, a cycloalkyl, an aryl-lower alkyl, an aryl, or a heteroaryl;

$R_3'$ is cycloalkyl, an aryl-lower alkyl, an aryl, or a heteroaryl; or $R_3$ and $R_3'$ together form a ring structure.

$R_3''$ is hydrogen, lower alkyl or an aryl; or $R_2$ and $R_3''$ together form a lower alkylene group —$(CH_2)_n$— wherein n is an integer of 1, 2 or 3; or $R_2$ and $R_3''$ together form a group represented by the formula: —$(CH_2)_p$—Ar— or —Ar—$(CH_2)_p$—, respectively, wherein p is zero or an integer of 1 or 2, and Ar is an arylene or heteroarylene;

$C(=X)$ is $C(=O)$, $C(=S)$, $C(=NH)$, $C(=N$-lower alkyl); C=NH—OH, or $CH_2$;

Y is a direct bond, —NH—, a lower alkyl-N<, an oxygen atom, or methylene; or $C(=X)$ is CHOH; and Y is a direct bond or methylene;

$R_4$ is —$(CH_2)_s$—Ar' wherein s is zero or an integer of 1, 2 or 3; and Ar' is an aryl or a heteroaryl; and $R_5$ is carboxy, substituted or unsubstituted carboxamide, $PO(OH)_2$, tetrazole, $CH_2OH$, CN, or hydrogen;

or a salt thereof.

The invention relates especially to a compound of formula I wherein $R_1$ is lower alkyl, $C_3$–$C_8$-cycloalkyl-lower alkyl, aryl-lower alkyl in which aryl represents phenyl, biphenylyl or naphthyl, $C_3$–$C_8$-cycloalkyl, aryl being phenyl, biphenylyl or naphthyl, aryl-$C_3$–$C_8$-cycloalkyl in which aryl represents phenyl, biphenylyl or naphthyl, lower alkoxy, aryloxy in which aryl represents phenyl, biphenylyl or naphthyl, or heteroaryl in which heteroaryl represents a 5- or 6-membered monocyclic heteroaryl radical having up to and including 4 identical or different hetero atoms selected from nitrogen, oxygen or sulfur, which radicals may also be attached to a carbocyclic aryl radical, or in which heteroaryl represents a bicyclic heteroaryl radical having up to and including 4 identical or different hetero atoms selected from nitrogen, oxygen or sulfur; $R_2$ is a hydrogen atom, lower alkyl, $C_3$–$C_8$-cycloalkyl, $C_3$–$C_8$-cycloalkyl-lower alkyl; $R_3$ and $R_3'$ are each the same or different and each is hydrogen, lower alkyl, $C_3$–$C_8$-cycloalkyl, aryl-lower alkyl in which aryl represents phenyl, biphenylyl or naphthyl, aryl being phenyl, biphenylyl or naphthyl, or heteroaryl in which heteroaryl represents a 5- or 6-membered monocyclic heteroaryl radical having up to and including 4 identical or different hetero atoms selected from nitrogen, oxygen or sulfur, which radicals may also be attached to a carbocyclic aryl radical, or in which heteroaryl represents a bicyclic heteroaryl radical having up to and including 4 identical or different hetero atoms selected from nitrogen, oxygen or sulfur; or $R_3$ and $R_3'$ together form fluorenyl, anthryl, or dibenzosuberyl;

$R_3"$ is hydrogen, lower alkyl or aryl being phenyl, biphenylyl or naphthyl; or $R_2$ and $R_3"$ together form a lower alkylene group —$(CH_2)_n$— wherein n is an integer of 1, 2 or 3; or $R_2$ and $R_3"$ together form a group represented by formula: —$(CH_2)_p$—Ar— or —Ar—$(CH_2)_p$—, respectively, wherein p is zero or an integer of 1 or 2, and Ar is a phenylene or pyridylene;

C(=X) is C(=O), C(=S), C(=NH), C(=N-lower alkyl); C=NH—OH, or $CH_2$;

Y is a direct bond, —NH—, a lower alkyl-N<, oxygen, or methylene; or C(=X) is CHOH and Y is a direct bond or methylene;

$R_4$ is —$(CH_2)_s$—Ar' wherein s is zero or an integer of 1, 2 or 3; and Ar' is an aryl which represents phenyl, biphenylyl or naphthyl, or heteroaryl in which heteroaryl represents a 5- or 6-membered monocyclic heteroaryl radical having up to and including 4 identical or different hetero atoms selected from nitrogen, oxygen or sulfur, which radicals may also be attached to a carbocyclic aryl radical, or in which heteroaryl represents a bicyclic heteroaryl radical having up to and including 4 identical or different hetero atoms selected from nitrogen, oxygen or sulfur;

$R_5$ is a —COOH, —$CONH_2$, —CONH—OH, —PO(OH)$_2$, tetrazole, —$CH_2$OH, cyano or hydrogen;

aryl and heteroaryl radicals being, independently of one another, in each case unsubstituted or substituted by a substituent selected from the group consisting of halogen, lower alkyl, lower alkoxy, halo-lower alkyl, hydroxy, aryl-substituted lower alkoxy in which aryl represents phenyl, biphenylyl or naphthyl, carboxy, lower alkoxycarbonyl, amino, cyano, cyano-lower alkanoyl, and nitro;

or a pharmaceutically acceptable salt thereof.

The invention relates to a compound of formula I wherein $R_1$ is an aryl, preferably 2- or 3-naphthyl or a mono or disubstituted phenyl

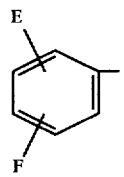

wherein E and F are each independently a hydrogen atom, a halogen atom such as fluorine, chlorine, bromine or, iodine atom, phenyl, lower alkyl such as methyl, lower alkoxy such as methoxy, trifluoromethyl, hydroxy, lower alkoxy, phenyl-lower alkoxy such as benzyloxy, or nitro; or $R_1$ is a heteroaryl, preferably 2- or 3-thienyl, 2- or 3-furanyl, 2-, 3- or 4-pyridyl;

$R_2$ is a hydrogen atom, or lower alkyl, preferably methyl or ethyl;

$R_3$ and $R_3'$ are each the same or different and is hydrogen, $C_3$–$C_8$cycloalkyl, aryl-lower alkyl, an aryl, preferably a 2- or 3-naphthyl or a monosubstituted phenyl

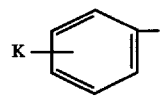

wherein K is a hydrogen atom, a halogen atom such as fluorine, chlorine, bromine, or iodine atom, lower alkyl such as methyl, lower alkoxy such as methoxy, trifluoromethyl, hydroxy, phenyl-lower alkoxy such as benzyloxy, nitro, aryl or heteroaryl; or heteroaryl preferably a 2- or 3-thienyl, 2- or 3-furanyl, 2-, 3-, or 4-pyridyl;

$R_3"$ is hydrogen, lower alkyl or aryl;

$R_2$ and $R_3"$ together form a lower alkylene group: —$(CH_2)_n$— wherein n is an integer of 1, 2 or 3; or $R_2$ and $R_3"$ together form a group represented by the formula: —$(CH_2)_p$—Ar— wherein p is zero or an integer of 1 or 2, and Ar is an aryl, preferably a naphthyl or a monosubstituted phenyl:

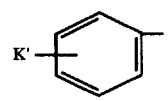

wherein K' is a hydrogen atom, a halogen atom such as fluorine, chlorine, bromine, or iodine atom, phenyl, lower alkyl such as methyl, lower alkoxy such as methoxy, hydroxy, trifluoromethyl or nitro; or Ar is a heteroaryl, preferably a thienyl, furanyl or pyridyl; wherein the valence of the —$(CH_2)_p$— binds to the nitrogen atom and the valence of the Ar binds to the carbon atom to which the $R_4$ binds;

C(=X) is C(=O), C(=S), C=N-lower alkyl; C=NH—OH, $CH_2$, or CHOH;

Y is —NH—, a lower alkyl-N<, preferably —N(CH$_3$)—, or —$CH_2$—; or

C(=X) is CHOH; and Y is —$CH_2$—;

$R_4$ is a group represented by the formula: —$(CH_2)_s$—Ar' wherein s is an integer of 1 or 2; and Ar' is an aryl, preferably phenyl, biphenyl, 2- or 3-naphthyl; or $R_4$ is a heteroaryl, preferably a 2- or 3-thienyl, 2- or 3-furanyl, 2-, 3- or 4-pyridyl, 3-indolyl, 2-, 3-, or 4-quinolinyl, 1-, 3- or 4-iso-quinolinyl, $R_5$ is a carboxy or —CONH—OH, PO(OH)$_2$ or tetrazole; or a pharmaceutically acceptable salt thereof.

The invention relates especially to a compound of formula I wherein $R_1$ is lower alkyl, $C_3$–$C_8$-cycloalkyl-lower alkyl, phenyl-lower alkyl, biphenylyl-lower alkyl, naphthyl-lower alkyl, $C_3$–$C_8$-cycloalkyl, phenyl, biphenylyl, naphthyl, phenyl-$C_3$–$C_8$-cycloalkyl, biphenylyl-$C_3$–$C_8$-cycloalkyl, naphthyl-$C_3$–$C_8$-cycloalkyl, lower alkoxy, phenyloxy, biphenyloxy, naphthyloxy, thienyl, furanyl, pyrrolyl, triazolyl, tetrazolyl, imidazolyl, oxazolyl, isoxazolyl, thiazolyl, isothiazolyl, pyridyl, pyranyl, pyridyl-phenyl, thienyl-phenyl, furyl-phenyl, pyrrolyl-phenyl, imidazolyl-phenyl, oxazolyl-phenyl, isoxazolyl-phenyl, thiazolyl-phenyl, isothiazolyl-phenyl, triazolyl-phenyl, tetrazolyl-phenyl, indolyl, 1-lower alkyl-indolyl, benzothiophenyl, benzofuranyl, quinolinyl, or isoquinolinyl;

$R_2$ is a hydrogen atom, lower alkyl, $C_3$–$C_8$-cycloalkyl, $C_3$–$C_8$-cycloalkyl-lower alkyl;

$R_3$ and $R_3'$ are each the same or different and each is hydrogen, lower alkyl, $C_3$–$C_8$-cycloalkyl, phenyl, biphenylyl, naphthyl, thienyl, furanyl, pyrrolyl, triazolyl, tetrazolyl, imidazolyl, oxazolyl, isoxazolyl, thiazolyl, isothiazolyl, pyridyl, pyranyl, pyridyl-phenyl, thienyl-phenyl, furyl-phenyl, pyrrolyl-phenyl, imidazolyl-phenyl, oxazolyl-phenyl, isoxazolyl-phenyl, thiazolyl-phenyl, isothiazolyl-phenyl, triazolyl-phenyl, tetrazolyl-phenyl, indolyl, 1-lower alkyl-indolyl, benzothiophenyl, benzofuranyl, quinolinyl, or isoquinolinyl; or $R_3$ and $R_3'$ together form fluorenyl, anthryl, or dibenzosuberyl;

$R_3''$ is hydrogen, lower alkyl, phenyl, biphenylyl, naphthyl; or $R_2$ and $R_3''$ together form a lower alkylene group —(CH$_2$)$_n$— wherein n is an integer of 1, 2 or 3; or $R_2$ and $R_3''$ together form a group represented by formula: —(CH$_2$)$_p$—Ar— or —Ar—(CH$_2$)$_p$—, respectively, wherein p is zero or an integer of 1 or 2, and Ar is a phenylene or pyridylene;

C(=X) is C(=O), C(=S), C(=NH), C(=N-lower alkyl); C=NH—OH, or CH$_2$;

Y is a direct bond, —NH—, a lower alkyl-N<, an oxygen atom, or methylene; or

C(=X) is CHOH and Y is a direct bond or methylene;

$R_4$ is —(CH$_2$)$_s$—Ar' wherein s is zero or an integer of 1, 2 or 3; and Ar' is phenyl, biphenylyl, naphthyl, thienyl, furanyl, pyrrolyl, triazolyl, tetrazolyl, imidazolyl, oxazolyl, isoxazolyl, thiazolyl, isothiazolyl, pyridyl, pyranyl, pyridyl-phenyl, thienyl-phenyl, furyl-phenyl, pyrrolyl-phenyl, imidazolyl-phenyl, oxazolyl-phenyl, isoxazolyl-phenyl, thiazolyl-phenyl, isothiazolyl-phenyl, triazolyl-phenyl, tetrazolyl-phenyl, indolyl, 1-lower alkyl-indolyl, benzothiophenyl, benzofuranyl, quinolinyl, or isoquinolinyl;

$R_5$ is —COOH, —CONH$_2$, —CONH—OH, or tetrazole; aryl and heteroaryl radicals being, independently of one another, in each case unsubstituted or substituted by a substituent selected from the group consisting of halogen, lower alkyl, lower alkoxy, halo-lower alkyl, hydroxy, phenyl-lower alkoxy, biphenylyl-lower alkoxy, naphthyl-lower alkoxy, carboxy, lower alkoxycarbonyl, amino, cyano, cyano-lower alkanoyl, and nitro;

or a pharmaceutically acceptable salt thereof.

The invention relates especially to compounds of the formula I wherein $R_1$ (i) is $C_1$–$C_7$-alkyl, $C_3$–$C_8$-cycloalkyl-$C_1$–$C_4$-alkyl, or phenyl-$C_1$–$C_4$-alkyl, or (ii) is $C_3$–$C_8$-cycloalkyl which may be substituted by $C_1$–$C_7$-alkyl; phenyl; biphenylyl, naphthyl, phenyl-$C_3$–$C_8$-cycloalkyl, $C_1$–$C_7$-alkoxy, phenoxy, thienyl, furyl, pyranyl, pyridyl, pyridyl-phenyl, thienyl-phenyl, furyl-phenyl, indolyl, 1-lower alkyl-indolyl, quinolinyl or isoquinolyl;

the aryl or heteroaryl radical being in each case, independently of one another, unsubstituted or substituted by a substituent selected from the group consisting of halogen, $C_1$–$C_7$-alkyl, $C_1$–$C_7$-alkoxy, halo-$C_1$–$C_7$-alkyl, hydroxy, phenyl-$C_1$–$C_4$-alkoxy, carboxy, $C_2$–$C_8$-alkoxycarbonyl, and nitro;

$R_2$ is hydrogen, $C_1$–$C_7$-alkyl, $C_3$–$C_8$-cycloalkyl, or $C_3$–$C_8$-cycloalkyl-$C_1$–$C_4$-alkyl;

$R_3$ is hydrogen, $C_1$–$C_7$-alkyl, $C_3$–$C_8$-cycloalkyl, phenyl-$C_1$–$C_4$-alkyl, phenyl, biphenylyl, naphthyl, thienyl, furyl, pyranyl, pyridyl, pyridyl-phenyl, thienyl-phenyl, furyl-phenyl, indolyl, 1-$C_1$–$C_4$-alkyl-indolyl, quinolinyl or isoquinolyl;

the aryl or heteroaryl being in each case, independently of one another, unsubstituted or substituted by a substitutent selected from the group consisting of halogen, $C_1$–$C_7$-alkyl, $C_1$–$C_7$-alkoxy, halo-$C_1$–$C_7$-alkyl, hydroxy, phenyl-$C_1$–$C_4$-alkoxy, carboxy, $C_2$–$C_8$-alkoxycarbonyl, and nitro;

$R_3'$ (i) is hydrogen or $C_1$–$C_7$-alkyl or (ii) is phenyl; biphenylyl; naphthyl; phenyl-$C_3$–$C_8$-cycloalkyl; thienyl, furyl, pyranyl, pyridyl, pyridyl-phenyl, thienyl-phenyl, furyl-phenyl, indolyl, 1-$C_1$–$C_4$-alkyl-indolyl, quinolinyl or isoquinolyl; the aryl or heteroaryl radical being unsubstituted or substituted by a substitutent selected from the group consisting of halogen, $C_1$–$C_7$-alkyl, $C_1$–$C_7$-alkoxy, halo-$C_1$–$C_7$-alkyl, hydroxy, phenyl-$C_1$–$C_4$-alkoxy, carboxy, $C_2$–$C_8$-alkoxycarbonyl, and nitro; or $R_3$ and $R_3'$ together form fluorenyl, anthryl, or dibenzosuberyl being in each case, independently of one another, unsubstituted or substituted by a substituent selected from the group consisting of halogen, $C_1$–$C_7$-alkyl, $C_1$–$C_7$-alkoxy, halo-$C_1$–$C_7$-alkyl, hydroxy, phenyl-$C_1$–$C_4$-alkoxy, carboxy, $C_2$–$C_8$-alkoxycarbonyl, and nitro;

$R_3''$ is hydrogen; or $R_2$ and $R_3''$ together form a lower alkylene group —(CH$_2$)$_n$— wherein n is an integer of 1, 2 or 3; or $R_2$ and $R_3''$ together form a group represented by the formula: —(CH$_2$)$_p$—Ar—, wherein p is zero or an integer of 1 or 2, the valence of the —(CH$_2$)$_p$— binds to the nitrogen atom and the valence of the Ar binds to the carbon atom to which the $R_3$" binds, and Ar is phenylene or pyridylene, each being unsubstituted or substituted by a substitutent selected from the group consisting of halogen, $C_1$–$C_7$-alkyl, $C_1$–$C_7$-alkoxy, halo-$C_1$–$C_7$-alkyl, hydroxy, phenyl-$C_1$–$C_4$-alkoxy, carboxy, $C_2$–$C_8$-alkoxycarbonyl, and nitro;

C(=X) is C(=O), C(=S), C(=N-$C_1$–$C_7$-alkyl); C=NH—OH, or CH$_2$;

Y is —NH—, a lower alkyl-N<, an oxygene atome, or methylene; or

C(=X) is CHOH; and Y is methylene;

$R_4$ is —(CH$_2$)$_s$—Ar' wherein s is zero or an integer of 1, 2 or 3; and Ar' is phenyl, naphthyl, biphenylyl, thienyl, furyl, pyranyl, pyridyl, pyridyl-phenyl, thienyl-phenyl, furyl-phenyl, indolyl, 1-$C_1$–$C_4$-alkyl-indolyl, quinolinyl or isoquinolyl; the aryl or heteroaryl radical being in each case, independently of one another, unsubstituted or substituted by a substitutent selected from the group consisting of halogen, $C_1$–$C_7$-alkyl, $C_1$–$C_7$-alkoxy, halo-$C_1$–$C_7$-alkyl, hydroxy, phenyl-$C_1$–$C_4$-alkoxy, carboxy, $C_2$–$C_8$-alkoxycarbonyl, and nitro; and $R_5$ is carboxy, CONH$_2$, CONH—OH, PO(OH)$_2$, 5H-1-tetrazolyl, CH$_2$OH, CN, or hydrogen;

or a pharmaceutically acceptable salt thereof.

The invention relates in particular to compounds of the formula I wherein $R_1$ is phenyl, biphenylyl or naphtyl each being, independently of one another, substituted by a substituent selected from the group consisting of halogen, $C_1-C_4$-alkyl, $C_1-C_4$-alkoxy, hydroxy, and trifluoromethyl; thienyl or pyridyl each being, independently of one another, unsubstituted or substituted by halogen or $C_1-C_4$-alkyl;

$R_2$ is hydrogen or $C_1-C_4$-alkyl;

$R_3$ is phenyl, biphenylyl, naphthyl, thienyl, pyridyl, pyridylphenyl, thienyl-phenyl, or furyl-phenyl;

the aryl or heteroaryl radical being in each case, independently of one another, unsubstituted or substituted by a substitutent selected from the group consisting of halogen, $C_1-C_4$-alkyl, $C_1-C_4$-alkoxy, hydroxy, and phenyl-$C_1-C_4$-alkoxy;

$R_3'$ is hydrogen or phenyl being unsubstituted or substituted by a substituent selected from the group consisting of halogen, $C_1-C_4$-alkyl, $C_1-C_4$-alkoxy, hydroxy, and phenyl-$C_1-C_4$-alkoxy; or $R_3$ and $R_3'$ together form dibenzosuberyl;

$R_3''$ is hydrogen; or $R_2$ and $R_3''$ together form a lower alkylene group —$(CH_2)_n$— wherein n is an integer of 2 or 3; or $R_2$ and $R_3''$ together form a group represented by the formula: —$(CH_2)_p$—Ar—, the valence of the —$(CH_2)_p$— binds to the nitrogen atom and the valence of the Ar binds to the carbon atom to which the $R_3''$ binds, wherein n is an integer of 2 or 3; and Ar is phenylene being unsubstituted or substituted by a substitutent selected from the group consisting of halogen, $C_1-C_4$-alkyl, $C_1-C_4$-alkoxy, hydroxy, and phenyl-$C_1-C_4$-alkoxy;

$C(=X)$ is $C(=O)$; and Y is —NH— or —$CH_2$—; or $C(=X)$ is CHOH; and Y is methylene;

$R_4$ is —$(CH_2)_s$—Ar' wherein s is the integer 1; and Ar' is phenyl, naphthyl, biphenylyl, pyridyl, indolyl, 1-$C_1-C_4$-alkyl-indolyl, or quinolinyl; the aryl or heteroaryl radical being in each case, independently of one another, unsubstituted or substituted by a substituent selected from the group consisting of halogen, $C_1-C_4$-alkyl, $C_1-C_4$-alkoxy, halo-$C_1-C_4$-alkyl, hydroxy, phenyl-$C_1-C_4$-alkoxy, carboxy, and $C_2-C_5$-alkoxycarbonyl; and $R_5$ is carboxy, $CONH_2$, or 5H-1-tetrazolyl;

or a pharmaceutically acceptable salt thereof.

The invention relates in particular to compounds of the formula I wherein $R_1$ represents phenyl substituted by $C_1-C_4$-alkyl such as methyl, $C_1-C_4$-alkoxy such as methoxy, halogen such as chloro, $CF_3$, hydroxy, or nitro;

$R_2$ is $C_1-C_4$-alkyl such as methyl or ethyl;

$R_3$ represents phenyl, biphenylyl such as 4-biphenylyl, naphthyl such as 2-naphthyl, thienyl such as 2- or 3-thienyl, furyl such as 2- or 3-furyl, tetrazolyl such as 1H-5-tetrazolyl, imidazolyl such as 1-imidazolyl, pyridyl such as 2-pyridyl, or quinolinyl such as 4-quinolinyl, pyridyl-phenyl such as 4-(2-pyridyl)-phenyl, thienyl-phenyl such as 4-(2- or 3-thienyl)-phenyl, isoxazolyl-phenyl such as 4-(3- or 5-isoxazolyl)-phenyl;

wherein said aryl and heteroaryl radicals, independently of one another, are in each case unsubstituted or substituted by a substituent selected from the group consisting of $C_1-C_4$-alkyl such as methyl, $C_1-C_4$-alkoxy such as methoxy, halogen such as chloro, $CF_3$, hydroxy, cyano, cyano-$C_2-C_5$-alkanoyl such as cyano-acetyl, and nitro;

$R_3'$ is hydrogen, phenyl or phenyl substituted by $C_1-C_4$-alkyl such as methyl, $C_1-C_4$-alkoxy such as methoxy, halogen such as chloro, $CF_3$, hydroxy, or nitro;

$R_3''$ is hydrogen;

$C(=X)$ is $C(=O)$ or $C(=S)$;

Y is NH;

$R_4$ is —$(CH_2)_s$—Ar' wherein s is the integer 1; and Ar' is phenyl, naphthyl such as 2-naphthyl, biphenylyl such as 4-biphenylyl, indol-3-yl, 1-$C_1-C_4$-alkyl-indol-3-yl such as 1-methyl-indol-3-yl, or quinolinyl such as 4-quinolinyl; wherein said aryl and heteroaryl radicals, independently of one another, are in each case unsubstituted or substituted by a substituent selected from the group consisting of $C_1-C_4$-alkyl such as methyl, $C_1-C_4$-alkoxy such as methoxy, halogen such as chloro, $CF_3$, hydroxy, and nitro;

$R_5$ is COOH;

or a pharmaceutically acceptable salt thereof.

The invention relates in particular to compounds of the formula I wherein $R_1$ represents 3,5-di-$C_1-C_4$-alkyl-phenyl, preferably 3,5-di-methyl-phenyl;

$R_2$ is $C_1-C_4$-alkyl, preferably methyl;

(i) $R_3$ is 4-biphenylyl, 4-(2-thienyl)-phenyl, 4-(3-thienyl)-phenyl, 4-(2-furyl)-phenyl, 4-(3-isoxazolyl)-phenyl, 4-(5-isoxazolyl)-phenyl, 4-(1-imidazolyl)-phenyl, or 4-(2-pyridyl)-phenyl;

$R_3'$ is hydrogen or phenyl;

$R_3''$ is hydrogen; or (ii) $R_3$ is phenyl or phenyl substituted by cyano or cyano-$C_2-C_5$-alkanoyl, preferably cyano-acetyl;

$R_3'$ and $R_3''$ each are hydrogen;

$C(=X)$ is $(C=O)$ or $C(=S)$;

Y is NH;

$R_4$ is —$(CH_2)_s$—Ar' wherein s is the integer 1; and Ar' is indol-3-yl; and $R_5$ is carboxy;

or a pharmaceutically acceptable salt thereof.

The invention relates in particular to compounds of the formula I wherein $R_1$ is phenyl substituted by halogen or $C_1-C_4$-alkyl, especially 3,5-dichloro-phenyl or 3,5-dimethyl-phenyl;

$R_2$ is $C_1-C_4$-alkyl, especially methyl or ethyl;

$R_3$ is phenyl being unsubstituted or substituted by halogen, $C_1-C_4$-alkoxy, hydroxy, or phenyl-$C_1-C_4$-alkoxy, especially 2- or 4-chloro-phenyl, 4-hydroxyphenyl, 4-methoxyphenyl, or 4-benyzloxyphenyl; biphenylyl, especially 4-biphenylyl; naphthyl, especially 2- or 3-naphthyl; thienyl, especially 3-thienyl; thienyl being substituted by $C_1-C_4$-alkyl, especially 5-methyl-3-thienyl; pyridyl, especially 2-pyridyl; pyridyl-phenyl, especially 4-(2-pyridyl)-phenyl; or thienyl-phenyl, especially 4-(3-thienyl)-phenyl;

$R_3'$ is hydrogen or phenyl; or $R_3''$ is hydrogen; or $C(=X)$ is $C(=O)$; and Y is —NH— or —$CH_2$—; or $C(=X)$ is CHOH; and Y is methylene;

$R_4$ is —$(CH_2)_s$—Ar' wherein s is the integer 1; and Ar' is naphthyl, especially 2- or 3-naphthyl, indolyl, especially 3-indolyl, or quinolinyl, especially 4-quinolyl; and $R_5$ is carboxy;

or a pharmaceutically acceptable salt thereof.

The invention relates in particular to compounds of the formula I wherein $R_1$ represents 3,5-di-$C_1-C_4$-alkyl-phenyl, especially 3,5-dimethyl-phenyl, or 3,5-di-halophenyl, especially 3,5-dichloro-phenyl;

$R_2$ is $C_1-C_4$-alkyl, especially methyl or ethyl;

(i) $R_3$ is phenyl; and $R_3'$ is phenyl; or (ii) $R_3$ is phenyl, 4-biphenylyl, or 4-(2-pyridyl)-phenyl; and $R_3'$ is hydrogen; and $R_3''$ is hydrogen;

$C(=X)$ is $C(=O)$; Y is —NH—;

$R_4$ is —$(CH_2)_s$—Ar' wherein s is the integer 1; and Ar' is 3-indolyl; and $R_5$ is a COOH;
or a pharmaceutically acceptable salt thereof.

The invention relates in particular to compounds of the formula I wherein $R_1$ represents 3,5-di-$C_1$-$C_4$alkyl-phenyl, especially 3,5-dimethyl-phenyl;
$R_2$ is $C_1$-$C_2$-alkyl;
$R_3$ is 4-biphenylyl, 4-(2-thienyl)-phenyl, 4-(3-thienyl)-phenyl, 4-(2-furyl)-phenyl, 4-(3-isoxazolyl)-phenyl, 4-(5-isoxazolyl)-phenyl, or 4-(1-imidazolyl)-phenyl;
$R_3'$ and $R_3''$ each are hydrogen;
C(=X) is C(=O);
Y is NH;
$R_4$ is —$(CH_2)_s$—Ar' wherein s is the integer 1; and Ar' is 3-indolyl; and
$R_5$ is a COOH;
or a pharmaceutically acceptable salt thereof.

The invention relates in particular to compounds of the formula I wherein $R_1$ represents represents 3,5-dimethylphenyl;
$R_2$ is methyl;
$R_3$ is 4-biphenylyl, 4-(2-thienyl)-phenyl, 4-(3-thienyl)-phenyl, 4-(3-isoxazolyl)-phenyl, 4-(5-isoxazolyl)-phenyl, or 4-(1-imidazolyl)-phenyl;
$R_3'$ and $R_3''$ each are hydrogen;
C(=X) is C(=O);
Y is NH;
$R_4$ is —$(CH_2)_s$—Ar' wherein s is the integer 1; and Ar' is 3-indolyl; and
$R_5$ is a COOH;
or a pharmaceutically acceptable salt thereof.

The invention relates in particular to the novel compounds shown in the examples and to the methods for their preparation described therein.

Preferred stereochemistry is

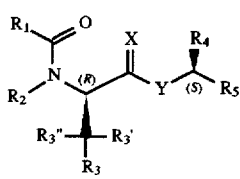

for those compounds wherein Y is different from —$CH_2$— and

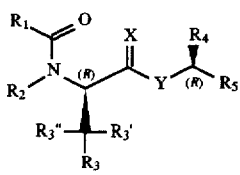

for those compounds wherein Y represents —$CH_2$—.

The invention relates to processes for the preparation of the compounds according to the invention. The preparation of compounds of the formula I and their salts is carried out in a manner known per se and comprises, for example, a) reacting a compound of formula

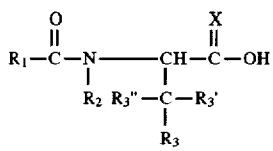
(IIa)

or a salt or a reactive acid derivative thereof with a compound of formula

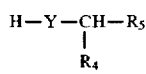
(IIb)

free functional groups, with the exception of those participating in the reaction, being optionally in protected form, and any protecting groups present are removed, or b) reacting a compound of formula

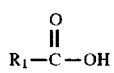
(IIIa)

or a salt or reactive acid derivative thereof with a compound of formula

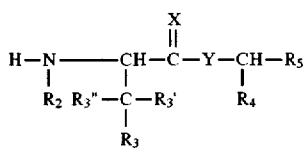
(IIIb)

free functional groups, with the exception of those participating in the reaction, being optionally in protected form, and any protecting groups present are removed, and, if desired, converting a compound I obtainable according to the process or in another manner, in free form or in salt form, into another compound I, separating a mixture of isomers obtainable according to the process and isolating the desired isomer and/or converting a free compound I obtainable according to the process into a salt or converting a salt of a compound I obtainable according to the process into the free compound I or into another salt.

The reactions described above and below in the variants are carried out in a manner known per se, for example in the absence or, customarily, in the presence of a suitable solvent or diluent or a mixture thereof, the reaction, as required, being carried out with cooling, at room temperature or with warming, for example in a temperature range from about −80° C. up to the boiling point of the reaction medium, preferably from about −10° to about +200° C., and, if necessary, in a closed vessel, under pressure, in an inert gas atmosphere and/or under anhydrous conditions.

Process variants a) and b)

The compounds of formula IIa or IIIa, respectively, contain a free carboxy group or reactive acid derivatives thereof, for example the derived activated esters or reactive anhydrides, and also reactive cyclic amides. The reactive acid derivatives can also be formed in situ.

Activated esters of compounds of formula IIa or IIIa, respectively, having a carboxy group are especially esters unsaturated at the linking carbon atom of the esterifying radical, for example of the vinyl ester type, such as vinyl esters (obtainable, for example, by transesterification of a corresponding ester with vinyl acetate; activated vinyl ester method), carbamoyl esters (obtainable, for example, by treatment of the corresponding acid with an isoxazolium reagent; 1,2-oxazolium or Woodward method), or 1-lower alkoxyvinyl esters (obtainable, for example, by treatment of the corresponding acid with a lower alkoxyacetylene; ethoxyacetylene method), or esters of the amidino type, such as N,N'-disubstituted amidino esters (obtainable, for example, by treatment of the corresponding acid with a suitable N,N'-disubstituted carbodiimide, for example N,N'-dicyclohexylcarbodiimide; carbodiimide method), or N,N-disubstituted amidino esters (obtainable, for example, by treatment of the corresponding acid with an N,N- disubstituted cyanamide; cyanamide method), suitable aryl esters, especially phenyl esters suitably substituted by electron-attracting substituents (obtainable, for example, by treatment of the corresponding acid with a suitably substituted phenol, for example 4-nitrophenol, 4-methylsulfonylphenol, 2,4,5-trichlorophenyl, 2,3,4,5,6-pentachlorophenol or 4-phenyldiazophenol, in the presence of a condensation agent, such as N,N'-dicyclohexylcarbodiimide; activated aryl esters method), cyanomethyl esters (obtainable, for example, by treatment of the corresponding acid with chloroacetonitrile in the presence of a base; cyanomethyl esters method), thioesters, especially unsubstituted or substituted, for example nitro-substituted, phenylthio esters (obtainable, for example, by treatment of the corresponding acid with unsubstituted or substituted, for example nitro-substituted, thiophenols, inter alia by the anhydride or carbodiimide method; activated thiol esters method), or especially amino or amido esters (obtainable, for example, by treatment of the corresponding acid with an N-hydroxyamino or N-hydroxyamido compound, for example N-hydroxysuccinimide, N-hydroxypiperidine, N-hydroxyphthalimide, N-hydroxy-5-norbornene-2,3-dicarboxylic acid imide, 1-hydroxybenzotriazole or 3-hydroxy-3,4-dihydro-1,2,3-benzotriazin-4-one, for example by the anhydride or carbodiimide method; activated N-hydroxy esters method). Internal esters, for example γ-lactones, can also be used.

Anhydrides of acids may be symmetric or preferably mixed anhydrides of those acids, for example anhydrides with inorganic acids, such as acid halides, especially acid fluorides (obtainable, for example, by treatment of the corresponding acid with e.g. trifluorotriazine), acid chlorides (obtainable, for example, by treatment of the corresponding acid with thionyl chloride, phosphorus pentachloride, phosgene or oxalyl chloride; acid chloride method), azides (obtainable, for example, from a corresponding acid ester via the corresponding hydrazide by treatment thereof with nitrous acid; azide method), anhydrides with carbonic acid semi-esters, for example carbonic acid lower alkyl semi-esters (obtainable, for example, by treatment of the corresponding acid with chloroformic acid lower alkyl esters or with a 1-lower alkoxycarbonyl-2-lower alkoxy-1,2-dihydroquinoline; mixed O-alkylcarbonic acid anhydrides method), or anhydrides with dihalogenated, especially dichlorinated, phosphoric acid (obtainable, for example, by treatment of the corresponding acid with phosphorus oxychloride; phosphorus oxychloride method), anhydrides with other phosphoric acid derivatives (for example those obtainable with phenyl-N-phenylphosphoramidochloridate or by reaction of alkylphosphoric acid amides in the presence of sulfonic acid anhydrides and/or racemisation-reducing additives, such as N-hydroxybenzotriazole, or in the presence of cyanophosphonic acid diethyl ester) or with phosphorous acid derivatives, or anhydrides with organic acids, such as mixed anhydrides with organic acids, such as mixed anhydrides with organic carboxylic acids (obtainable, for example, by treatment of the corresponding acid with an unsubstituted or substituted lower alkane- or phenyl-lower alkane-carboxylic acid halide, for example phenylacetic acid chloride, pivalic acid chloride or trifluoroacetic acid chloride; mixed carboxylic acid anhydrides method) or with organic sulfonic acids (obtainable, for example, by treatment of a salt, such as an alkali metal salt, of the corresponding acid with a suitable organic sulfonic acid halide, such as lower alkane- or aryl-, for example methane- or p-toluene-sulfonic acid chloride; mixed sulfonic acid anhydrides method) and symmetric anhydrides (obtainable, for example, by condensation of the corresponding acid in the presence of a carbodiimide or 1-diethylaminopropyne; symmetric anhydrides method).

Suitable cyclic amides are especially amides having five-membered diazacycles of aromatic character, such as amides with imidazoles, for example imidazole (obtainable, for example, by treatment of the corresponding acid with N,N'-carbonyldiimidazole; imidazole method), or pyrazole, for example 3,5-dimethylpyrazole (obtainable, for example, via the acid hydrazide by treatment with acetylacetone; pyrazolide method).

The condensation of a free carboxylic acid (IIb or IIIb, respectively) with the corresponding amine can be carried out preferably in the presence of one of the customary condensation agents, or using carboxylic acid anhydrides or carboxylic acid halides, such as chlorides, or activated carboxylic acid esters, such as p-nitrophenyl esters. Customary condensation agents are, for example, carbodiimides, for example diethyl-, dipropyl-, N-ethyl-N'-(3-dimethylaminopropyl)-carbodiimide or especially dicyclohexylcarbodiimide, also suitable carbonyl compounds, for example carbonylimidazole, 1,2-oxazolium compounds, for example 2-ethyl-5-phenyl-1,2-oxazolium 3'-sulfonate and 2-tert-butyl-5-methylisoxazolium perchlorate, or a suitable acylamino compound, for example 2-ethoxy-1-ethoxycarbonyl-1,2-dihydroquinoline, N,N,N',N'-tetraalkyluronium compounds, such as O-benzotriazol-1-yl-N,N,N',N'-tetramethyluronium hexafluorophosphate, also activated phosphoric acid derivatives, for example diphenylphosphoryl azide, diethylphosphoryl cyanide, phenyl-N-phenylphosphoroamidochloridate bis(2-oxo-3-oxazolidinyl)phosphinic acid chloride or 1-benzotriazolyloxy-tris(dimethylamino)phosphonium hexafluorophosphate.

If desired, an organic base is added, preferably a tertiary amine, for example a tri-lower alkylamine having bulky radicals, for example ethyl diisopropylamine or triethylamine, and/or a heterocyclic base, for example 4-dimethylaminopyridine or preferably N-methylmorpholine or pyridine.

The condensation of activated esters, reactive anhydrides or reactive cyclic amides with the corresponding amines is customarily carried out in the presence of an organic base, for example simple tri-lower alkylamines, for example triethylamine or tributylamine, or one of the above-mentioned organic bases. If desired, a condensation agent is additionally used, for example as described for free carboxylic acids.

The condensation of acid anhydrides with amines can be effected, for example, in the presence of inorganic carbonates, for example ammonium or alkali metal carbonates or hydrogen carbonates, such as sodium or potassium carbonate or hydrogen carbonate (if desired together with a sulfate).

Carboxylic acid chlorides, for example the chlorocarbonic acid derivatives derived from the acid of formula. The condensation of a free carboxylic acid with the corresponding amine can be carried out preferably in the presence of one of the customary condensation agents, or using carboxylic acid anhydrides or carboxylic acid halides, such as chlorides, or activated carboxylic acid esters, such as p-nitrophenyl esters. Customary condensation agents are, for example, carbodiimides, for example diethyl-, dipropyl-, N-ethyl-N'-(3-dimethylaminopropyl)-carbodiimide or especially dicyclohexylcarbodiimide, also suitable carbonyl compounds, for example carbonylimidazole, 1,2-oxazolium compounds, for example 2-ethyl-5-phenyl-1,2-oxazolium 3'-sulfonate and 2-tert-butyl-5-methylisoxazolium perchlorate, or a suitable acylamino compound, for example 2-ethoxy-1-ethoxycarbonyl-1,2-dihydroquinoline, N,N,N',N'-tetraalkyluronium compounds, such as O-benzotriazol-1-yl-N,N,N',N'-tetramethyluronium hexafluorophosphate, also activated phosphoric acid derivatives, for example diphenylphosphoryl azide, diethylphosphoryl cyanide, phenyl-N-phenylphosphoroamidochloridate, bis(2-oxo-3-oxazolidinyl)phosphinic acid chloride or 1-benzotriazolyloxy-tris(dimethylamino)phosphonium hexafluorophosphate.

If desired, an organic base is added, preferably a tertiary amine, for example a tri-lower alkylamine having bulky radicals, for example ethyl diisopropylamine or triethylamine, and/or a heterocyclic base, for example 4-dimethylaminopyridine or preferably N-methylmorpholine or pyridine.

The condensation of activated esters, reactive anhydrides or reactive cyclic amides with the corresponding amines is customarily carried out in the presence of an organic base, for example simple tri-lower alkylamines, for example triethylamine or tributylamine, or one of the above-mentioned organic bases. If desired, a condensation agent is additionally used, for example as described for free carboxylic acids.

The condensation of acid anhydrides with amines can be effected, for example, in the presence of inorganic carbonates, for example ammonium or alkali metal carbonates or hydrogen carbonates, such as sodium or potassium carbonate or hydrogen carbonate (if desired together with a sulfate).

Carboxylic acid chlorides, for example the chlorocarbonic acid derivatives derived from the acid of formula IIa or IIIa, respectively, are condensed with the corresponding amines preferably in the presence of an organic amine, for example the above-mentioned tri-lower alkylamines or heterocyclic bases, where appropriate in the presence of a hydrogen sulfate.

The condensation is preferably carried out in an inert, aprotic, preferably anhydrous, solvent or solvent mixture, for example in a carboxylic acid amide, for example formamide or dimethylformamide, a halogenated hydrocarbon, for example methylene chloride, carbon tetrachloride or chlorobenzene, a ketone, for example acetone, a cyclic ether, for example tetrahydrofuran, an ester, for example ethyl acetate, or a nitrile, for example acetonitrile, or in a mixture thereof, as appropriate at reduced or elevated temperature, for example in a temperature range of from approximately −40° C. to approximately +100° C., preferably from approximately −10° C. to approximately +50° C., and in the case where arylsulfonyl esters are used also at approximately from +100° C. to +200° C., and where appropriate under an inert gas atmosphere, for example a nitrogen or argon atmosphere.

Aqueous, for example alcoholic, solvents, for example ethanol, or aromatic solvents, for example benzene or toluene, may also be used. When alkali metal hydroxides are present as bases, acetone can also be added where appropriate.

The condensation can also be carried out in accordance with the technique known as solid phase synthesis which originates from R. Merrifield and is described, for example, in Angew. Chem. 97, 801–812 (1985), Naturwissenschaften 71, 252–258 (1984) or in R. A. Houghten, Proc. Natl. Acad. Sci. U.S.A. 82, 5131–5135 (1985).

The starting material, the intermediates can be prepared according to conventional methods known to the artisan, to methods generally described herein and to methods especially as illustrated in the examples.

The starting material of the formula IIa, in which Y represents oxygen or sulfur, is accessible, for example, by reacting a compound of formula IIIa or a salt or a reactive derivative thereof with an ester of a compound of formula

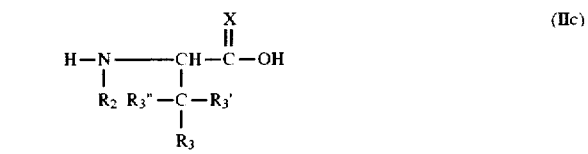

using e.g. coupling conditions as described in connection with process variants a) and b), optionally converting the resulting ester into a corresponding thioester, for example, by treating the ester with Lawesson's reagent, and subsequent hydrolysis of the resulting ester, for example, using suitable bases such lithium hydroxide.

Compounds of formula (IIc) deriving from natural α-amino acids are essentially known or may be manufactured in using conventional methods known to the artisan. Compounds of formula (IIc) in which $R_3$ is aryl or heteroaryl are either known or may be manufactured using conventional methods known to the artisan, for example, as outlined in schemes II to IV and in the working examples.

Compounds of formulae (IIb) and (IIIa) are either known or may be manufactured using conventional methods known to the artisan.

Starting material of formula (IIIb) is either known or may be manufactured using conventional methods known to the artisan, for example, by reacting an N-protected compound of formula (IIc) with a compound of formula (IIb) using e.g. coupling conditions as described in connection with process variants a) and b).

As example, compounds of the present invention represented by the general formula (I) wherein X represents oxygen, Y is —NH—, lower alkyl-N, or oxygen, and $R_5$ is COOH (represented by formula I') are produced, for example, according to SCHEME I, from an intermediate represented by the formula (IIa).

The intermediate (IIa) is produced, for example, according to SCHEMES II and III.

As example, compounds according to the present invention represented by formula (I) wherein C(=X) represents C=O, CH—OH or C=N—OH, and Y is $CH_2$, and $R_5$ is carboxy, are manufactured, for example, according to Scheme IV;

compounds according to the present invention represented by formula (I) wherein C(=X) represents C=S or C=N-lower alkyl, and Y is NH, are manufactured, for example, according to Scheme V;

compounds according to the present invention represented by formula (I) wherein $R_5$ represents $CH_2OH$, $CONH_2$, CN, tetrazolyl, or CO—NO—OH are produced, for example, according to Scheme VI.

SCHEME I

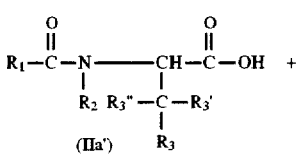

19
-continued
SCHEME I
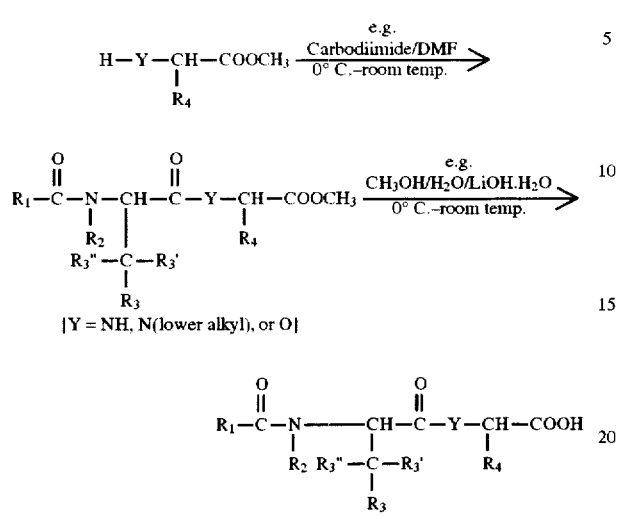
SCHEME II
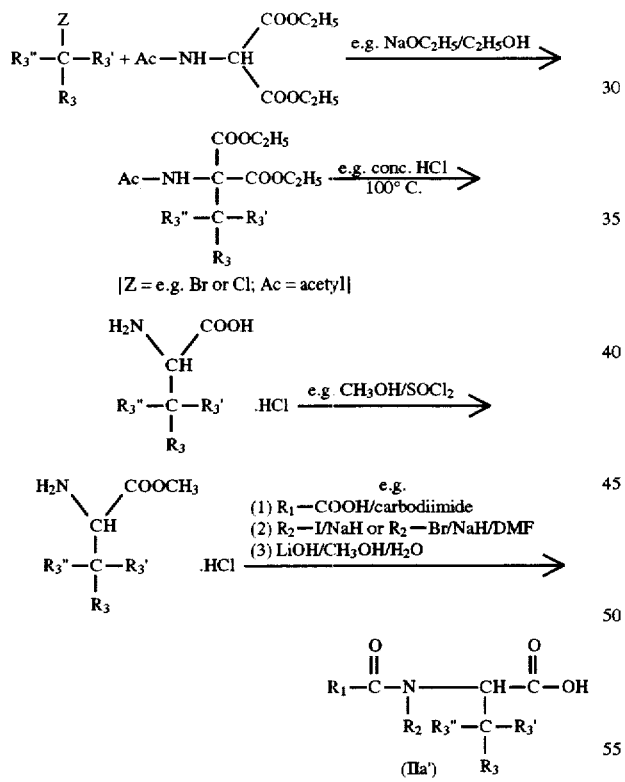
SCHEME III
(a)
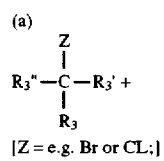
20
-continued
SCHEME III
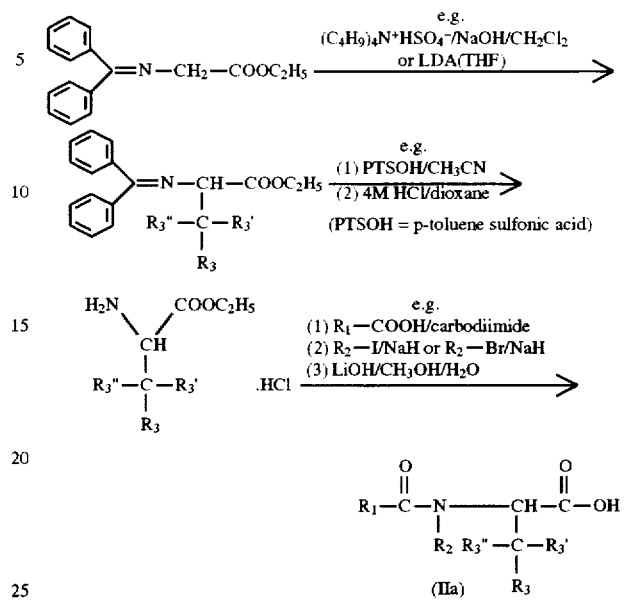
(b) especially for intermediates in whcih R₃' and R₃" each are hydrogen:
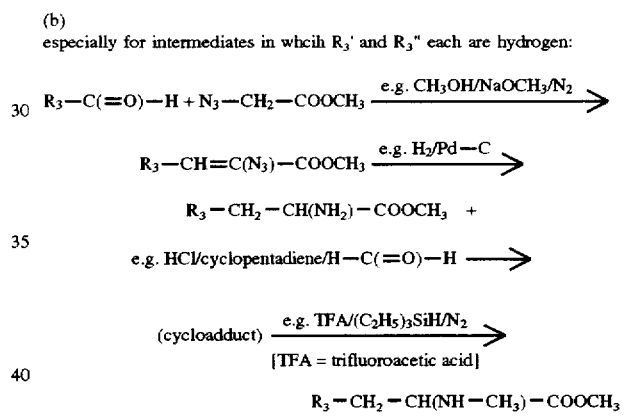
SCHEME IV
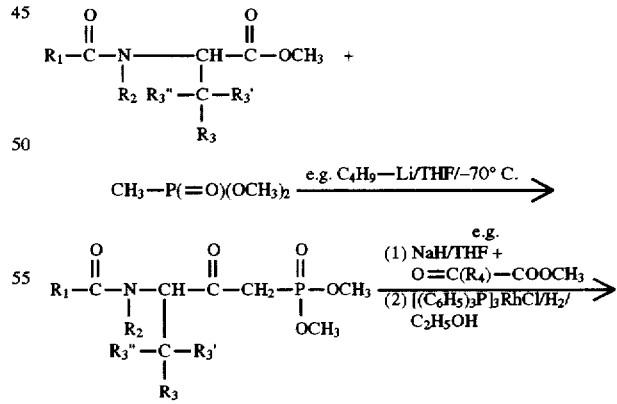
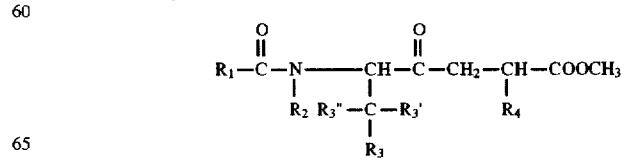

SCHEME IV (a) (1) e.g. NaBH₄/CH₃OH; (2) LiOH/H₂O/CH₃OH ⟶

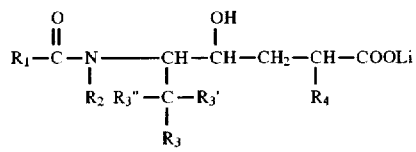

(b) (2) e.g. NH₂—OH/CH₃OH; (2) LiOH/H₂O/CH₃OH ⟶

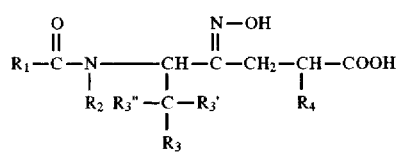

SCHEME V (a)

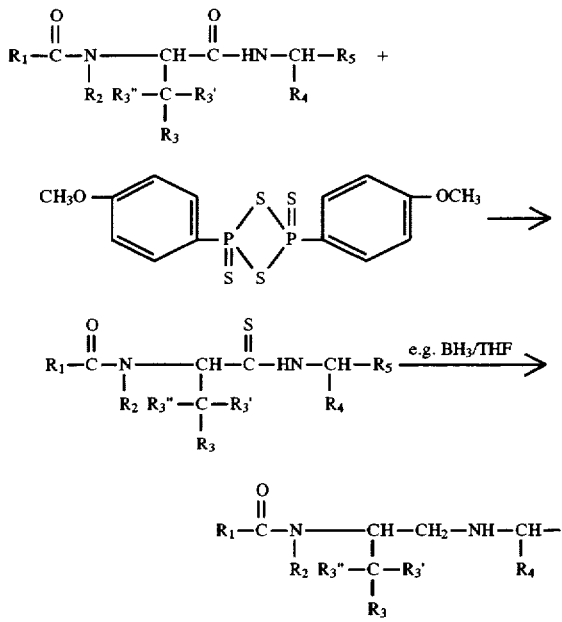

(b)

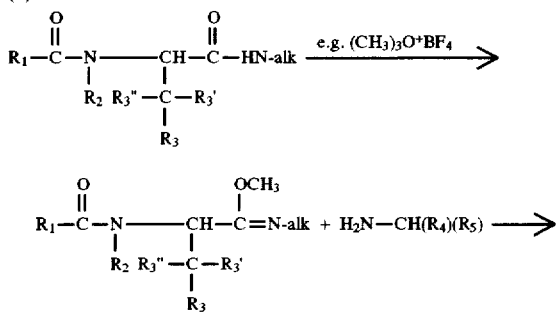

[R₂ is preferably different from hydrogen]

SCHEME V -continued

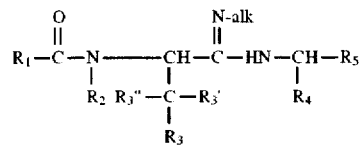

SCHEME VI

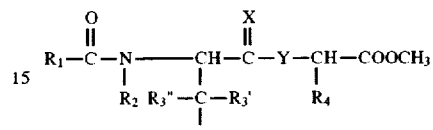

(a) + e.g. NaBH₄/cat.CuSO₄/H₂O/C₂H₅OH or Redal ⟶

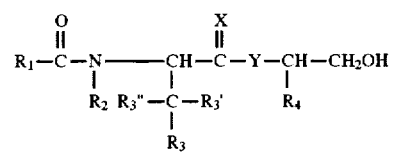

(b) + e.g. H₂N—OH/CH₃OH ⟶

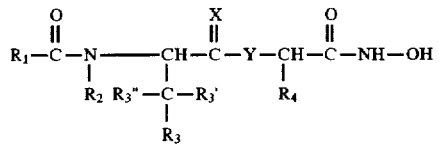

(c) + e.g. NH₃ ⟶

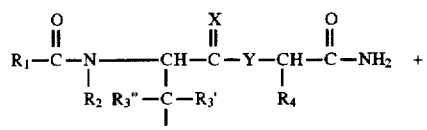

e.g. POCl₃/imidazole ⟶

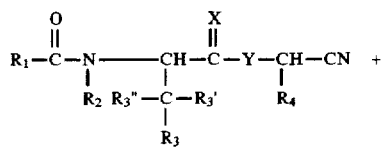

e.g. (C₄H₉)₃SnN₃ ⟶

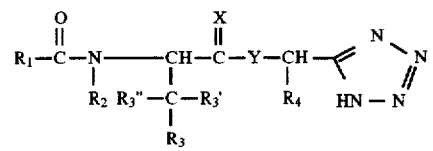

Functional groups in starting materials (e.g. R₅) that are not to participate in the reaction, especially carboxy, can be protected by suitable protecting groups (conventional protecting groups) which are customarily used in the synthesis of peptide compounds.

Those protecting groups may already be present in the precursors and are intended to protect the relevant functional groups against undesired secondary reactions, such as acylation, esterification, or solvolysis, etc. In certain cases the protecting groups can additionally cause the reactions to proceed selectively, for example stereoselectively. It is a characteristic of protecting groups that they can be removed easily, i.e. without undesired secondary reactions, for example by solvolysis, reduction, photolysis, and also enzymatically, for example also under physiological conditions. Radicals analogous to protecting groups may, however, also be present in the end products. Hereinbefore and hereinafter, it is protecting groups in the narrower sense that are referred to unless the relevant radicals are present in the end products.

The protection of functional groups by such protecting groups, the protecting groups themselves and the reactions for their removal are described, for example, in standard works such as J. F. W. McOmie, "Protective Groups in Organic Chemistry", Plenum Press, London and New York 1973, in Th. W. Greene, "Protective Groups in Organic Synthesis", Wiley, New York 1981, in "The Peptides"; Volume 3 (E. Gross and J. Meienhofer, eds.), Academic Press, London and New York 1981, in "Methoden der organischen Chemie", Houben-Weyl, 4th edition, Volume 15/I, Georg Thieme Verlag, Stuttgart 1974, in H. D. Jakubke and H. Jescheit, "Aminosauren, Peptide, Proteine" ("Amino acids, peptides, proteins"), Verlag Chemie, Weinheim, Deerfield Beach and Basel 1982, and in Jochen Lehmann, "Chemie der Kohlenhydrate: Monosaccharide und Derivate" ("The Chemistry of Carbohydrates: monosaccharides and derivatives"), Georg Thieme Verlag, Stuttgart 1974.

A carboxy group is protected, for example, in the form of an ester group which can be removed selectively under mild conditions. A carboxy group protected in esterified form is esterified especially by a lower alkyl group that is preferably branched in the 1-position of the lower alkyl group or substituted in the 1- or 2-position of the lower alkyl group by suitable substituents.

A protected carboxy group esterified by a lower alkyl group is, for example, methoxycarbonyl or ethoxycarbonyl.

A protected carboxy group esterified by a lower alkyl group that is branched in the 1-position of the lower alkyl group is, for example, tert-lower alkoxycarbonyl, for example tert-butoxycarbonyl.

A protected carboxy group esterified by a lower alkyl group that is substituted in the 1- or 2-position of the lower alkyl group by suitable substituents is, for example, arylmethoxycarbonyl having one or two aryl radicals, wherein aryl is phenyl that is unsubstituted or mono-, di- or trisubstituted, for example, by lower alkyl, for example tert-lower alkyl, such as tert-butyl, lower alkoxy, for example methoxy, hydroxy, halogen, for example chlorine, and/or by nitro, for example benzyloxycarbonyl, benzyloxycarbonyl substituted by the mentioned substituents, for example 4-nitrobenzyloxycarbonyl or 4-methoxybenzyloxycarbonyl, diphenylmethoxycarbonyl or diphenylmethoxycarbonyl substituted by the mentioned substituents, for example di(4-methoxyphenyl)-methoxycarbonyl, and also carboxy esterified by a lower alkyl group, the lower alkyl group being substituted in the 1- or 2-position by suitable substituents, such as 1-lower alkoxy-lower alkoxycarbonyl, for example methoxymethoxycarbonyl, 1-methoxyethoxycarbonyl or 1-ethoxyethoxycarbonyl, 1-lower alkylthio-lower alkoxycarbonyl, for example 1-methylthiomethoxycarbonyl or 1-ethylthioethoxycarbonyl, aroylmethoxycarbonyl wherein the aroyl group is benzoyl that is unsubstituted or substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, as well as 2-(tri-substituted silyl)-lower alkoxycarbonyl wherein the substituents are each independently of the others an aliphatic, araliphatic, cycloaliphatic or aromatic hydrocarbon radical that is unsubstituted or substituted, for example, by lower alkyl, lower alkoxy, aryl, halogen and/or by nitro, for example lower alkyl, phenyl-lower alkyl, cycloalkyl or phenyl each of which is unsubstituted or substituted as above, for example 2-tri-lower alkylsilyl-lower alkoxycarbonyl, such as 2-tri-lower alkylsilylethoxycarbonyl, for example 2-trimethylsilylethoxycarbonyl or 2-(di-n-butyl-methylsilyl)-ethoxycarbonyl, or 2-triarylsilylethoxycarbonyl, such as triphenylsilylethoxycarbonyl.

A carboxy group can also be protected in the form of an organic silyloxycarbonyl group. An organic silyloxycarbonyl group is, for example, a tri-lower alkylsilyloxycarbonyl group, for example trimethylsilyloxycarbonyl. The silicon atom of the silyloxycarbonyl group can also be substituted by two lower alkyl groups, for example methyl groups, and the amino group or the carboxy group of a second molecule of formula I. Compounds having such protecting groups can be prepared, for example, using dimethylchlorosilane as silylating agent.

A protected carboxy group is preferably lower alkoxycarbonyl, for example methoxy-, ethoxy- or tert-butoxycarbonyl, benzyloxycarbonyl, 4-nitrobenzyloxycarbonyl, 9-fluorenylmethoxycarbonyl or diphenylmethoxycarbonyl.

The removal of protecting groups that are not constituents of the desired end product of formula I, for example the carboxy-protecting groups, is effected in a manner known per se, for example by means of solvolysis, especially hydrolysis, alcoholysis or acidolysis, or by means of reduction, especially hydrogenolysis or chemical reduction, as well as by photolysis, as appropriate stepwise or simultaneously, it being possible also to use enzymatic methods. The removal of the protecting groups is described, for example, in the standard works mentioned above in the section relating to "Protecting groups".

For example, protected carboxy, for example lower alkoxycarbonyl, tert-lower alkoxycarbonyl, lower alkoxycarbonyl substituted in the 2-position by a trisubstituted silyl group or in the 1-position by lower alkoxy or lower alkylthio, or unsubstituted or substituted diphenylmethoxycarbonyl can be converted into free carboxy by treatment with a suitable acid, such as formic acid, hydrogen chloride or trifluoroacetic acid, where appropriate with the addition of a nucleophilic compound, such as phenol or anisole. Carboxy can also be freed from lower alkoxycarbonyl by means of bases, such as hydroxides, for example alkali metal hydroxides, such as lithium hydroxide, sodium hydroxide or potassium hydroxide. Unsubstituted or substituted benzyloxycarbonyl can be freed, for example, by means of hydrogenolysis, i.e. by treatment with hydrogen in the presence of a metal hydrogenation catalyst, such as a palladium catalyst. In addition, suitably substituted benzyloxycarbonyl, such as 4-nitrobenzyloxycarbonyl, can also be converted into free carboxy by reduction, for example by treatment with an alkali metal dithionate, such as sodium dithionate, or with a reducing metal, for example zinc, or a reducing metal salt, such as a chromium(II) salt, for example chromium(II) chloride, customarily in the presence of a hydrogen-yielding agent that, together with the metal, is capable of producing nascent hydrogen, such as an acid, especially a suitable carboxylic acid, such as an unsubstituted or substituted, for example hydroxy-substituted, lower alkanecarboxylic acid, for example acetic acid, formic acid, glycolic acid, diphenylglycolic acid, lactic acid, mandelic acid, 4-chloromandelic acid or tartaric acid, or in the presence of an alcohol or thiol, water preferably being added. By treatment with a reducing metal or metal salt, as described above, 2-halo-lower alkoxycarbonyl (where appropriate after conversion of a 2-bromo-lower alkoxycarbonyl group into a corresponding 2-iodo-lower alkoxycarbonyl group) or aroylmethoxycarbonyl can also be converted into free carboxy. Aroylmethoxycarbonyl can also be cleaved by treatment with a nucleophilic, preferably salt-forming, reagent, such as sodium thiophenolate or sodium iodide. 2-(tri-substituted silyl)-lower alkoxycarbonyl, such as 2-tri-lower alkylsilyl-lower alkoxycarbonyl, can also be converted into free carboxy by treatment with a salt of hydrofluoric acid that yields the fluoride anion, such as an alkali metal fluoride, for example sodium or potassium fluoride, where appropriate in the presence of a macrocyclic polyether ("Crown ether"), or with a fluoride of an organic quaternary base, such as tetra-lower alkylammonium fluoride or tri-lower alkylaryl-lower alkylammonium fluoride, for example tetraethylammonium fluoride or tetrabutylammonium fluoride, in the presence of an aprotic, polar solvent, such as dimethyl sulfoxide or N,N-dimethylacetamide. Carboxy protected in the form of organic silyloxycarbonyl, such as tri-lower alkylsilyloxycarbonyl, for example trimethylsilyloxycarbonyl, can be freed in customary manner by solvolysis, for example by treatment with water, an alcohol or an acid, or, furthermore, a fluoride, as described above. Esterified carboxy can also be freed enzymatically, for example by means of esterases or suitable peptidases, for example esterified arginine or lysine, such as lysine methyl ester, using trypsin.

A compound according to the invention which is obtainable by the process can be converted into another compound according to the invention in a manner known per se.

A compound according to the invention containing hydroxyl can be etherified by methods known per se. The etherification can be carried out, for example, using an alcohol, such as a substituted or unsubstituted lower alkanol, or a reactive ester thereof. Suitable reactive esters of the desired alcohols are, for example, those with strong inorganic or organic acids, such as corresponding halides, sulfates, lower alkanesulfonates or substituted or unsubstituted benzenesulfonates, for example chlorides, bromides, iodides, methane-, benzene- or p-toluenesulfonates. The etherification can be carried out, for example, in the presence of a base, an alkali metal hydride, hydroxide or carbonate, or of an amine. Conversely, corresponding ethers, such as lower alkoxy compounds, can be cleaved, for example, by means of strong acids, such as mineral acids, for example the hydrohalic acids hydrobromic or hydriodic acid, which may advantageously be present in the form of pyridinium halides, or by means of Lewis acids, for example halides of elements of main group III or the corresponding sub-groups. These reactions can be carried out, if necessary, with cooling or warming, for example in a temperature range from about −20° to about 100° C., in the presence or absence of a solvent or diluent, under inert gas and/or under pressure and, if appropriate, in a closed vessel.

Compounds of formula I in which $R_2$ is hydrogen can be N-alkylated in a manner known per se. The alkylation is carried out, for example, using a reactive ester of an lower alkyl halide, for example a bromide or iodide, lower alkylsulfonate, for example methanesulfonate or p-toluenesulfonate, or a di-lower alkyl sulfate, for example dimethyl sulfate, preferably under basic conditions, such as in the presence of sodium hydroxide solution or potassium hydroxide solution, and advantageously in the presence of a phase transfer catalyst, such as tetrabutylammonium bromide or benzyltrimethylammonium chloride, where, however, stronger basic condensing agents, such as alkali metal amides, hydrides or alkoxides, for example sodium amide, sodium hydride or sodium ethoxide, may be necessary. Furthermore, compounds of formula I in which $R_2$ is different from hydrogen, e.g. being lower alkyl, may be manufactured under reductive conditions, for example, using a suitable aldehyde. Corresponding compounds of formula I in which $R_2$ is hydrogen can also be acylated in a manner known per se, for example, following the acylation according to variant a).

Compounds of the formula I which contain an esterified or amidated carboxyl group as a substituent, a group of this type can be converted into a free carboxyl group, for example by means of hydrolysis, for example in the presence of a basic agent, or of an acidic agent, such as a mineral acid. Tert-butyloxycarbonyl, for example, can furthermore be converted into carboxyl, for example in a manner known per se, such as treating with trihaloacetic acid, such as trifluoroacetic acid.

The invention relates in particular to the processes described in the examples.

Salts of compounds of the formula I can be prepared in a manner known per se. Thus, for example, acid addition salts of compounds of the formula I are obtained by treating with an acid or a suitable ion exchange reagent. Salts can be converted into the free compounds in a customary manner, and acid addition salts can be converted, for example, by treating with a suitable basic agent.

Depending on the procedure and reaction conditions, the compounds according to the invention having salt-forming, in particular basic properties, can be obtained in free form or preferably in the form of salts.

In view of the close relationship between the novel compound in the free form and in the form of its salts, in the preceding text and below the free compound or its salts may correspondingly and advantageously also be understood as meaning the corresponding salts or the free compound.

The novel compounds including their salts of salt-forming compounds can also be obtained in the form of their hydrates or can include other solvents used for crystallization.

Depending on the choice of the starting materials and procedures, the novel compounds can be present in the form of one of the possible isomers or as mixtures thereof, for example as pure optical isomers, such as antipodes, or as isomer mixtures, such as racemates, diastereoisomer mixtures or racemate mixtures, depending on the number of asymmetric carbon atoms.

Acid addition salts can be prepared by neutralizing a compound of the formula (I) having a basic group with an acid or an acidic ion exchanger.

Salts with a base can be prepared by neutralizing a compound of the formula (I) having an acidic group with a base compound.

Racemates and diastereomer mixtures obtained can be separated into the pure isomers or racemates in a known manner on the basis of the physicochemical differences of the components, for example by fractional crystallization. Racemates obtained may furthermore be resolved into the optical antipodes by known methods, for example by recrystallization from an optically active solvent, chromatography on chiral adsorbents, with the aid of suitable microorganisms, by cleavage with specific immobilized enzymes, via the formation of inclusion compounds, for example using chiral crown ethers, only one enantiomer being complexed, or by conversion into diastereomeric salts, for example by reaction of a basic final substance racemate with an optically active acid, such as a carboxylic acid, for example tartaric or malic acid, or sulfonic acid, for example camphorsulfonic acid, and separation of the diastereomer mixture obtained in this manner, for example on the basis of its differing solubilities, into the diastereomers from which the desired enantiomer can be liberated by the action of suitable agents. The more active enantiomer is advantageously isolated.

The invention also relates to those embodiments of the process, according to which a compound obtainable as an intermediate in any step of the process is used as a starting material and the missing steps are carried out or a starting material in the form of a derivative or salt and/or its racemates or antipodes is used or, in particular, formed under the reaction conditions.

In the process of the present invention, those starting materials are preferably used which lead to the compounds described as particularly useful at the beginning. The invention likewise relates to novel starting materials which have been specifically developed for the preparation of the compounds according to the invention, to their use and to processes for their preparation. The invention especially relates to novel starting materials of formulae Ia, IIb, IIIa and IIIb wherein the variables have the meanings as indicated hereinbefore, their manufacture and use, e.g. as starting material.

The invention likewise relates to pharmaceutical preparations which contain the compounds according to the invention or pharmaceutically acceptable salts thereof as active ingredients, and to processes for their preparation.

The pharmaceutical preparations according to the invention which contain the compound according to the invention or pharmaceutically acceptable salts thereof are those for enteral, such as oral, furthermore rectal, and parenteral administration to (a) warm-blooded animal(s), the pharmacological active ingredient being present on its own or together with a pharmaceutically acceptable carrier. The daily dose of the active ingredient depends on the age and the individual condition and also on the manner of administration. The novel pharmaceutical preparations contain, for example, from about 10% to about 80%, preferably from about 20% to about 60%, of the active ingredient.

The pharmacologically active compounds of the invention can be used in the manufacture of pharmaceutical compositions that comprise an effective amount of the same on its own or in conjunction or admixture with excipients or carriers that are suitable for enteral or parenteral administration. Preferred are tablets and gelatin capsules that comprise the active constituent together with a) diluents, for example lactose, dextrose, sucrose, mannitol, sorbitol, cellulose and/or glycine, b) glidants, for example silica, talc, stearic acid, the magnesium or calcium salt thereof and/or polyethylene glycol, for tablets also c) binders, for example magnesium aluminum silicate, starch paste, gelatin, tragacanth, methylcellulose, sodium carboxymethylcellulose and/or polyvinylpyrrolidone, if desired d) dispersing or disintegrating agents, for example starches, agar, alginic acid or the sodium salt thereof, or foaming mixtures and/or e) absorbents, colouring agents, flavourings and sweeteners. Injectable preparations are preferably aqueous isotonic solutions or suspensions, and suppositories are advantageously produced from fatty emulsions or suspensions. These compositions may be sterilised and/or contain adjuvants, such as preservatives, stabilizers, wetting agents or emulsifiers, solubilisers, salts for regulating the osmotic pressure and/or buffers. In addition they may also contain other therapeutically valuable substances. These preparations are manufactured according to conventional mixing, granulating or coating methods and contain approximately from 0.1 to 100%, preferably approximately from 1 to 50%, of the active constituent. A unit dose for a mammal weighing approximately from 50 to 70 kg may contain between approximately 0.2 and 2000 mg, preferably between approximately 1 and 200 mg, of active constituent.

The following examples illustrate the invention described above; however, they are not intended to limit its extent in any manner. Temperatures are indicated in degrees Celsius.

WORKING EXAMPLES

Synthetic Intermediates

The following compounds are important synthetic intermediates:

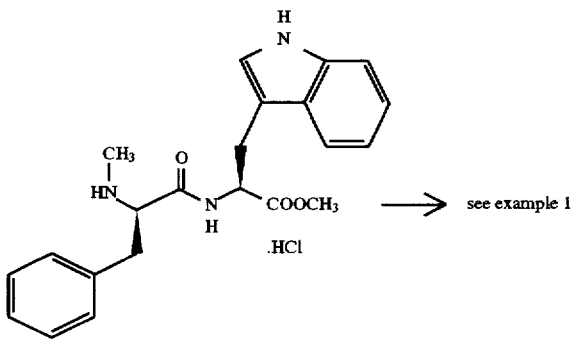 see example 1

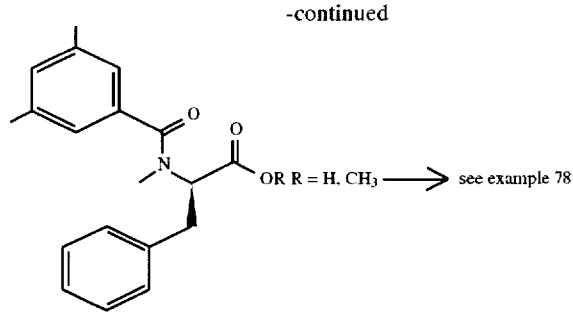  OR R = H, CH₃ ⟶ see example 78

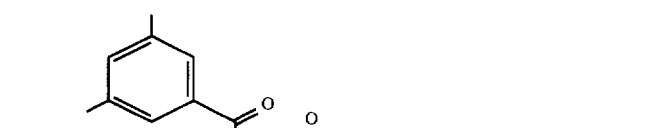  OR R = H, CH₃ ⟶ see example 55

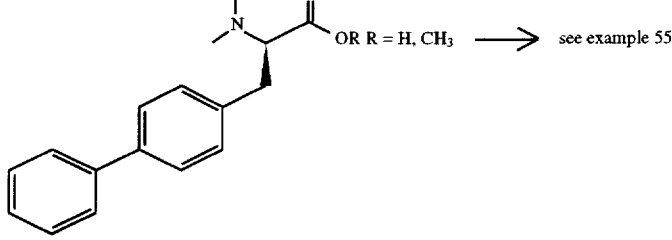  OR R = H, CH₃ ⟶ see example 91

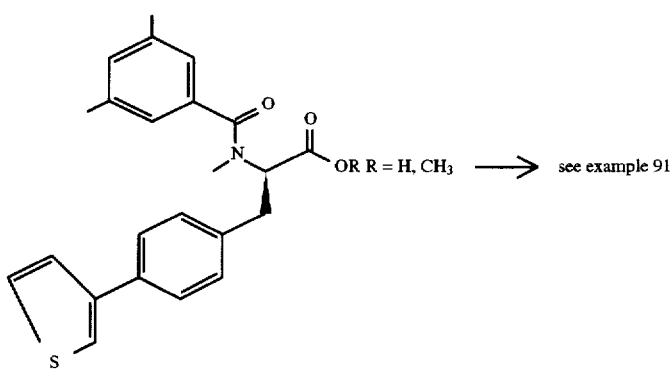  OR R = H, CH₃ ⟶ see example 95

Commercially not available 3-substituted alanine derivatives were synthesized according to Scheme II or according to M. J. O'Donnell, Tetrahedron Lett. 30, 2641 (1978).

Example 1
N-(3,5-Dimethylbenzoyl)-N-methyl-(D)-phenylalanyl-(L)-tryptophan

To a stirred solution of N-BOC-N-methyl-(D)-phenylalanine (2.1 g, 7.5 mmol) [BOC=tert-butyloxycarbonyl] in dry DMF [N,N-dimethylformamide] (15 ml) are added (L)-tryptophan methyl ester hydrochloride (2 g, 7.8 mmol) and hydroxybenztriazole (1.2 g, 8.8 mmol). The mixture is cooled to 0° and 1-(3-dimethylaminopropyl)-3-ethylcarbodiimide (1.7 ml, 9.2 mmol) is added dropwise. The reaction mixture is slowly warmed to r.t. (room temperature) and stirring continued for 2 hours. The homogeneous mixture is diluted with ethyl acetate (500 ml) and washed with three portions of water (200 ml). The organic layer is dried over magnesium sulfate, filtered and concentrated in vacuo to give N-BOC-N-methyl-(D)-phenylalanyl-(L)-tryptophan methyl ester as a white foam. $[\alpha]_D = +42°$ (c=1.0, ethanol).

The above crude material is dissolved in a mixture of trifluoroacetic acid (6 ml) and ethanedithiol (1.5 ml) and stirred under nitrogen at r.t. for 1 hour. A 4M solution of hydrogen chloride in dioxane (2 ml) is added. The hydrochloride salt is precipitated by addition of ether (400 ml) and hexane (200 ml), filtered and washed with ether to give N-methyl-(D)-phenylalanyl-(L)-tryptophan methyl ester hydrochloride (2.6 g) as a white powder. $|a|_D=-29°$ (c=1.0, ethanol).

A solution of the above hydrochloride salt (200 mg, 0.48 mmol) and 3,5-dimethylbenzoic acid (87 mg), 0.57 mmol) in DMF (1 ml) is treated with 1-(3-diniethylaminopropyl)-3-ethylcarbodiimide (0.11 ml, 0.6 mmol). The reaction mixture is slowly warmed to r.t. and stirring continued for 2 hours. The homogeneous mixture is diluted with ethyl acetate (100 ml) and washed with three portions of water (70 ml). The organic layer is dried over magnesium sulfate, filtered and concentrated in vacuo. Chromatography on silica with ethyl acetate/hexane 1:1 gives N-(3,5-dimethylbenzoyl)-N-methyl-(D)-phenylalanyl-(L)-tryptophan methyl ester as a white foam.

This material is hydrolized at 0° with lithium hydroxide (20 mg, 0.47 mmol) in MeOH/water 2:1 (9 ml). After 3 hours the reaction mixture is diluted with ether (200 ml) and washed with three portions of water (100 ml). The combined aqueous layers are acidified to pH=2 with 1M hydrochloric acid and extracted with two portions of ethyl acetate (200 ml). The ethyl acetate extracts are dried over magnesium sulfate, filtered and concentrated in vacuo to give the title compound as a white foam; m.p. 91°–94° C. FAB-MS m/e 498 (M+H)$^+$. $|a|_D=-46°$ (c=1.095, ethanol). HPLC (Chiralcel OD, hexane/isopropanol/TFA 900:100:3) ee>95%. NMR (CDCl$_3$, 400 MHz) d |ppm| 8.29 (s), 8.15 (s), 7.56 (d, J=7.8 Hz), 7.47 (d, J=7.8 Hz), 7.3–6.7 (m), 6.48 (s), 5.92 (s), 5.41 (dxd, J=6.8, 9.7 Hz), 4.84 (dxd, J=5.8, 13.2 Hz), 4.33 (dxd, J=2, 7.2 Hz), 3.4–2.75 (m), 2.70 (s), 2.18 (s), 1.91 (s).

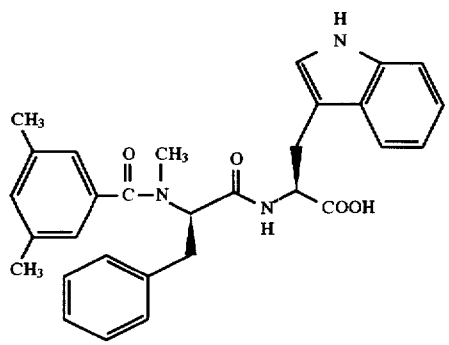

Example 2

Reduction of N-(3,5-dimethylbenzoyl)-N-methyl-(D)-phenylalanyl-(L)-tryptophan methylester (see example 1) with L-selectride |lithium tri-sec-butylborohydride| in dry THF |tetrahydrofuran| at 0° C. affords N-(3,5-dimethylbenzoyl)-N-methyl-(D)-phenylalanyl-(L)-tryptophanol as a colorless oil; FAB-MS m/e 484 (M+H)$^+$.

Example 3

Coupling of N-(3,5-dimethylbenzoyl)-N-methyl-(D)-phenylalanine (derived from the corresponding methylester described in example 78 by hydrolysis with lithium hydroxide in methanol/water: $|a|_D=+88°$ (c=1.0, ethanol)) with (L)-tryptophanamide hydrochloride according to example 12 gives N-(3,5-dimethylbenzoyl)-N-methyl-(D)-phenylalanyl-(L)-tryptophanamide: FAB-MS m/e 497 (M+H)$^+$.

Example 4

Coupling of N-(3,5-dimethylbenzoyl)-N-methyl-(D)-(4-phenyl)phenylalanine (see example 55) with (L)-tryptophanonitrile hydrochloride (see example 8) according to example 12 gives N-(3,5-dimethylbenzoyl)-N-methyl-(D)-(4-phenylphenyl )alanyl-(L)-tryptophanonitrile.

A solution of the above nitrile (100 mg, 0.18 mmol) in toluene (10 ml) is treated with tetrabutyltin azide (71 mg, 0.21 mmol) and refluxed for 4 hours under nitrogen. The cooled reaction mixture is treated with a mixture of dichloromethane (10 ml), methanol (6 ml) and ammonia (0.2 ml), stirred at r.t. for 30 minutes and concentrated. Chromatography of the crude material with a gradient of ethyl acetate/hexane/acetic acid 1:1:0.01 to ethyl acetate/acetic acid 1:0.01 gives 5-|N-(3,5-dimethylbenzoyl)-N-methyl-(D)-(4-phenylphenyl)alanyl-(L)-tryptophanyl|-1H-tetrazole as a colorless solid; FAB-MS m/e 598 (M+H)$^+$; mp 141°–143° C.

Example 5

N-(3,5-Dimethylbenzoyl)-trans-3-phenyl-(D)-prolinyl-(L)-tryptophan and N-(3,5-dimethylbenzoyl)-trans-3-phenyl-(L)-prolinyl-(L)-tryptophan A solution of trans-3-phenyl-(D,L)-proline methyl ester hydrochloride (2.0 g, 8.3 mmol) (J. Y. L. Chung et al, J. Org. Chem. 55, 270 (1990)) and 3,5-dimethylbenzoyl chloride (1.6 g, 9.5 mmol) in dichloromethane (20 ml) is treated with DMAP [dimethylaminopyridine] (2.4 g, 19.6 mmol). The reaction mixture is stirred at r.t. for 2 hours, diluted with dichloromethane (300 ml) and washed with three portions of water (200 ml). The organic layer is dried over magnesium sulfate, filtered and concentrated in vacuo. The crude material is chromatographed on silica with ethyl acetate/hexane 1:1 to give N-(3,5-dimethylbenzoyl)-3-phenyl-(D,L)-proline methyl ester as a mixture of trans and cis isomers.

This material is hydrolized at r.t. with 1M sodium hydroxide (6 ml) in THF (6 ml) to give N-(3,5-dimethylbenzoyl)-trans-3-phenyl-(D,L)-proline as a white foam. To a stirred solution of N-(3,5-dimethylbenzoyl)-trans-3-phenyl-(D,L)-proline (225 mg, 0.69 mmol) in dry DMF (2 ml) is added (L)-tryptophan methyl ester hydrochloride (180 mg, 0.7 mmol) and hydroxybenztriazole (115 mg, 0.85 mmol). The mixture is cooled to 0° and 1-(3-dimethylaminopropyl)-3-ethylcarbodiimide (0.15 ml, 0.85 mmol) is added dropwise. The reaction mixture is slowly warmed to r.t. and stirring continued overnight. The homogeneous mixture is diluted with ethyl acetate (100 ml) and washed with sodium bicarbonate (70 ml) and two portions of water (70 ml). The organic layer is dried over magnesium sulfate, filtered and concentrated in vacuo. The crude material is chromatographed on silica with ethyl acetate/hexane 1:1 to give 2 diastereomeric esters: N-(3,5-dimethylbenzoyl)-trans-3-phenyl-(D)-prolinyl-(L)-tryptophan methyl ester and N-(3,5-dimethylbenzoyl)-trans-3-phenyl-(L)-prolinyl-(L)-tryptophan methyl ester, each as a white foam.

Each of the above esters is hydrolized separately at 0° with 1M sodium hydroxide in methanol. The reaction mixtures was diluted with ether and washed with three portions of water. The combined aqueous layers are acidified to pH=2 with 1M hydrochloric acid and extracted with two portions of ethyl acetate. The ethyl acetate extracts are dried over

Example 6

N-(3,5-Dimethylbenzoyl)-N-methyl-(D)-(4-phenylphenyl)alanyl-(L)-tryptophan hydroxamic acid To a stirred solution of sodium methoxide (1.2 mmol) in dry methanol (5 ml) hydroxylamine hydrochloride is added at r.t. under nitrogen atmosphere. After 20 minutes stirring N-(3,5-dimethylbenzoyl)-N-methyl-(D)-(4-phenylphenyl) alanyl-(L)-tryptophan methyl ester (260 mg, 0.44 mmol; see example 55) is added. The reaction mixture is stirred for 3 hours, diluted with ether (100 ml) and washed with three portions of water (70 ml). The organic layer is dried over magnesium sulfate, filtered and concentrated in vacuo. Chromatography on silica with a gradient from ethyl acetate/hexane 1:2 to ethyl acetate only gives the title compound as a white foam. FAB-MS m/e 589 (M+H)$^+$.

Example 7

Coupling of N-(3,5-dimethylbenzoyl)-N-methyl-(D)-(4-phenylphenyl)alanine (example 55) with (D,L)-(3-benzo[b]thienyl)alanine methyl ester hydrochloride (P. N. Rao, Int. J. Peptide Protein Res. 29, 118 (1987)) followed by chromatographic separation of the 2 diastereomeric esters and hydrolysis of the methyl ester according to example 1 moieties gives N-(3,5-dimethylbenzoyl)-N-methyl-(D)-(4-phenylphenyl)alanyl-(D)-(3-benzo[b]thienyl)alanine, FAB-MS m/e 591 (M+H)$^+$, and N-(3,5-dimethylbenzoyl)-N-methyl-(D)-(4-phenylphenyl)alanyl-(L)-(3-benzo[b]thienyl) alanine, FAB-MS m/e 591 (M+H)$^+$.

Example 8

N-(3,5-Dimethylbenzoyl)-N-methyl-(D)-phenylalanyl-(L)-tryptophanonitrile

To a stirred solution of (L)-tryptophanamide hydrochloride (1 g, 4.2 mmol) and di-tert-butyl dicarbonate (1.1 g, 5 mmol) in dichloromethane (10 ml) triethylamine (0.7 ml, 5 mmol) is added dropwise. After 1 hour the reaction mixture is diluted with dichloromethane (200 ml) and washed with 1M hydrochloric acid (100 ml), saturated sodium bicarbonate solution (100 ml) and water (100 ml). The organic layer is dried over magnesium sulfate, filtered and concentrated in vacuo to give N-BOC-(L)-tryptophanamide.

The above crude material is dissolved in dichloromethane (40 ml) and treated with imidazole (0.4 g) and phosphorous oxychloride (0.4 ml). After stirring at r.t. overnight pyridine (4 ml) and more phosphorous oxychloride (0.4 ml) is added. After stirring 1 hour at r.t. the reaction mixture is diluted with dichloromethane (200 ml) and washed with three portions of 1M hydrochloric acid (100 ml). The organic layer is dried over magnesium sulfate, filtered and concentrated in vacuo. Chromatography on silica with ethyl acetate/hexane 1:2 gives N-BOC-(L)-tryptophanonitrile (0.5 g) as a white solid. The above material is dissolved in a mixture of trifluoroacetic acid (4 ml) and ethanedithiol (1 ml) and stirred under nitrogen at r.t. for 1 hour. A 4M solution of hydrogen chloride in dioxane (2 ml) is added. The hydrochloride is precipitated by addition of ether (400 ml) and hexane (200 ml), filtered and washed with ether to give (L)-tryptophanonitrile hydrochloride as a white solid.

To a stirred solution of N-(3,5-dimethylbenzoyl)-N-methyl-(D)-phenylalanine (200 mg, 0.64 mmol; derived from the corresponding methyl ester described in example 78 by hydrolysis with lithium hydroxide in methanol/water: |a|$_D$=+88° (c=1.0, ethanol)) in dry DMF (5 ml) is added the above (L)-tryptophanonitrile hydrochloride (120 mg, 0.65 mmol) and hydroxybenztriazole (90 mg, 0.66 mmol). The mixture is cooled to 0° and 1-(3-dimethylaminopropyl)-3-ethylcarbodiimide (0.13 ml, 0.68 mmol) is added dropwise. The reaction mixture is slowly warmed to r.t. and stirring continued for 2 hours. The homogeneous mixture is diluted with ethyl acetate (200 ml) and washed with three portions of water (100 ml). The organic layer is dried over magnesium sulfate, filtered and concentrated in vacuo. Chromatography on silica with ethyl acetate/hexane 2:3 gives the title compound as a slightly yellow foam. FAB-MS m/e 479 (M+H)$^+$.

Example 9

Coupling of N-(3,5-dimethylbenzoyl)-N-methyl-(D)-phenylalanine (derived from the corresponding methylester described in example 78 by hydrolysis with lithium hydroxide in methanol/water: |a|$_D$=+88° (c=1.0, ethanol)) with (L)-tryptamine hydrochloride according to example 12 gives N-(3,5-dimethylbenzoyl)-N-methyl-(D)-phenylalanyl-(L)-tryptamine. FAB-MS m/e 454 (M+H)$^+$.

Example 10

Following the procedure described in example 1 but starting from N-BOC-(D)-phenylalanine and (L)-tryptophan methyl ester hydrochloride gives N-(3,5-dimethylbenzoyl)-(D)-phenylalanyl-(L)-tryptophan; mp 95°–98° C.; |a|$_D$=+19° (c=0.465, ethanol). FAB-MS m/e 484 (M+H)$^+$.

Example 11

Following the procedure described in example 12 but starting from N-(3,5-dimethylbenzoyl)-(D)-phenylalanine and N-methyl-(L)-tryptophan methyl ester hydrochloride gives N-(3,5-dimethylbenzoyl)-(D)-phenylalanyl-N-methyl-(L)-tryptophan; FAB-MS m/e 498 (M+H)$^+$.

Example 12

N-(3,5-Dimethylbenzoyl)-N-methyl-(D)-(4-phenylphenyl)alanyl-N-methyl-(L)-tryptophan To a stirred solution of N-(3,5-dimethylbenzoyl)-N-methyl-(D)-(4-phenylphenyl)alanine (207 mg, 0.53 mmol; see example 55) in dry DMF (8 ml) is added N-methyl-(L)-tryptophan methyl ester hydrochloride (185 mg, 0.69 mmol) and hydroxybenztriazole (137 mg, 1.02 mmol). The mixture is cooled to 0° and 1-(3-dimethylaminopropyl)-3-ethylcarbodiimide (0.12 ml, 0.66 mmol) is added dropwise. The reaction mixture is slowly warmed to r.t. and stirring continued overnight. The homogeneous mixture is diluted with ethyl acetate (200 ml) and washed with three portions of water (100 ml). The organic layer is dried over magnesium sulfate, filtered and concentrated in vacuo. Chromatography on silica with ethyl acetate/hexane 1:3 gives N-(3, 5-dimethylbenzoyl)-N-methyl-(D)-(4-phenylphenyl)alanyl-N-methyl-(L)-tryptophan methyl ester as a white foam. This material is hydrolized at 0° with lithium hydroxide (5 mg, 0.12 mmol) in MeOH (0.6 ml) and water (0.3 ml). After 3 hours the reaction mixture is diluted with ether (100 ml) and washed with three portions of water (60 ml). The combined aqueous layers are acidified to pH=2 with 1M hydrochloric acid and extracted with two portions of ethyl acetate (100 ml). The ethyl acetate extracts are dried over magnesium sulfate, filtered and concentrated in vacuo to give the title compound as a white foam. |a|$_D$=−17° (c =0.96, methanol). FAB-MS m/e 588 (M+H)$^+$.

Example 13

Following the procedure described in example 12 and starting from N-(3,5-dimethylbenzoyl)-N-methyl-(D)-phenylalanine and N-methyl-(L)-tryptophan methyl ester hydrochloride gives N-(3,5-dimethylbenzoyl)-N-methyl-(D)-phenylalanyl-N-methyl-(L)-tryptophan; FAB-MS m/e 510 (M–H)$^-$.

Example 14

Following the procedure described in example 12 and starting from N-(3,5-dimethylbenzoyl)-N-(1-methylpropyl)-(D)-phenylalanine (prepared by reductive alkylation of (D)-phenylalanine methyl ester with ethylmethylketone in the presence of sodium cyanoborohydride followed by N-acylation with 3,5-dimethylbenzoyl chloride in the presence of DMAP and hydrolysis of the methyl ester moiety according to example 1 and (L)-tryptophan methyl ester hydrochloride gives N-(3,5-dimethylbenzoyl)-N-(1-methylpropyl)-(D)-phenylalanyl-(L)-tryptophan; FAB-MS m/e 540 (M+H)$^+$.

Example 15

Following the procedure described in example 12 and starting from N-(3,5-dimethylbenzoyl)-N-ethyl-(D)-phenylalanine (prepared by alkylation of N-(3,5-dimethylbenzoyl)-(D)-phenylalanine methyl ester with ethyl iodide in the presence of sodium hydride followed by hydrolysis of the methyl ester moiety according to example 1 and (L)-tryptophan methyl ester hydrochloride gives N-(3,5-dimethylbenzoyl)-N-ethyl-(D)-phenylalanyl-(L)-tryptophan; FAB-MS m/e 510 (M–H)$^-$.

Example 16

Following the procedure described in example 12 and starting from N-(3,5-dimethylbenzoyl)-N-(cyclohexylethyl)-(D)-phenylalanine (prepared by reductive alkylation of (D)-phenylalanine methyl ester with cyclohexanecarboxaldehyde in the presence of sodium cyanoborohydride followed by N-acylation with 3,5-dimethylbenzoyl chloride in the presence of DMAP and hydrolysis of the methyl ester moiety according to example 1 and (L)-tryptophan methyl ester hydrochloride gives N-(3,5-dimethylbenzoyl)-N-(cyclohexylmethyl)-(D)-phenylalanyl-(L)-tryptophan; FAB-MS m/e 580 (M+H)$^+$.

Example 17

Following the procedure described in example 12 and starting from N-(3,5-dimethylbenzoyl)-N-cyclohexyl-(D)-phenylalanine (prepared by reductive alkylation of (D)-phenylalanine methyl ester with cyclohexanone in the presence of sodium cyanoborohydride followed by N-acylation with 3,5-dimethylbenzoyl chloride in the presence of DMAP and hydrolysis of the methyl ester moiety according to example 1 and (L)-tryptophan methyl ester hydrochloride gives N-(3,5-dimethylbenzoyl)-N-cyclohexyl-(D)-phenylalanyl-(L)-tryptophan; FAB-MS m/e 566 (M+H)$^+$.

Example 18

Coupling of N-methyl-(D)-phenylalanyl-(L)-tryptophan methyl ester hydrochloride (see example 1) with acetic acid according to example 12 followed by hydrolysis of the methyl ester moiety according to example 1 gives N-acetyl-N-methyl-(D)-phenylalanyl-(L)-tryptophan; FAB-MS m/e 408 (M+H)$^+$.

Example 19

Coupling of N-methyl-(D)-phenylalanyl-(L)-tryptophan methyl ester hydrochloride (see example 1) with benzoic acid according to example 12 followed by hydrolysis of the methyl ester moiety according to example 1 gives N-benzoyl-N-methyl-(D)-phenylalanyl-(L)-tryptophan; FAB-MS m/e 470 (M+H)$^+$.

Example 20

Coupling of N-methyl-(D)-phenylalanyl-(L)-tryptophan methyl ester hydrochloride (see example 1) with trans-2-phenyl-1-cyclopropanecarboxylic acid according to example 12 followed by hydrolysis of the methyl ester moiety according to example 1 gives N-(trans-2-phenyl-1-cyclopropylcarbonyl)-N-methyl-(D)-phenylalanyl-(L)-tryptophan; FAB-MS m/e 510 (M+H)$^+$.

Example 21

Coupling of N-methyl-(D)-phenylalanyl-(L)-tryptophan methyl ester hydrochloride (see example 1) according to example 12 with 2-naphthoic acid followed by hydrolysis of the methyl ester moiety according to example 1 gives N-(2-naphthoyl)-N-methyl-(D)-phenylalanyl-(L)-tryptophan; FAB-MS m/e 520 (M+H)$^+$.

Example 22

Coupling of N-methyl-(D)-phenylalanyl-(L)-tryptophan methyl ester hydrochloride (see example 1) with p-toluic acid according to example 12 followed by hydrolysis of the methyl ester moiety according to example 1 gives N-(4-methylbenzoyl)-N-methyl-(D)-phenylalanyl-(L)-tryptophan; FAB-MS m/e 484 (M+H)$^+$.

Example 23

Coupling of N-methyl-(D)-phenylalanyl-(L)-tryptophan methyl ester hydrochloride (see example 1) with m-toluic acid according to example 12 followed by hydrolysis of the methyl ester moiety according to example 1 gives N-(3-methylbenzoyl)-N-methyl-(D)-phenylalanyl-(L)-tryptophan; FAB-MS m/e 484 (M+H)$^+$.

Example 24

Coupling of N-methyl-(D)-phenylalanyl-(L)-tryptophan methyl ester hydrochloride (see example 1) with 3,5-dichlorobenzoic acid according to example 12 followed by hydrolysis of the methyl ester moiety according to example 1 gives N-(3,5-dichlorobenzoyl)-N-methyl-(D)-phenylalanyl-(L)-tryptophan; FAB-MS m/e 538 (M+H)$^+$.

Example 25

Coupling of N-methyl-(D)-phenylalanyl-(L)-tryptophan methyl ester hydrochloride (see example 1) with 3,5-difluorobenzoic acid according to example 12 followed by hydrolysis of the methyl ester moiety according to example 1 gives N-(3,5-difluorobenzoyl)-N-methyl-(D)-phenylalanyl-(L)-tryptophan; FAB-MS m/e 506 (M+H)$^+$.

Example 26

Coupling of N-methyl-(D)-phenylalanyl-(L)-tryptophan methyl ester hydrochloride (see example 1) with 3,5-bis(trifluoromethyl)benzoic acid according to example 12 followed by hydrolysis of the methyl ester moiety according to example 1 gives N-[3,5-bis(trifluoromethyl)benzoyl]-N-methyl-(D)-phenylalanyl-(L)-tryptophan; FAB-MS m/e 606 (M+H)$^+$.

Example 27

Coupling of N-methyl-(D)-phenylalanyl-(L)-tryptophan methyl ester hydrochloride (see example 1) with 3,5-bis(trifluoromethyl)phenylacetic acid according to example 12 followed by hydrolysis of the methyl ester moiety according to example 1 gives N-[3,5-bis(trifluoromethyl)phenylacetyl]-N-methyl-(D)-phenylalanyl-(L)-tryptophan; FAB-MS m/e 620 (M+H)$^+$.

Example 28

Coupling of N-methyl-(D)-phenylalanyl-(L)-tryptophan methyl ester hydrochloride (see example 1) with 3-methyl-1-cyclohexanecarboxylic acid according to example 12 followed by hydrolysis of the methyl ester moiety according to example 1 gives N-(3-methyl-1-cyclohexylcarbonyl)-N-methyl-(D)-phenylalanyl-(L)-tryptophan; FAB-MS m/e 490 (M+H)$^+$.

Example 29

Coupling of N-methyl-(D)-phenylalanyl-(L)-tryptophan methyl ester hydrochloride (see example 1) with 3-methylvaleric acid according to example 12 followed by hydrolysis of the methyl ester moiety according to example 1 gives N-(3-methylvaleroyl)-N-methyl-(D)-phenylalanyl-(L)-tryptophan; FAB-MS m/e 464 (M+H)$^+$.

Example 30

Coupling of N-methyl-(D)-phenylalanyl-(L)-tryptophan methyl ester hydrochloride (see example 1) with 2-methylbutyric acid according to example 12 followed by hydrolysis of the methyl ester moiety according to example 1 gives N-(2-methylbutyroyl)-N-methyl-(D)-phenylalanyl-(L)-tryptophan; FAB-MS m/e 450 (M+H)$^+$.

Example 31

Coupling of N-methyl-(D)-phenylalanyl-(L)-tryptophan methyl ester hydrochloride (see example 1) with 3,5-dihydroxybenzoic acid followed according to example 12 by hydrolysis of the methyl ester moiety according to example 1 gives N-(3,5-dihydroxybenzoyl)-N-methyl-(D)-phenylalanyl-(L)-tryptophan; FAB-MS m/e 502 (M+H)$^+$.

Example 32

Coupling of N-methyl-(D)-phenylalanyl-(L)-tryptophan methyl ester hydrochloride (see example 1) with 2,5-dihydroxybenzoic acid according to example 12 followed by hydrolysis of the methyl ester moiety according to example 1 gives N-(2,5-dihydroxybenzoyl)-N-methyl-(D)-phenylalanyl-(L)-tryptophan; FAB-MS m/e 502 (M+H)$^+$.

Example 33

Coupling of N-methyl-(D)-phenylalanyl-(L)-tryptophan methyl ester hydrochloride (see example 1) with 2-thiophenecarboxylic acid according to example 12 followed by hydrolysis of the methyl ester moiety according to example 1 gives N-(2-thiophenecarbonyl)-N-methyl-(D)-phenylalanyl-(L)-tryptophan; FAB-MS m/e 474 (M–H)$^-$.

Example 34

Coupling of N-methyl-(D)-phenylalanyl-(L)-tryptophan methyl ester hydrochloride (see example 1) with 5-methyl-2-thiophenecarboxylic acid according to example 12 followed by hydrolysis of the methyl ester moiety according to example 1 gives N-(5-methyl-2-thiophenecarbonyl)-N-methyl-(D)-phenylalanyl-(L)-tryptophan; FAB-MS m/e 488 (M–H)$^-$.

Example 35

Coupling of N-methyl-(D)-phenylalanyl-(L)-tryptophan methyl ester hydrochloride (see example 1) with 3-methyl-2-thiophenecarboxylic acid according to example 12 followed by hydrolysis of the methyl ester moiety according to example 1 gives N-(3-methyl-2-thiophenecarbonyl)-N-methyl-(D)-phenylalanyl-(L)-tryptophan; FAB-MS m/e 488 (M–H)$^-$.

Example 36

Coupling of N-methyl-(D)-phenylalanyl-(L)-tryptophan methyl ester hydrochloride (see example 1) with 4-phenylbenzoic acid according to example 12 followed by hydrolysis of the methyl ester moiety according to example 1 gives N-(4-phenylbenzoyl)-N-methyl-(D)-phenylalanyl-(L)-tryptophan; FAB-MS m/e 546 (M+H)$^+$.

Example 37

Coupling of N-methyl-(D)-phenylalanyl-(L)-tryptophan methyl ester hydrochloride (see example 1) with 3,5-dimethoxybenzoic acid according to example 12 followed by hydrolysis of the methyl ester moiety according to example 1 gives N-(3,5-dimethoxybenzoyl)-N-methyl-(D)-phenylalanyl-(L)-tryptophan; FAB-MS m/e 530 (M+H)$^+$.

Example 38

Coupling of N-methyl-(D)-phenylalanyl-(L)-tryptophan methyl ester hydrochloride (see example 1) with 4-methoxybenzoic acid according to example 12 followed by hydrolysis of the methyl ester moiety according to example 1 gives N-(4-methoxybenzoyl)-N-methyl-(D)-phenylalanyl-(L)-tryptophan; FAB-MS m/e 500 (M+H)$^+$.

Example 39

Coupling of N-methyl-(D)-phenylalanyl-(L)-tryptophan methyl ester hydrochloride (see example 1) with 2-methoxybenzoic acid according to example 12 followed by hydrolysis of the methyl ester moiety according to example 1 gives N-(2-methoxybenzoyl)-N-methyl-(D)-phenylalanyl-(L)-tryptophan; FAB-MS m/e 498 (M–H)$^-$.

Example 40

Coupling of N-methyl-(D)-phenylalanyl-(L)-tryptophan methyl ester hydrochloride (see example 1) with 3,5-dinitrobenzoic acid according to example 12 followed by hydrolysis of the methyl ester moiety according to example 1 gives N-(3,5-dinitrobenzoyl)-N-methyl-(D)-phenylalanyl-(L)-tryptophan; FAB-MS m/e 558 (M–H)$^-$.

Example 41

Coupling of N-methyl-(D)-phenylalanyl-(L)-tryptophan methyl ester hydrochloride (see example 1) with 3,5-dibromobenzoic acid according to example 12 followed by hydrolysis of the methyl ester moiety according to example 1 gives N-(3,5-dibromobenzoyl)-N-methyl-(D)-phenylalanyl-(L)-tryptophan; FAB-MS m/e 626 (M+H)$^+$.

Example 42

Coupling of N-methyl-(D)-phenylalanyl-L)-tryptophan methyl ester hydrochloride (see example 1) with 3-methoxybenzoic acid according to example 12 followed by hydrolysis of the methyl ester moiety according to example 1 gives N-(3-methoxybenzoyl)-N-methyl-(D)-phenylalanyl-(L)-tryptophan; FAB-MS m/e 500 (M+H)⁺.

Example 43

Coupling of N-methyl-(D)-phenylalanyl-(L)-tryptophan methyl ester hydrochloride (see example 1) with isonicotinic acid according to example 12 followed by hydrolysis of the methyl ester moiety according to example 1 gives N-(4-pyridylcarbonyl)-N-methyl-(D)phenylalanyl-(L)-tryptophan; FAB-MS m/e 471 (M+H)⁺.

Example 44

Coupling of N-methyl-(D)-phenylalanyl-(L)-tryptophan methyl ester hydrochloride (see example 1) with 6-chloro-2-pyridinecarboxylic acid according to example 12 followed by hydrolysis of the methyl ester moiety according to example 1 gives N-(6-chloro-2-pyridylcarbonyl)-N-methyl-(D)-phenylalanyl-(L)-tryptophan; FAB-MS m/e 503 (M–H)⁻.

Example 45

Reaction of N-methyl-(D)-phenylalanyl-(L)-tryptophan methyl ester hydrochloride (see example 1) with isopropyl chloroformate in the presence of triethylamine followed by hydrolysis of the methyl ester moiety according to example 1 gives N-isopropoxycarbonyl-N-methyl-(D)-phenylalanyl-(L)-tryptophan; FAB-MS m/e 452 (M+H)⁺.

Example 46

Coupling of N-(3,5-dimethylbenzoyl)-N-methyl-(L)-isoleucine (prepared following the procedure described in example 78) with (L)-tryptophan methyl ester hydrochloride according to example 12 followed by hydrolysis of the methyl ester moiety according to example 1 gives N-(3,5-dimethylbenzoyl)-N-methyl-(L)-isoleucinyl-(L)-tryptophan; FAB-MS m/e 464 (M+H)⁺.

Example 47

Coupling of N-(3,5-dimethylbenzoyl)-N-methyl-(D.L)-(3,5-dimethylphenyl)alanine (prepared from 3,5-dimethylbenzyl bromide according to the general method A according to scheme II) with (L)-tryptophan methyl ester hydrochloride according to example 12 followed by hydrolysis of the methyl ester moiety according to example 1 gives N-(3,5-dimethylbenzoyl)-N-methyl-(D.L)-(3,5-dimethylphenyl)alanyl-(L)-tryptophan as a mixture of 2 diastereomers; FAB-MS m/e 524 (M–H)⁻.

Example 48

Coupling of N-(3,5-dimethylbenzoyl)-N-methyl-(D.L)-cyclohexylalanine (prepared from bromomethylcyclohexane according to the general method A according to Scheme II) with (L)-tryptophan methyl ester hydrochloride according to example 12 followed by hydrolysis of the methyl ester moiety according to example 1 gives N-(3,5-dimethylbenzoyl)-N-methyl-(D.L)-cyclohexylalanyl-(L)-tryptophan as a mixture of 2 diastereomers; FAB-MS m/e 504 (M+H)⁺.

Example 49

Coupling of N-(3,5-dimethylbenzoyl)-N-methyl-(D.L)-cyclohexylglycine (prepared from bromocyclohexane according to the general method A according to Scheme II) with (L)-tryptophan methyl ester hydrochloride according to example 12 followed by hydrolysis of the methyl ester moiety according to example 1 gives N-(3,5-dimethylbenzoyl)-N-methyl-(D.L)-cyclohexylglycyl-(L)-tryptophan as a mixture of 2 diastereomers; FAB-MS m/e 488 (M–H)⁻.

Example 50

Coupling of N-(3,5-dimethylbenzoyl)-N-methyl-(D)-(2-naphthyl)alanine (prepared from (D)-(2-naphthyl)alanine according to example 55) with (L)-tryptophan methyl ester hydrochloride according to example 12 followed by hydrolysis of the methyl ester moiety according to example 1 gives N-(3,5-dimethylbenzoyl)-N-methyl-(D)-(2-naphthyl)alanyl-(L)-tryptophan; FAB-MS m/e 546 (M–H)⁻.

Example 51

Coupling of N-(3,5-dimethylbenzoyl)-N-methyl-(D.L)-phenylglycine (prepared from benzyl bromide according to the general method A according to Scheme II) with (L)-tryptophan methyl ester hydrochloride according to example 12 followed by hydrolysis of the methyl ester moiety according to example 1 gives N-(3,5-dimethylbenzoyl)-N-methyl-(D.L)-phenylglycyl-(L)-tryptophan as a mixture of 2 diastereomers; FAB-MS m/e 484 (M+H)⁺.

Example 52

To a solution of 2-(hydroxymethyl)thiophene (5.7 g, 49.9 mmol) and carbon tetrabromide (24.8 g, 74.9 mmol) in THF (85 ml) is added triphenylphosphine (19.6 g, 74.9 mmol) at 0° C. The mixture is stirred at r.t. for 3 hrs., diluted with diethyl ether, and filtered with celite. The filtrate is concentrated in vacuo, diluted again with diethyl ether and filtered. The filtrate is condensed in vacuo to give 2-bromomethyl thiophene. Coupling of N-(3,5-dimethylbenzoyl)-N-methyl-(D.L)-(2-thienyl)alanine (prepared from 2-(bromomethyl) thiophene according to the general method A according to Scheme II) with (L)-tryptophan methyl ester according to example 12 hydrochloride followed by hydrolysis of the methyl ester moiety according to example 1 gives N-(3,5-dimethylbenzoyl)-N-methyl-(D.L)-(2-thienyl)alanyl-(L)-tryptophan as a mixture of 2 diastereomers; FAB-MS m/e 504 (M+H)⁺.

Example 53

Coupling of N-(3,5-dimethylbenzoyl)-N-methyl-(D.L)-(3-furyl)alanine [prepared from 3-(bromomethyl)furane (from 3-(hydroxymethyl)furane according to the procedure described in example 52) according to the general method B according to Scheme III] with (L)-tryptophan methyl ester hydrochloride according to example 12 followed by hydrolysis of the methyl ester moiety according to example 1 gives N-(3,5-dimethylbenzoyl)-N-methyl-(D.L)-(3-furyl)alanyl-(L)-tryptophan as a mixture of 2 diastereomers; FAB-MS m/e 488 (M+H)⁺.

Example 54

Coupling of N-(3,5-dimethylbenzoyl)-N-methyl-(D.L)-(2-pyridyl)alanine (prepared from commercially available 2-(chloromethyl)pyridine according to the general method A according to Scheme II) with (L)-tryptophan methyl ester hydrochloride according to example 12 followed by hydrolysis of the methyl ester moiety according to example 1 gives N-(3,5-dimethylbenzoyl)-N-methyl-(D.L)-(2-

41 pyridyl)alanyl-(L)-tryptophan as a mixture of 2 diastereomers; FAB-MS m/e 499 (M+H)⁺.

Example 55

N-(3,5-Dimethylbenzoyl)-N-methyl-(D)-(4-phenylphenyl)alanyl-(L)-tryptophan

A solution of thionylchloride (6.5 ml) in dry methanol (280 ml) at -20° C. is treated with (D)-(4-phenylphenyl) alanine (3.7 g, 13.3 mmol) (Y. Yabe et al., Chem. Phaem. Bull. 24(12), 3149 (1976)). The reaction mixture is refluxed overnight and concentrated in vacuo. Recrystallization from methanol/ether gives (D)-(4-phenylphenyl)alanine methyl ester hydrochloride; |a|$_D$=+13° (c=1.025, methanol).

A solution of the above material (315 mg, 0.94 mmol) in dry THF (0.4 ml) is treated at r.t. with water (0.4 ml), formalin (0.15 ml, 1.88 mmol) and freshly distilled cyclopentadiene (0.3 ml, 3.63 mmol). The slightly yellow solution is stirred at r.t. for 2 hours, washed with hexane (100 ml), diluted with 4% sodium bicarbonate solution (100 ml) and extracted with chloroform (200 ml). The organic layer is dried over magnesium sulfate, filtered and concentrated in vacuo to give a bicyclic intermediate (0.39 g). This material is dissolved at r.t. under nitrogen atmosphere in chloroform (4.7 ml) and treated with trifluoroacetic acid (4.7 ml) and triethylsilane (0.45 ml). The solution is stirred for 20 hours and concentrated in vacuo. The crude product is dissolved in ethyl acetate (200 ml) and washed with 1M hydrochloric acid (100 ml) and saturated sodium bicarbonate solution (100 ml). The organic layer is dried over magnesium sulfate, filtered and concentrated in vacuo to give N-methyl-(D)-(4-phenylphenyl)alanine as a white foam.

A solution of the above material in chloroform (5 ml) is treated with 2M sodium carbonate (0.6 ml) and 3,5-dimethylbenzoyl chloride (0.3 ml, 1.4 mmol). The reaction mixture is stirred at r.t. for 2.5 hours, diluted with ethyl acetate (200 ml) and washed with 4% sodium bicarbonate solution (100 ml), water (100 ml), 1 M hydrochloric acid (100 ml) and again water (100 ml). The organic layer is dried over magnesium sulfate, filtered and concentrated in vacuo. Chromatography on silica with ethyl acetate/hexane 4:1 gives N-(3,5-dimethylbenzoyl)-N-methyl-(D)-(4-phenylphenyl)alanine methyl ester; |a|$_D$=+48° (c=0.685, methanol); ee>98% (HPLC: Chiralcel OF).

This material (110 mg, 0.27 mmol) is hydrolized at 0° with lithium hydroxide (13 mg, 0.31 mmol) in MeOH (0.8 ml), water (0.4 ml) and THF (0.4 ml). After 2 hours the reaction mixture is diluted with ether (200 ml) and washed with three portions of water (100 ml). The combined aqueous layers are acidified to pH=2 with 1M hydrochloric acid and extracted with two portions of ethyl acetate (200 ml). The ethyl acetate extracts are dried over magnesium sulfate, filtered and concentrated in vacuo to give N-(3,5-dimethylbenzoyl)-N-methyl-(D)-(4-phenylphenyl)alanine as a white foam; |a|$_D$=+7.5° (c=1.0, methanol).

A solution of the above material (103 mg, 0.27 mmol), (L)-tryptophan methyl ester hydrochloride (100 mg), 0.39 mmol) and hydroxybenztriazole (70 mg, 0.52 mmol) in dry DMF (3 ml) is treated with 1-(3-dimethylaminopropyl)-3-ethylcarbodiimide (0.07 ml, 0.38 mmol). The reaction mixture is slowly warmed to r.t. and stirring continued overnight. The homogeneous mixture is diluted with ethyl acetate (100 ml) and washed with three portions of water (70 ml). The organic layer is dried over magnesium sulfate, filtered and concentrated in vacuo. Chromatography on silica with ethyl acetate/hexane 1:1 gives N-(3,5-dimethylbenzoyl)-N-methyl-(D)-(4-phenylphenyl)alanyl-

42

(L)-tryptophan methyl ester as a white foam; de>98% (HPLC: Chiralcel OD).

This material is hydrolized at 0° with lithium hydroxide (10 mg, 0.23 mmol) in MeOH |Methanol| (2 ml), THF (1 ml) and water (1 ml). After 3 hours the reaction mixture is diluted with ether (100 ml) and washed with three portions of water (60 ml). The combined aqueous layers are acidified to pH=2 with 1M hydrochloric acid and extracted with two portions of ethyl acetate (100 ml). The ethyl acetate extracts are dried over magnesium sulfate, filtered and concentrated in vacuo to give the title compound as a white foam; FAB-MS m/e 574 (M+H)⁺; |a|$_D$=+2.5° (c=1.0, ethanol); NMR (CDCl₃, 400 MHz) d |ppm| 8.32 (s), 8.22 (s), 7.6–6.8 (m), 6.93 (s), 6.8 (m), 6.51 (s), 5.97 (t, J=8 Hz), 4.85 (q, J=6 Hz), 4.36 (m), 3.4–2.8 (m), 2.73 (s), 2.15 (s), 1.85 (s).

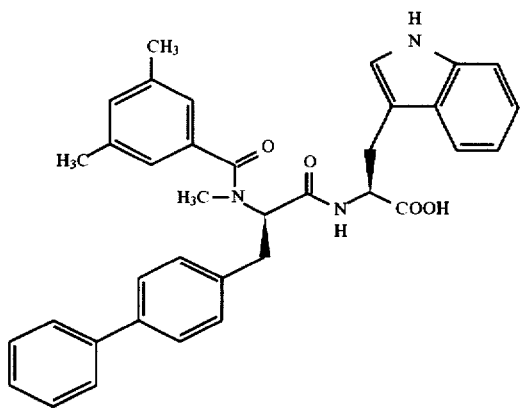

Example 56

A mixture of 3-methylbiphenyl (5.23 g, 31.1 mmol), N-bromosuccinimide (5.56 g, 31.2 mmol), benzoyl peroxide (135 mg, 0.56 mmol), and carbon tetrachloride (150 ml) is refluxed for 17 h. The mixture is concentrated in vacuo and the residue is purified by flash column chromatography (hexane) to give 3-phenylbenzyl bromide.

Coupling of N-(3,5-dimethylbenzoyl)-N-methyl-(D,L)-(3-phenylphenyl)alanine (prepared from 3-phenylbenzyl bromide according to the general method B according to Scheme III) with (L)-tryptophan methyl ester hydrochloride according to example 12 followed by hydrolysis of the methyl ester moiety according to example 1 gives N-(3,5-dimethylbenzoyl)-N-methyl-(D,L)-(3-phenylphenyl)alanyl-(L)-tryptophan as a mixture of 2 diastereomers; FAB-MS m/e 574 (M+H)⁺.

Example 57

Coupling of N-(3,5-dimethylbenzoyl)-N-methyl-(D,L)-3-(diphenyl)alanine (prepared from commercially available diphenylbromomethane according to the general method B according to Scheme III) with (L)-tryptophan methyl ester hydrochloride according to example 12 followed by hydrolysis of the methyl ester moiety according to example 1 gives N-(3,5-dimethylbenzoyl)-N-methyl-(D,L)-3-(diphenyl)alanyl-(L)-tryptophan as a mixture of 2 diastereomers; FAB-MS m/e 572 (M–H)⁻.

Example 58

Coupling of N-(3,5-dimethylbenzoyl)-N-methyl-(D,L)-(4-quinolyl)alanine |prepared from 4-(bromomethyl) quinoline (from 4-(hydroxymethyl)quinoline according to the procedure described in example 52) according to the general method B according to Scheme III] with (L)-tryptophan methyl ester hydrochloride according to example 12 followed by hydrolysis of the methyl ester moiety according to example 1 gives N-(3,5-dimethylbenzoyl)-N-methyl-(D,L)-(4-quinolyl)alanyl-(L)-tryptophan as a mixture of 2 diastereomers; FAB-MS m/e 547 (M−H)⁻.

Example 59

Coupling of N-(3,5-dimethylbenzoyl)-N-methyl-(D,L)-(2-chlorophenyl)alanine (prepared from commercially available 2-chlorobenzyl bromide according to the general method B according to Scheme III) with (L)-tryptophan methyl ester hydrochloride according to example 1 followed by hydrolysis of the methyl ester moiety according to example 12 gives N-(3,5-dimethylbenzoyl)-N-methyl-(D,L)-(2-chlorophenyl)alanyl-(L)-tryptophan as a mixture of 2 diastereomers; FAB-MS m/e 530 (M−H)⁻.

Example 60

Coupling of N-(3,5-dimethylbenzoyl)-N-methyl-(D,L)-(3-chlorophenyl)alanine (prepared from commercially available 3-chlorobenzyl bromide according to the general method B according to Scheme III) with (L)-tryptophan methyl ester hydrochloride according to example 1 followed by hydrolysis of the methyl ester moiety according to example 12 gives N-(3,5-dimethylbenzoyl)-N-methyl-(D,L)-(3-chlorophenyl)alanyl -(L)-tryptophan as a mixture of 2 diastereomers; FAB-MS m/e 532 (M+H)⁺.

Example 61

Coupling of N-(3,5-dimethylbenzoyl)-N-methyl-(D,L)-(4-chlorophenyl)alanine (prepared from commercially available 4-chlorobenzyl chloride according to the general method A according to Scheme II) with (L)-tryptophan methyl ester hydrochloride according to example 1 followed by hydrolysis of the methyl ester moiety according to example 12 gives N-(3,5-dimethylbenzoyl)-N-methyl-(D,L)-(4-chlorophenyl)alanyl-(L)-tryptophan as a mixture of 2 diastereomers; FAB-MS m/e 530 (M−H)⁻.

Example 62

Coupling of N-(3,5-dimethylbenzoyl)-N-methyl-(D,L)-[4-(2-pyridyl)phenyl]alanine [prepared from 4-(2-pyridyl)benzyl bromide (from 4-(2-pyridyl)toluene according to the procedure described in example 56) according to the general method B according to Scheme III] with (L)-tryptophan methyl ester hydrochloride according to example 1 followed by hydrolysis of the methyl ester moiety according to example 12 gives N-(3,5-dimethylbenzoyl)-N-methyl-(D,L)-[4-(2-pyridyl)phenyl]alanyl-(L)-tryptophan as a mixture of 2 diastereomers; FAB-MS m/e 575 (M+H)⁺.

Example 63

Coupling of N-(3,5-dimethylbenzoyl)-N-methyl-(D,L)-(3-phenyl-prop-1-yl)glycine (prepared from commercially available 1-bromo-3-phenylpropane according to the general method B according to Scheme III) with (L)-tryptophan methyl ester hydrochloride according to example 1 followed by hydrolysis of the methyl ester moiety according to example 12 gives N-(3,5-dimethylbenzoyl)-N-methyl-(D,L)-(3-phenyl-prop-1-yl)-glycyl-(L)-tryptophan as a mixture of 2 diastereomers; FAB-MS m/e 524 (M−H)⁻.

Example 64

Coupling of N-(3,5-dimethylbenzoyl)-N-methyl-(D)-tyrosine (prepared from (D)-tyrosine following the procedure described in example 55) with (L)-tryptophan methyl ester hydrochloride according to example 1 followed by hydrolysis of the methyl ester moiety according to example 12 gives N-(3,5-dimethylbenzoyl)-N-methyl-(D)-tyrosyl-(L)-tryptophan; FAB-MS m/e 512 (M−H)⁻.

Example 65

Coupling of N-(3,5-dimethylbenzoyl)-N-methyl-O-methyl-(D)-tyrosine (prepared by O-methylation of N-(3,5-dimethylbenzoyl)-N-methyl-(D)-tyrosine (example 64)) with (L)-tryptophan methyl ester hydrochloride according to example 1 followed by hydrolysis of the methyl ester moiety according to example 12 gives N-(3,5-dimethylbenzoyl)-N-methyl-O-methyl-(D)-tyrosyl-(L)-tryptophan; FAB-MS m/e 528 (M+H)⁺.

Example 66

Coupling of N-(3,5-dimethylbenzoyl)-N-methyl-O-benzyl-(D)-tyrosine (prepared by O-benzylation of N-(3,5-dimethylbenzoyl)-N-methyl-(D)-tyrosine (example 64)) with (L)-tryptophan methyl ester hydrochloride according to example 1 followed by hydrolysis of the methyl ester moiety according to example 12 gives N-(3,5-dimethylbenzoyl)-N-methyl-O-benzyl-(D)-tyrosyl-(L)-tryptophan; FAB-MS m/e 602 (M−H)⁻.

Example 67

Coupling of N-(3,5-dimethylbenzoyl)-N-methyl-(D)-phenylalanine (derived from the corresponding methylester described in example 78 by hydrolysis with lithium hydroxide in methanol/water; $[\alpha]_D$=+88° (c=1.0, ethanol)) with (L)-phenylalanine methyl ester hydrochloride according to example 1 followed by hydrolysis of the methyl ester moiety according to example 12 gives N-(3,5-dimethylbenzoyl)-N-methyl-(D)-phenylalanyl-(L)-phenylalanine; FAB-MS m/e 457 (M−H)⁻.

Example 68

Coupling of N-(3,5-dimethylbenzoyl)-N-methyl-(D)-phenylalanine (derived from the corresponding methylester described in example 78 by hydrolysis with lithium hydroxide in methanol/water; $[\alpha]_D$=+88° (c=1.0, ethanol)) with (L)-(1-naphthyl)alanine methyl ester hydrochloride according to example 1 followed by hydrolysis of the methyl ester moiety according to example 12 gives N-(3,5-dimethylbenzoyl)-N-methyl-(D)-phenylalanyl-(L)-(1-naphthyl)alanine; FAB-MS m/e 509 (M+H)⁺.

Example 69

Coupling of N-(3,5-dimethylbenzoyl)-N-methyl-(D)-(4-phenylphenyl)alanine (example 55) with (L)-(1-naphthyl)alanine methyl ester hydrochloride followed by hydrolysis of the methyl ester moiety gives N-(3,5-dimethylbenzoyl)-N-methyl-(D)-(4-phenylphenyl)-alanyl-(L)-(1-naphthyl)alanine; FAB-MS m/e 585 (M+H)⁺.

Example 70

Coupling of N-(3,5-dimethylbenzoyl)-N-methyl-(D)-phenylalanine (derived from the corresponding methylester described in example 78 by hydrolysis with lithium hydroxide in methanol/water; $[\alpha]_D$=+88° (c=1.0, ethanol)) with (L)-(2-naphthyl)alanine methyl ester hydrochloride followed by hydrolysis of the methyl ester moiety gives N-(3,5-dimethylbenzoyl)-N-methyl-(D)-phenylalanyl-(L)-(2-naphthyl)alanine; FAB-MS m/e 509 (M+H)⁺.

Example 71

Coupling of N-(3,5-dimethylbenzoyl)-N-methyl-(D)-phenylalanine (derived from the corresponding methylester described in example 78 by hydrolysis with lithium hydroxide in methanol/water: $|a|_D=+88°$ (c=1.0, ethanol)) with (L)-homo-phenylalanine methyl ester hydrochloride according to example 1 followed by hydrolysis of the methyl ester moiety according to example 12 gives N-(3,5-dimethylbenzoyl)-N-methyl-(D)-phenylalanyl-(L)-homo-phenylalanine; FAB-MS m/e 473 (M+H)⁺.

Example 72

Coupling of N-(3,5-dimethylbenzoyl)-N-methyl-(D)-phenylalanine (derived from the corresponding methylester described in example 78 by hydrolysis with lithium hydroxide in methanol/water: $|a|_D=+88°$ (c=1.0, ethanol)) with (D,L)-Nind-methyltryptophan methyl ester hydrochloride followed by hydrolysis of the methyl ester moiety gives N-(3,5-dimethylbenzoyl)-N-methyl-(D)-phenylalanyl-(D,L)-Nind-methyltryptophan as a mixture of 2 diastereomers; FAB-MS m/e 512 (M+H)⁺.

Example 73

3-|N-|N-(3,5-Dimethylbenzoyl)-N-methyl-(D)-phenylalanyl|(2-aminoethyl)|indole-4-carboxylic acid Synthesis of methyl 3-(2-aminoethyl)indole-4-carboxylate A solution of methyl indole-4-carboxylate (1.1 g 6.2 mmol) and Eschenmoser's salt |N,N-dimethylmethyleneammonium iodide| (1.3 g, 7 mmol) in acetonitrile (15 ml) is refluxed for 3 hours. The reaction mixture is concentrated, redisolved in dichloromethane (400 ml) and washed with 1M sodium hydroxide (200 ml) and water (200 ml). The organic layer is dried over magnesium sulfate, filtered and concentrated. The resulting methyl 3-(dimethylaminomethyl)indole-4-carboxylate (1.2 g) is methylated with methyl iodide (0.7 ml) in a mixture of dichoromethane (25 ml) and ether (13 ml). The reaction mixture is concentrated, the product dissolved in DMSO (7 ml) and treated with potassium cyanide (700 mg, 10 mmol). After stirring at r.t. overnight the reaction mixture is diluted with ethyl acetate (200 ml) and washed with three portions of water (100 ml). The organic layer is dried over magnesium sulfate, filtered and concentrated in vacuo. The crude material is chromatographed on silica with ethyl acetate/hexane 2:3 to give methyl 3-(cyanomethyl)indole-4-carboxylate as a dark oil. Hydrogenation in acetic acid over platinum oxide gives the desired intermediate as an orange solid.

Coupling

A solution of the above methyl 3-(2-aminoethyl)indole-4-carboxylate (50 mg, 0.23 mmol), hydroxybenztriazole (37 mg, 0.27 mmol) and N-(3,5-dimethylbenzoyl)-N-methyl-(D)-phenylalanine (70 ml, 0.23 mmol; derived from the corresponding methyl ester described in example 78 by hydrolysis with lithium hydroxide: $|a|_D+88°$ (c=1.0, ethanol)) in DMF (1 ml) at 0° C. is treated with 1-(3-dimethylaminopropyl)-3-ethylcarbodiimide (0.05 ml, 0.27 mmol). The reaction mixture is slowly warmed to r.t. and stirring continued for 2 hours. The homogeneous mixture is diluted with ethyl acetate (100 ml) and washed with three portions of water (70 ml). The organic layer is dried over magnesium sulfate, filtered and concentrated in vacuo. The crude material is chromatographed on silica with ethyl acetate/hexane 1:1 to give methyl 3-N-|N-(3,5-dimethylbenzoyl)-N-methyl-(D)-phenylalanyl|(2-aminoethyl)indole-4-carboxylate as a white foam. This material is hydrolized at r.t. with lithium hydroxide (7 mg, 0.15 mmol) in a mixture of MeOH (3 ml), THF (1 ml) and water (2 ml). After 72 hours the reaction mixture is diluted with ether (200 ml) and washed with three portions of water (100 ml). The combined aqueous layers are acidified to pH=2 with 1M hydrochloric acid and extracted with two portions of ethyl acetate (200 ml). The ethyl acetate extracts are dried over magnesium sulfate, filtered and concentrated in vacuo to give the title compound as a white foam. FAB-MS m/e 498 (M+H)⁺.

Example 74

Coupling of N-(3,5-dimethylbenzoyl)-N-methyl-(D)-phenylalanine |derived from the corresponding methylester described in example 78 by hydrolysis with lithium hydroxide in methanol/water: $|a|_D=+88°$ (c=1.0, ethanol)| with (D,L)-(2-pyridyl)alanine methyl ester hydrochloride (prepared according to example 54 according to the general method A according to Scheme II) according to example 1 followed by preparative HPLC separation of the 2 diastereomeric esters and hydrolysis of the methyl ester moieties according to example 12 gives N-(3,5-dimethylbenzoyl)-N-methyl-(D)-phenylalanyl-(D)-(2-pyridyl)-alanine, FAB-MS m/e 460 (M+H)⁺, and N-(3,5-dimethylbenzoyl)-N-methyl-(D)-phenylalanyl-(L)-(2-pyridyl)alanine; FAB-MS m/e 460 (M+H)⁺.

Example 75

Coupling of N-(3,5-dimethylbenzoyl)-N-methyl-(D)-phenylalanine (derived from the corresponding methylester described in example 78 by hydrolysis with lithium hydroxide in methanol/water: $|a|_D=+88°$ (c=1.0, ethanol)) with (D,L)-(4-phenylphenyl)alanine methyl ester hydrochloride (prepared from commercially available 4-phenylbenzyl chloride according to general method A according to Scheme II) according to example 1 followed by hydrolysis of the methyl ester moiety according to example 12 gives N-(3,5-dimethylbenzoyl)-N-methyl-(D)-phenylalanyl-(D,L)-(4-phenylphenyl)alanine as a mixture of 2 diastereomers; FAB-MS m/e 533 (M-H)⁻.

Example 76

Coupling of N-(3,5-dimethylbenzoyl)-N-methyl-(D)-phenylalanine (derived from the corresponding methylester described in example 78 by hydrolysis with lithium hydroxide in methanol/water: $|a|_D=+88°$ (c=1.0, ethanol)) with (D,L)-(4-quinolinyl)alanine ethyl ester hydrochloride (prepared as described in example 58 according to general method B according to Scheme III) according to example 1 followed by hydrolysis of the ethyl ester moiety according to example 12 gives N-(3,5-dimethylbenzoyl)-N-methyl-(D)-phenylalanyl-(D,L)-(4-quinolinyl)alanine as a mixture of 2 diastereomers; FAB-MS m/e 508 (M-H)⁻.

Example 77

Coupling of N-(3,5-dimethylbenzoyl)-N-methyl-(D)-phenylalanine (derived from the corresponding methylester described in example 78 by hydrolysis with lithium hydroxide in methanol/water: $|a|_D=+88°$ (c=1.0, ethanol)) with methyl 3-(3-indolyl)-2-hydroxypropionate (prepared from methyl 3-indolepyruvate by sodium borohydride reduction) according to example 1 followed by hydrolysis of the methyl ester moiety according to example 12 gives N-(3,5-dimethylbenzoyl)-N-methyl-(D)-phenylalanine-1-carboxy-2-(3-indolyl) ethyl ester as a mixture of 2 diastereomers; FAB-MS m/e 499 (M+H)⁺.

Example 78

5-(R)-|N-(3,5-Dimethylbenzoyl)-N-methyl|amino-2-(R)-(3-indolyl)methyl-4-oxo-6-phenylhexanoic acid A stirred solution of N-BOC-N-methyl-(D)-phenylalanine (3 g, 10.5 mmol) in methylenchoride (25 ml) is treated at 0° C. with slight excess of diazomethane in ether (25 ml). The reaction mixture is stirred at 0° C. and concentrated in vacuo to give N-BOC-N-methyl-(D)-phenylalanine methyl ester as a colorless oil. The above crude material is dissolved in a mixture of trifluoroacetic acid (8 ml) and ethanedithiol (2 ml) and stirred under nitrogen at r.t. for 1 hour. A 4M solution of hydrogen chloride in dioxane (3.6 ml) is added. The hydrochloride is precipitated by addition of ether (400 ml) and hexane (300 ml), filtered and washed with ether to give N-methyl-(D)-phenylalanine methyl ester hydrochloride (2.4 g) as a white powder. A solution of the above N-methyl-(D)-phenylalanine methyl ester hydrochloride (2.4 g, 10 mmol) and, 5-dimethylbenzoic acid (1.8 g, 11 mmol) in DMF (15 ml) at 0° C. is treated with 1-(3-dimethylaminopropyl)-3-ethylcarbodiimide (2.2 ml, 11 mmol). The reaction mixture is slowly warmed to r.t. and stirring continued overnight. The homogeneous mixture is diluted with ethyl acetate (500 ml) and washed with three portions of water (200 ml). The organic layer is dried over magnesium sulfate, filtered and concentrated in vacuo. The crude material is chromatographed on silica with ethyl acetate/hexane 1:2 to give N-(3,5-dimethylbenzoyl)-N-methyl-(D)-phenylalanine methyl ester as a colorless oil. $[a]_D = +111°$ (c=0.94, ethanol).

A cooled (–70° C.) solution of dimethyl methylphosphonate (800 mg, 6.4 mmol) in dry THF (15 ml) under nitrogen is treated with a 1.5M solution of buthyllithium in hexane (4.2 ml, 6.3 mmol). Stirring is continued at –70° C. for 30 minutes. A solution of the above N-(3,5-dimethylbenzoyl)-N-methyl-(D)-phenylalanine methyl ester (850 mg, 2.6 mmol) in dry THF (5 ml) is added dropwise. The colorless reaction mixture is stirred at –70° C. for another 2 hours. The reaction is quenched by addition of 1 ml acetic acid, diluted with ethyl acetate (400 ml) and washed with three portions of water (300 ml). The organic layer is dried over magnesium sulfate, filtered and concentrated in vacuo. The crude material is chromatographed on silica with ethyl acetate to give dimethyl 3-(R)-[N-(3,5-dimethylbenzoyl)-N-methyl|amino-2-oxo-4-phenyl-1-butylphosphonate as a colorless oil. $[a]_D = +145°$ (c=0.99, ethanol).

To a cooled (0° C.) suspension of sodium hydride (20 mg 60% in oil, 0.5 mmol) in dry THF (1 ml) under nitrogen atmosphere a solution of dimethyl 3-(R)-|N-(3,5-dimethylbenzoyl)-N-methyl|amino-2-oxo-4-phenyl-1-butylphosphonate (200 mg, 0.5 mmol) in dry THF (0.5 ml) is added dropwise. Stirring is continued for 30 minutes. A solution of benzyl indole-3-pyruvate (140 mg, 0.5 mmol; prepared from commercially available indole-3-pyruvic acid and benzyl bromide) in 0.5 ml dry THF is added dropwise. The reaction mixture is slowly warmed to r.t. and stirring continued overnight. The yellow reaction mixture is diluted with ethyl acetate (100 ml) and washed with three portions of water (70 ml). The organic layer is dried over magnesium sulfate, filtered and concentrated in vacuo. The crude material is chromatographed on silica with ethyl acetate to give a E/Z mixture of products (105 mg). This material is hydrogenolized at 5 atm hydrogen pressure in ethanol at 50°–60° C. in the presence of Wilkinson's catalyst (tris (triphenylphosphin)-rhodium(I) chloride). Chromatography on silica with ethyl acetate/hexane 1:2 gives benzyl 5-(R)-|N-(3,5-dimethylbenzoyl)-N-methyl|amino-2-(R,S)-(3-indolyl)methyl-4-oxo-6-phenylhexanoate as a 2:3 mixture of diastereomers. Separation of the diastereomers by preparative HPLC (silica, hexane/isopropanol 30:1) followed by hydrogenolytic removal (Pd/C, 1 atm hydrogen) of the benzylester moiety gives 5-(R)-|N-(3,5-dimethylbenzoyl)-N-methyl|amino-2-(R)-(3-indolyl)methyl-4-oxo-6-phenylhexanoic acid, de>98% and ee>92% (HPLC, chiralcel OD). FAB-MS m/e 497 (M+H)$^+$, and 5-(R)-|N-(3,5-Dimethylbenzoyl)-N-methyl|amino-2-(S)-(3-indolyl) methyl-4-oxo-6-phenylhexanoic acid, de>98% and ee>92% (HPLC, chiralcel OD), FAB-MS m/e 497 (M+H)$^+$.

Example 79

4-|N-(3,5-Dimethylbenzol)-N-methyl|amino-2-(3-indolyl)methyl-5-phenylpentanoic acid To a suspension of sodium hydride (9 mg, 0.22 mmol) in THF (1 ml) is added a solution of methyl 3-(3-indolyl)-2-(dimethylphosphono)propionate (80 mg, 0.169 mmol) in THF (0.7 ml) under nitrogen atmosphere and the mixture is stirred at 0° C. for 30 min. To the mixture is added a solution of 2-(R)-|N-(3,5-dimethylbenzoyl)-N-methyl|amino-3-phenyl-1-propanal (50 mg, 0.169 mmol) in THF (0.3 ml) and the whole is stirred at r.t. overnight. The reaction mixture is diluted with water and extracted with ethyl acetate. The organic layer is dried over magnesium sulfate and concentrated in vacuo. The residue is chromatographed on silica gel with ethyl acetate/hexane (1:2) to give methyl 4-|N-(3,5-dimethylbenzoyl)-N-methyl|amino-2-(3-indolylmethyl-5-phenylpent-2-enoate as a white foam. A solution of methyl 4-|N-(3,5-dimethylbenzoyl)-N-methyl| amino-2-(3-indolylmethyl-5-phenylpent-2-enoate (40 mg, 0.08 mmol) in methanol (2 ml) is hydrogenated over palladium carbon (5 mg) under hydrogen atmosphere at r.t. for 24 hrs. The catalyst is filtered off and the filtrate is concentrated in vacuo. The residue is chromatographed on silica gel with ethyl acetate/hexane (1:2) to give methyl 4-|N(3,5-dimethylbenzoyl)-N-methyl|amino-2-(3-indolyl)methyl-5-phenyl-pentanoate. Hydrolysis of methyl 4-|N(3,5-dimethylbenzoyl)-N-methyl|amino-2-(3-indolyl)methyl-5-phenyl-pentanoate according to example 1 gives 4-|N(3,5-dimethylbenzoyl)-N-methyl|amino-2-(3-indolyl)methyl-5-phenyl-pentanoic acid as a mixture of isomers; FAB-MS m/e 467 (M–H)$^-$.

The starting material can be manufactured e.g. as follows: Synthesis of 2-(R)-|N-(3,5-dimethylbenzoyl)-N-methyl| amino-3-phenyl-1-propanal To a solution of N-(3,5-dimethylbenzoyl)-N-methyl-(D)-phenylalanine methyl ester (prepared according to example 78) (895 mg, 2.75 mmol) in THF (15 ml) is added L-selectride (11 ml, 11 mmol) at 0° C. and the reaction mixture is stirred at the same temperature overnight. The mixture is diluted with diethyl ether, washed with water, dried over magnesium sulfate, and concentrated in vacuo. The residue is chromatographed on silica gel (ethyl acetate) to give 2-(R)-|N-(3,5-dimethylbenzoyl)-N-methyl|amino-3-phenyl-1-propanol.

To a stirred solution of dimethylsulfoxide (0.12 ml) in methylene chloride (4 ml) under nitrogen atmosphere is added oxalyl chloride (0.132 ml, 1.52 mmol) at –35° C. and the mixture is stirred for 30 min. To the mixture is added a solution of 2-(R)-|N-(3,5-dimethylbenzoyl)-N-methyl| amino-3-phenyl-1-propanol (410 mg, 1.38 mmol) in methylene chloride (4 ml) and stirring is continued at –35° C. for 30 min, then triethylamine (0.7 ml, 5 mmol) is added at –35° C. The reaction mixture is warmed up to r.t., diluted with water (10 ml) and extracted with methylene chloride (10 ml×3). The organic layer is dired over magnesium sulfate and concentrated in vacuo to give 2-(R)-|N-(3,5-dimethylbenzoyl)-N-methyl|amino-3-phenyl-1-propanal as a yellow oil.

Synthesis of methyl 3-(3-indolyl)-2-(dimethylphosphono) propionate

To a stirred solution of indole (5.6 g, 47.8 mmol) in acetonitrile (130 ml) is added Eschenmoser's salt (10 g, 54 mmol) under nitrogen atmosphere and the mixture is stirred for 30 min. The mixture is concentrated in vacuo and the residue is diluted with 1M sodium hydroxide solution and extracted with methylene chloride. The organic layer is dried over sodium carbonate and concentrated in vacuo to give 3-(dimethylaminomethyl)indole as a brown oil. To a solution of 3-(dimethylaminomethyl)indole in methylene chloride (200 ml) is dropped methyl iodide (5 ml, 80 mmol). The mixture is stirred at r.t. for 6 hrs. and concentrated in vacuo to give (3-indolylmethyl)trimethylammonium iodide as a brown foam. To a cooled (0° C.) suspension of sodium hydroxide (1.5 g, 37 mmol) in DMF (100 ml) is added trimethyl phosphonoacetate (6.7 ml, 41 mmol) and the mixture is stirred at 0° C. for 30 min. To the mixture is added (3-indolylmethyl)trimethylammonium iodide and the whole is stirred at r.t. overnight. The mixture is diluted with water and extracted with ethyl acetate. The organic layer is dried over magnesium sulfate and concentrated in vacuo. The residue is chromatographed on silica gel with ethyl acetate to give methyl 3-(3-indolyl)-2-(dimethylphosphono) propionate a a brown oil.

To a suspension of sodium hydride (9 mg, 0.22 mmol) in THF (1 ml) is added a solution of methyl 3-(3indolyl)-2-(dimethylphosphono)propionate (80 mg, 0.25 mmol) in THF (0.7 ml) at 0  C. under nitrogen atmosphere and the mixture is stirred at 0° C. for 30 min. To the mixture is added a solution of 2-(R)-|N-(3,5-dimethylbenzoyl)-N-methyl| amino-3-phenyl-1-propanal (50 mg, 0.169 mmol) in THF (0.3 ml) and the whole is stirred at r.t. overnight. The reaction mixture is diluted with water and extracted with ethyl acetate. The organic layer is dried over magnesium sulfate and concentrated in vacuo. The residue is chromatographed on silica gel with ethyl acetate/hexane (1:2) to give methyl as a white foam. A solution of 4-|N-(3,5-dimethylbenzoyl)-N-methyl|amino-2-(3-indolylmethyl)-5-phenyl-pent-2-enoate (40 mg, 0.08 mmol) in methanol (2 ml) is hydrogenated over palladium carbon (5 mg) under nitrogen atmosphere at r.t for 24 hrs. The catalyst is filtered off and the filtrate is concentrated in vacuo. The residue is chromatographed on silica gel with ethyl acetate/hexane (1:2) to give methyl 4-|N-(3,5-dimethylbenzoyl)-N-methyl| amino-2-(3-indolylmethyl)-5-phenyl-pentanoate. Hydrolysis of methyl 4-[N-(3,5-dimethylbenzoyl)-N-methyl]amino-2-(3-indolylmethyl)-5-phenyl-pentanoate according to example 1 gives 4-[-N-(3,5-dimethylbenzoyl)-N-methyl| amino-2-(3-indolylmethyl)-2-phenyl-pentanoic Example 80

A Wittig-Horner reaction according to example 78 between dimethyl 3-|N-(3,5-dimethylbenzoyl)-N-methyl| amino-2-oxo-4-phenyl-1-butylphosphonate (prepared according to example 78) and methyl 1-naphthyl pyruvate followed by catalytic hydrogenation of the double bond in the presence of Wilkinson's catalyst according to example 78 and hydrolysis of the methyl ester moiety according to example 12 gives 5-|N-(3,5-dimethylbenzoyl)-N-methyl| amino-2-(1-naphthyl)methyl-4-oxo-6-phenylhexanoic acid as a mixture of isomers; FAB-MS m/e 506 (M−H)⁻.

The starting material can be manufactured e.g. as follows:
Synthesis of methyl 1-naphthyl pyruvate Sodium (677 mg, 29.4 mmol) is dissolved in ethanol (48 ml). To the solution are added 1-naphthylacetonitrile (5.07 g, 30.3 mmol), then after 20 min. diethyl oxalate (4.1 ml, 30.3 mmol) at r.t. and the mixture is stirred at r.t. for 2 hrs. and refluxed for 1 hour. After cooling to r.t. acetic acid (2 ml) is added. The mixture is diluted with water and extracted with ethyl acetate. The organic layer is dried over magnesium sulfate and evaporated in vacuo to give 3-cyano-3-(1-napththyl)pyruvate. A mixture of 3-cyano-3-(1-naphthyl) pyruvate (6.56 g, 24.6 mmol) and 30% sulfric acid (400 ml) is heated at 100° C. for 2 hrs. After cooling, the mixture is extracted with ethyl acetate. The organic layer is dried over magnesium sulfate and evaporated on vacuo to give 3-(1-naphthyl)pyruvic acid. To a solution of 3-(1-naphthyl) pyruvic acid(1.86 g, 8.7 mmol) in diethyl ether (20 ml) is added diazomethane diethyl ether solution (25 ml). The mixture is concentrated in vacuo and the residue is chromatographed on silica gel with hexane and ethyl acetate (3:2) to give methyl 3-(1-naphthyl)pyruvate.

Example 81

Reductive alkylation of (L)-tryptophan methyl ester hydrochloride with 2-(R)-|N-(3,5-dimethylbenzoyl)-N-methyl|amino-3-phenyl-1-propanal (prepared as described in example 79) in methanol in the presence of sodium cyanoborohydride according to example 14 followed by hydrolysis of the methyl ester moiety according to example 12 gives N-{2-(R)-|N-(3,5-dimethylbenzoyl)-N-methyl| amino-3-phenyl-prop-1-yl}-(L)-tryptophan; FAB-MS m/e 484 (M+H)⁺.

Example 82

100 mg of benzyl-5-(R)-|N-(3,5-dimethylbenzoyl)-N-methyl|amino-2-(R)-(3-indolyl)-methyl-4-oxo-6-(4-biphenylyl)hexanoate which is obtained as described in example 84 is dissolved in 750 μl of tetrahydrofuran and 36 μl of water. At 0° C. under atmosphere of nitrogen 4 mg of sodiumborohydride are added. The mixture is stirred at 0° C. for one hour and at ambient temperature for an additional hour. Then 280 μl of saturated aqueous ammonium chloride solution is added, stirred for 30 minutes, and the mixture extracted with ether. Evaporation of the ether phase results in a crude product which is purified by flash chromatography on silca gel with a mixture of ethylacetate and hexane (2:1) as eluent. 15 mg of the resulting lactone are subsequently treated with 2 mg of lithium hydroxide in a mixture of 500 μl of methanol and 250 μl of water for 12 hours at ambient temperature. Evaporation of the solvent gives a quantitaive yield of lithium 5-(R)-|N-(3,5-dimethylbenzoyl)-N-methyl| amino-2-(R)-(3-indolyl)methyl-4-hydroxy-6-(4-biphenylyl) hexanoate.

Example 83

A Wittig-Horner reaction according to example 78 between dimethyl 3-[N-(3,5-dimethylbenzoyl)-N-methyl| amino-2-oxo-4-(2-thienyl)-1-butylphosphonate |from N-(3, 5-dimethylbenzoyl)-N-methyl-(D,L)-(2-thienyl)alanine methyl ester prepared as described in example 52) as described in example 78| and methyl 3-indole pyruvate followed by catalytic hydrogenation of the double bond in the presence of Wilkinson's catalyst according to example 78 and hydrolysis of the methyl ester moiety according to example 12 gives 5-|N-(3,5-dimethylbenzoyl)-N-methyl| amino-2-(3-indolyl)methyl-4-oxo-6-(2-thienyl)hexanoic acid as a mixture of isomers; FAB-MS m/e 501 (M−H)⁻.

Example 84

A Wittig-Horner reaction according to example 78 between dimethyl 3-(R)-|N-(3,5-dimethylbenzoyl)-N- methyl|amino-2-oxo-4-(4-phenylphenyl)-1-butylphosphonate |from N-(3,5-dimethylbenzoyl)-N-methyl-(D)-(4-phenyl-phenyl)alanine methyl ester (prepared as described in example 55) as described in example 78| and benzyl 3-indolepyruvate followed by catalytic hydrogenation of the double bond in the presence of Wilkinson's catalyst as described in example 78, preparative HPLC separation of the 2 diastereomers and hydrogenolysis of the benzyl ester moiety according to example 78 gives 5-(R)-|N-(3,5-dimethylbenzoyl)-N-methyl|amino-2-(R)-(3-indolyl)methyl-4-oxo-6-(4-phenylphenyl)hexanoic acid; FAB-MS m/e 573 (M+H)$^+$, and 5-(R)-|N-(3,5-dimethylbenzoyl)-N-methyl|amino-2-(S)-(3-indolyl)methyl-4-oxo-6-(4-phenylphenyl)hexanoic acid; FAB-MS m/e 573 (M+H)$^+$.

Example 85

Coupling of N-(3,5-dimethylbenzoyl)-N-methyl-(D,L)-3-phenyl-3-(4-phenylphenyl)alanine (prepared according example 108) with (L)-tryptophan methyl ester hydrochloride according to example 12 followed by hydrolysis of the methyl ester moiety according to example 1 gives N-(3,5-dimethylbenzoyl)-N-methyl-(D,L)-3-phenyl-3-(4-phenylphenyl)-alanyl-(L)-tryptophan as a mixture of 2 diastereomers; FAB-MS m/e 650 (M+H)$^+$.

Example 86

Coupling of N-(3,5-dimethylbenzoyl)-N-methyl-(D,L)-(5-dibenzosuberyl)alanine (prepared from commercially available 5-chlorodibenzosuberane according to the general method B according to Scheme III) with (L)-tryptophan methyl ester hydrochloride according to example 1 followed by hydrolysis of the methyl ester moiety according to example 12 gives N-(3,5-dimethylbenzoyl)-N-methyl-(D,L)-(5-dibenzosuberyl)-alanyl-(L)-tryptophan as a mixture of 2 diastereomers; FAB-MS m/e 600 (M+H)$^+$.

Example 87

N-(5-methyl-2-thienylcarbonyl)-N-methyl-(D)-phenylalanyl-(L)-tryptophan

Coupling of N-methyl-(D)-phenylalanyl-(L)-tryptophan methyl ester hydrochloride with 5-methyl-thienyl-2-carboxylic acid according to example 1 followed by hydrolysis of the methyl ester according to example 12 results in N-(5-methyl-2-thienylcarbonyl)-N-methyl-(D)-phenylalanyl-(L)-tryptophan; FAB-MS m/e (M−H)$^−$.

Example 88

N-(3,5-Dimethylbenzoyl)-1,2,3,4-tetrahydro-3-isoquinolinecarbonyl-(L)-tryptophan A solution of methyl 1,2,3,4-tetrahydro-3-isoquinolinecarboxylate hydrochloride (2.0 g, 9 mmol) and 3,5-dimethylbenzoic acid (1.6 g, 10 mmol) in DMF (15 ml) is treated with 1-(3-dimethylaminopropyl)-3-ethylcarbodiimide (1.9 ml, 10 mmol). The reaction mixture is slowly warmed to r.t. and stirring continued for 2 hours. The homogeneous mixture is diluted with ethyl acetate (500 ml) and washed with three portions of water (200 ml). The organic layer is dried over magnesium sulfate, filtered and concentrated in vacuo. The crude material is chromatographed on silica with ethyl acetate/hexane 1:3 to give methyl N-(3,5-dimethylbenzoyl)-1,2,3,4-tetrahydro-3-isoquinolinecarboxylate as a colorless oil. This material is hydrolized with 1M sodium hydroxide in THF to give N-(3,5-dimethylbenzoyl)-1,2,3,4-tetrahydro-3-isoquinolinecarboxylic acid as a white solid.

To a stirred solution of N-(3,5-dimethylbenzoyl)-1,2,3,4-tetrahydro-3-isoquinolinecarboxylic acid (350 mg, 1.1 mmol) in dry DMF (2 ml) is added (L)-tryptophan methyl ester hydrochloride (290 mg, 1.1 mmol) and hydroxybenztriazole (180 mg, 1.3 mmol). The mixture is cooled to 0° and 1-(3-dimethylaminopropyl)-3-ethylcarbodiimide (0.25 ml, 1.3 mmol) is added dropwise. The reaction mixture is slowly warmed to r.t. and stirring continued overnight. The homogeneous mixture is diluted with ethyl acetate (100 ml) and washed with three portions of water (70 ml). The organic layer is dried over magnesium sulfate, filtered and concentrated in vacuo. The crude material is chromatographed on silica with ethyl acetate/hexane 1:1 to give a mixture of 2 diastereomeric N-(3,5-dimethylbenzoyl)-1,2,3,4-tetrahydro-3-isoquinolinecarbonyl-(L)-tryptophan methyl ester as a white foam.

The above material is hydrolized at 0° with 1M sodium hydroxide in THF. The reaction mixture is diluted with ether and washed with three portions of water. The combined aqueous layers are acidified to pH=2 with 1M hydrochloric acid and extracted with two portions of ethyl acetate. The ethyl acetate extracts are dried over magnesium sulfate, filtered and concentrated in vacuo to give the title compound as a white foam; mp 119°–126° C. FAB-MS m/e 496 (M+H)$^+$.

Example 89

A Wittig-Horner reaction according to example 78 between dimethyl N-(3,5-dimethylbenzoyl)-1,2,3,4-tetrahydro-3-isoquinolinecarbonylmethylphosphonate |from methyl N-(3,5-dimethylbenzoyl)-1,2,3,4-tetrahydro-3-isoquinolinecarboxylate (prepared according to example 88) as described in example 78| and methyl 3-indolepyruvate followed by catalytic hydrogenation of the double bond in the presence of Wilkinson's catalyst according to example 78 and hydrolysis of the methyl ester moiety according to example 12 gives 3-|N-(3,5-dimethylbenzoyl)-1,2,3,4-tetrahydro-3-isoquinolinecarbonyl|-2-(3-indolyl)methyl-propionic acid as a mixture of isomers; FAB-MS m/e 495 (M+H)$^+$.

Example 90

Coupling of N-(3,5-dimethylbenzoyl)-1,2,3,4-tetrahydro-3-isoquinolinecarboxylic acid (prepared according to example 88) with (L)-(1-naphthyl)alanine methyl ester hydrochloride followed by hydrolysis of the methyl ester moiety gives N-(3,5-dimethylbenzoyl)-1,2,3,4-tetrahydro-3-isoquinolinecarbonyl-(L)-1-naphthylalanine as a mixture of 2 diastereomers; FAB-MS m/e 507 (M+H)$^+$.

Example 91

Coupling of N-(3,5-dimethylbenzoyl)-N-methyl-(D,L)-3-|4-(3-thienyl)-phenyl|alanine (prepared from 4-(3-thienyl) benzyl bromide according to the general method B shown in Scheme III) with (L)-tryptophan methyl ester hydrochloride followed by separation of two diastereoisomers by HPLC gives (D,L)-isomer and (L,L)-isomer. Hydrolysis of (D,L)-isomer according to example 1 affords N-(3,5-dimethylbenzoyl)-N-methyl-(D)-3-|4-(3-thienyl)phenyl| alanyl-(L)-tryptophan; FAB-MS m/e 578 (M−H)$^+$.

The starting material can be manufactured e.g. as follows: Synthesis of 4-(3-thienyl)benzyl bromide A solution of 4-bromotoluene (0.9 ml, 7.3 mmol) in THF (3 ml) is added to dried magnesium turnings (0.815 g, 33.5 atoms) under nitrogen atmosphere. After the exothermic reaction initiates, a solution of 4-bromotoluene (3.16 ml, 25.7 mmol) in THF (3 ml) is dropped to the reaction mixture. The stirring is continued for 10 min. The mixture is dropped to a suspension of 3-bromothiophene (2.8 ml, 29.9 mmol) and |1,2-bis(diphenylphosphino)-ethane|nickel (II) chloride (0.72 g, 1.4 mmol) in diethyl ether (50 ml), which has been stirred for 10 min. The reaction mixture is cooled and quenched with 1N hydrochloric acid and extracted with ether. The organic layer is washed with saturated sodium bicarbonate and brine, dried over magnesium sulfate and concentrated in vacuo. The residue is recrystallized from ethanol to give 4-(3-thienyl)toluene.

To a solution of 4-(3-thienyl)toluene (3.56 g, 20.5 mmol) in carbon tetrachloride (100 ml) is added N-bromosuccinimide (3.64 g, 20.5 mol) and benzoyl peroxide (80 mg, 3.3 mmol). The reaction mixture is heated at reflux for 24 hrs. and concentrated in vacuo. The reaction mixture is recrystallized from ethanol to afford 4-(3-thienyl) benzyl bromide.

Example 92

Hydrolysis of (L,L)-isomer obtained in example 91 according to example 1 gives N-(3,5-dimethylbenzoyl)-N-methyl-(L)-3-|4-(3-thienyl)-phenyl|alanyl-(L)-tryptophan; FAB-MS m/e 578 (M–H)$^+$.

Example 93

Coupling of N-(3,5-dimethylbenzoyl)-N-methyl-(D,L)-3-|4-(2-thienyl)-phenyl|alanine |prepared from 4-(2-thienyl) benzyl bromide (prepared as described in example 91) according to the general method B shown in Scheme III] with (L)-tryptophan methyl ester hydrochloride according to example 1 followed by separation of two diastereoisomers by HPLC gives (D,L)-isomer and (L,L)-isomer. Hydrolysis of (D,L)-isomer according to example 1 affords N-(3,5-dimethylbenzoyl)-N-methyl-(D)-3-|4-(2-thienyl)phenyl] alanyl-(L)-tryptophan; FAB-MS m/e 578 (M–H)$^+$.

The starting material can be manufactured e.g. as follows:

4-(2-Thienyl)benzyl bromide is prepared from 4-bromotoluene and 2-bromothiophene according to example 91.

Example 94

Hydrolysis of (L,L)-isomer obtained in example 93 according to example 1 gives N-(3,5-dimethylbenzoyl)-N-methyl-(L)-3-|4-(2-thienyl)-phenyl|alanyl-(L)-tryptophan; FAB-MS m/e 578 (M–H)$^+$.

Example 95

Coupling of N-(3,5-dimethylbenzoyl)-N-methyl-(D,L)-3-|4-(5-isoxazolyl)-phenyl|alanine (prepared from 4-(5-isoxazolyl)benzyl bromide according to the general method B shown in Scheme III) with (L)-tryptophan methyl ester hydrochloride according to example 12 followed by separation of two diastereoisomers by medium pressure column chromatography gives (D,L)-isomer and (L,L)-isomer. Hydrolysis of (D,L)-isomer according to example 1 affords N-(3,5-dimethylbenzoyl)-N-methyl-(D)-3-|4-(5-isoxazolyl) phenyl|alanyl-(L)-tryptophan; FAB-MS m/e 565 (M–H)$^+$.

The starting material can be manufactured e.g. as follows:

According to example 56, 4-(5-isoxazolyl)toluene |Lin et al. J. Org. Chem. 45, 4857 (1980)| is brominate to give 4-(5-isoxazolyl)benzyl bromide.

Example 96

Hydrolysis of (L,L)-isomer obtained in example 95 according to example 12 gives N-(3,5-dimethylbenzoyl)-N-methyl-(L)-3-|4-(5-isoxazolyl)-phenyl|alanyl-(L)-tryptophan; FAB-MS m/e 563 (M–H)$^+$.

Example 97

Hydrolysis of N-(3,5-dimethylbenzoyl)-(D,L)-3-|4-(5-isoxazoyl)phenyl|alanine ethyl ester (prepared according to example 56) according to example 1 and coupling with (L)-tryptophan methyl ester hydrochloride according to example 12, followed by hydrolysis of the methyl ester according to example 1 gives N-(3,5-dimethylbenzoyl)-(D,L)-3-|4-(5-isoxazolyl)phenyl|alanyl-(L)-tryptophan; FAB-MS m/e 549 (M–H)$^+$.

Example 98

Coupling of N-(3,5-dimethylbenzoyl)-N-methyl-(D,L)-3-(4-cyanophenyl)-alanine |prepared from 4-cyanobenzyl bromide (from 4-cyanotoluene as described in the procedure according to example 56) according to the general method B shown in Scheme III] with (L)-tryptophan methyl ester hydrochloride according to example 1 followed by separation of two diastereoisomers by medium pressure column chromatography gives (D,L)-isomer and (L,L)-isomer. Hydrolysis of (D,L)-isomer according to example 1 affords N-(3,5-dimethylbenzoyl)-N-methyl-(D)-3-(4-cyanophenyl) alanyl-(L)-tryptophan; FAB-MS m/e 521 (M–H)$^+$.

Example 99

Hydrolysis of (L,L)-isomer obtained in example 98 according to example 1 gives N-(3,5-dimethylbenzoyl)-N-methyl-(L)-3-(4-(cyanophenyl)alanyl-(L)-tryptophan; FAB-MS m/e 521 (M–H)$^+$.

Example 100

A solution of the methyl ester |(D,L)-isomer: obtained in example 98| (500 mg, 0.932 mmol) and tetrabutyltin azide (464 mg, 1.4 mmol) in toluene (50 ml) is refluxed for 20 h under nitrogen atmosphere. To the mixture are added methylene chloride (50 ml), methanol (30 ml), and ammonium hydroxide (1 ml). The whole is stirred at room temperature for 1 h, then concentrated in vacuo. The residue obtained is chromatographed on silica with hexane/ethyl acetate (1:4+ 0.5% acetic acid) to give the resulting tetrazole derivative. Hydrolysis of the compound obtained according to example 1 gives N-(3,5-dimethylbenzoyl)-N-methyl-(D)-3-|4-(5-tetrazolyl)phenyl|alanyl-(L)-tryptophan; FAB-MS m/e 564 (M–H)$^+$.

Example 101

According to the procedure described in example 100, the formation of tetrazole ring from the methyl ester |(L,L)-isomer: obtained in example 98| followed by hydrolysis of the methyl ester according to example 1 gives N-(3,5-dimethylbenzoyl)-N-methyl-(L)-3-|4-(5-tetrazolyl)phenyl| alanyl-(L)-tryptophan; FAB-MS m/e 564 (M–H)$^+$.

Example 102

Coupling of N-(3,5-dimethylbenzoyl)-N-methyl-(D,L)-3-|4-(3-isoxazolyl)-phenyl|alanine (prepared from 4-(3-isoxazolyl)benzyl bromide according to the general method B shown in Scheme III) with (L)-tryptophan methyl ester hydrochloride according to example 1 followed by separation of two diastereoisomers by medium pressure column chromatography gives (D,L)-isomer and (L,L)-isomer. Hydrolysis of (D,L)-isomer according to example 1 affords N-(3,5-dimethylbenzoyl)-N-methyl-(D)-3-|4-(3-isoxazolyl) phenyl|alanyl-(L)-tryptophan; FAB-MS m/e 565 (M–H)⁺.

The starting material can be manufactured e.g. as follows:

4-(3-Isoxazolyl)benzyl bromide is prepared from 4-(3-isoxazolyl toluene |prepared from p-tolualdehyde according to the procedure for the synthesis of 2-(3-isoxazolyl) mesitylene: L. D. Nunno et al., Tetrahedron, 43, 2181 (1987)| according to example 56.

Example 103

Hydrolysis of (L,L)-isomer obtained in example 102 according to example 1 gives N-(3,5-dimethylbenzoyl)-N-methyl-(L)-3-|4-(5-isoxazolyl)-phenyl|alanyl-(L)-tryptophan; FAB-MS m/e 565 (M–H)⁺.

Example 104

N-(3,5-Dimethylbenzoyl)-N-methyl-(D,L)-3-|4-(5-isoxazolyl)phenyl|alanine ethyl ester (obtained in example 95) is treated with 3 equivalents of lithium hydroxide to give N-(3,5-dimethylbenzoyl)-N-methyl-(D,L)-3-|4-(2-cyanoacetyl)phenyl|alanine. Coupling of the compound obtained above with (L)-tryptophan methyl ester hydrochloride according to example 1 followed by separation of two diastercoisomers by medium pressure column chromatography gives (D,L)-isomer |containing 20% of (L,L)-isomer| and (L,L)-isomer |containing 25% of (D,L)-isomer|. Hydrolysis of (D,L)-isomer according to example 1 affords N-(3,5-dimethylbenzoyl)-N-methyl-(D)-3-|4-(2-cyanoacetyl)phenyl|alanyl-(L)-tryptophan; FAB-MS m/e 563 (M–H)⁺.

Example 105

Hydrolysis of (L,L)-isomer obtained in example 104 according to example 1 gives N-(3,5-dimethylbenzoyl)-N-methyl-(L)-3-|4-(2-cyanoacetyl)phenyl|alanyl-(L)-tryptophan; FAB-MS m/e 563 (M–H)⁺.

Example 106

To a solution of (D)-3-(4-nitrophenyl)alanine monohydrate (4.56 g, 20 mmol) in MeOH (80 ml) under nitrogen atmosphere is slowly added thionyl chloride (24 ml, 320 mmol). The reaction mixture is heated at reflux overnight and concentrated in vacuo. The residue is taken up in ether, then filtered. The precipitates obtained are washed with several portions of ether and dried in vacuo to afford (D)-3-(nitrophenyl)alanine methyl ester hydrochloride.

To a cooled (0° C.) solution of the above ester (2.60 g, 10 mmol) and 3,5-dimethylbenzoic acid (1.95 g, 13 mmol) in DMF (60 ml) under nitrogen atmosphere is added 1-(3-dimethylaminopropyl)-3-ethyl-carbodiimide (2.38 ml, 13 mmol) with stirring. The reaction mixture is slowly warmed to room temperature and stirred for 3 days. The reaction mixture is diluted with ethyl acetate, and washed with 1N hydrochloric acid and with saturated sodium bicarbonate solution. The organic layer is dried over magnesium sulfate and concentrated in vacuo to give N-(3,5-dimethylbenzoyl) -(D)-3-(4-nitrophenyl)alanine methyl ester.

To a cooled (0° C.) solution of the above ester (2.5 g, 7.0 mmol) and methyl iodide (1.3 g, 21.0 mmol) in DMF (26 ml) is slowly added sodium hydride (60% in oil; 0.28 g, 7.0 mmol) with stirring. After 30 min, the reaction mixture is quenched with water and extracted with ethyl acetate. The organic layer is dried over magnesium sulfate and concentrated in vacuo to give N-(3,5-dimethylbenzoyl)-N-methyl-(D)-3-(4-nitrophenyl)alanine methyl ester.

The above ester is hydrolysed at room temperature with lithium hydroxide (323 ml, 7.7 mmol) in MeOH/water, 10:1 (55 ml). After 2 h, the reaction mixture is diluted with water and washed with ether. The aqueous layer is acidified with 1N hydrochloric acid and extracted with ethyl acetate. The organic layer is dried over magnesium sulfate and concentrated in vacuo to give N-(3,5-dimethylbenzoyl)-N-methyl-(D)-3-(4-nitrophenyl)alanine.

Coupling of the compound obtained above with (L)-tryptophan methyl ester hydrochloride according to example 1 affords N-(3,5-dimethylbenzoyl)-N-methyl-(D)-3-(4-nitrophenyl)-alanyl-(L)-tryptophan methyl ester. Hydrolysis of the above ester according to example 1 gives N-(3,5-dimethylbenzoyl)-N-methyl-(D)-3-(4-nitrophenyl)alanyl-(L)-tryptophan; FAB-MS m/e 541 (M–H)⁺.

Example 107

A solution of N-(3,5-dimethylbenzoyl)-N-methyl-(D)-3-(4-nitrophenyl)-alanyl-(L)-tryptophan (20 mg) obtained in example 106 in MeOH (1 ml) is hydrogenated over platinum oxide (1 mg) under 3.8 atm hydrogen pressure. After 1 h, catalyst is removed by filtration and the filtrate is concentrated in vacuo. The crude material is purified by preparative thin layer chromatography on silica with ethyl acetate/ MeOH/acetic acid, 90:10:1 to give N-(3,5-dimethylbenzoyl) -N-methyl-(D)-3-(4-aminophenyl)alanyl-(L)-tryptophan; FAB-MS m/e 511 (M–H)⁺.

Example 108

Coupling of N-(3,5-dimethylbenzoyl)-N-methyl-3-(4-biphenyl)3-phenyl-(D,L)-alanine (prepared from bromo-(4-biphenyl)-phenylmethane according to the general method B shown in Scheme III) with (L)-tryptophan methyl ester hydrochloride according to example 1 followed by separation of four diastereoisomers by medium pressure chromatography gives (R,D,L)-isomer, (S,D,L)-isomer (R,L,L)-isomer, and (S,L,L)-isomer. Hydrolysis of (R,D,L)-isomer according to example 1 affords (3R)-N-(3,5-dimethylbenzoyl)-N-methyl-3-(4-biphenyl)-3-phenyl-(D)-alanyl-(L)-tryptophan; FAB-MS m/e 648 (M–H)⁺.

The starting material can be manufactured as follows:
Synthesis of bromo-(4-biphenyl)-phenylmethane To a solution of dimethylsulfoxide (3.9 ml, 54.4 mmol) in methylene chloride (70 ml) under nitrogen atmosphere is added trifluoroacetic acid (5.7 ml, 40.8 mmol) with stirring at –70° C. After 10 min., 4-biphenylmethanol (5 g, 27.2 mmol) is added, and after being stirred for 30 min., triethylamine (30 ml, 218 mmol) is added. The reaction mixture is allowed to warm up to r.t., diluted with water, and extracted with methylene chloride. The organic layer is washed successively with 1N hydrochloric acid and saturated sodium bicarbonate, dried over magnesium sulfate and concentrated to give 4-biphenylmethanal. To a cold solution (0° C.) of 4-biphenylmethanal in THF (50 ml) under nitrogen atmosphere is slowly added 3M phenylmagnesium bromide solution in diethyl ether (5.3 ml, 15.7 mmol) with stirring. The reaction mixture is allowed to warm up to r.t. and the stirring is continued for 15 hrs. The mixture is diluted with water and extracted with diethyl ether. The organic layer is washed with saturated ammonium chloride, dried over magnesium chloride, and concentrated in vacuo. The residue is purified by flash column chromatography on silica gel with 15% diethyl ether in hexane to give (4-biphenyl)-phenylmethanol.

To a solution of (4-biphenyl)-phenylmethanol (0.737 g, 2.83 mmol) in methylene chloride (40 ml) under nitrogen atmosphere is added thionyl bromide (3.7 ml, 47.8 mmol) at r.t. with stirring. After 2 hrs., the reaction mixture is taken up into methylene chloride, and then washed with water. The organic layer is dried over sodium sulfate and concentrated in vacuo to give bromo-(4-biphenyl)-phenylmethane.

Example 109

Hydrolysis of (S,D,L)-isomer obtained in example 108 according to example 1 gives (3S)-N-(3,5-dimethylbenzoyl) -N-methyl-3-(4-biphenyl)-3-phenyl-(D)-alanyl-(L)-tryptophan; FAB-MS m/e 648 (M−H)⁺.

Example 110

Hydrolysis of (R,L,L)-isomer obtained in example 108 according to example 1 gives (3R)-N-(3,5-dimethylbenzoyl) -N-methyl-3-(4-biphenyl)-3-phenyl-(L)-alanyl-(L)-tryptophan; FAB-MS m/e 648 (M−H)⁺.

Example 111

Hydrolysis of (S,L,L)-isomer obtained in example 108 according to example 1 gives (3S)-N-(3,5-dimethylbenzoyl) -N-methyl-3-(4-biphenyl)-3-phenyl-(L)-alanyl-(L)-tryptophan; FAB-MS m/e 648 (M−H)⁺.

Example 112

To a stirred solution of 3-(4-biphenyl)alanine methyl ester hydrochloride (755 mg, 2.6 mmol) and di-t-butyl dicarbonate (680 mg, 3.1 mmol) in methylene chloride (10 ml) is dropped triethylamine (0.432 ml, 3.1 mmol) at 0° C. under nitrogen atmosphere. The reaction mixture is slowly warmed to room temperature and stirred for 2 h. The mixture is sucessively washed with 0.1N hydrochloric acid, saturated sodium bicarbonate, and brine, and dried over magnesium sulfate and concentrated in vacuo. The residue is chromatographed on silica with ethyl acetate/hexane (1:2) to give N-BOC-3-(4-biphenyl)alanine methyl ester as a yellow oil. A cooled (0° C.) solution of the compound obtained above (953 mg) and methyl iodide (0.486 ml, 7.8 mmol) in DMF (8 ml) is added 60% sodium hydride (104 mg, 2.6 mmol) under nitrogen atmosphere. The reaction mixture is slowly warmed up to room temperature and stirred for 2 days. The mixture is diluted with water and extracted with ethyl acetate (10 ml×2). The organic layer is washed with water (5 ml×2), saturated sodium chloride solution, and dried over magnesium sulfate, and concentrated in vacuo to give N-BOC-3-(4-biphenyl)alanine methyl ester. Hydrolysis of the above-obtained methyl ester (855 mg, 2.3 mmol) with lithium hydroxide hydrate (146 mg, 3.5 mmol) gives N-BOC-3-(4-biphenyl)alanine.

Coupling of N-BOC-3-(4-biphenyl)alanine (750 mg, 2.1 mmol) according to the general method B shown in Scheme III) with (L)-tryptophan methyl ester hydrochloride (642 mg, 2.5 mmol) in the presence of 1-hydroxybenzotriazole (340 mg, 2.5 mmol) and 1-(3-dimethylaminopropyl)-3-ethylcarbodiimide (462 μl, 2.5 mmol) affords N-BOC-N-methyl-3-(4-biphenyl)alanyl-(L)-tryptophan methyl ester (1.16 g, 95%). A stirred solution of N-BOC-N-methyl-3-(4-biphenyl)alanyl-(L)-tryptophan methyl ester (1.0 g, 1.8 mmol) in toluene (10 ml) is treated with Lawessons's reagent (364 mg, 0.9 mmol) at room temperature under nitrogen atmosphere overnight. The mixture is diluted with ethyl acetate and washed with water and brine, then dried over magnesium sulfate and concentrated in vacuo. The residue is chromatographed on silica with ethyl acetate/ hexane (1:2) to give a mixture of two diastereoisomers (590 mg, 57%) which are separated by HPLC (silica, hexane/ isopropanol 30:1) to give N-BOC-N-methyl-(D)-3-(4-biphenyl)thioalanyl-(L)-tryptophan methyl ester and N-BOC-N-methyl-(L)-3-(4-biphenyl)thioalanyl-(L)-tryptophan methyl ester.

A stirred solution of N-BOC-N-methyl-(D)-3-(4-biphenyl)thioalanyl-(L)-tryptophan methyl ester (145 mg, 0.25 mmol) and dithiothreitol (77 mg, 0.05 mmol) in 1,4-dioxane (0.64 ml) is added 4N hydrogen chloride in 1,4-dioxane (2.6 ml) at room temperature under nitrogen atmosphere. The mixture is stirred for 4 h, concentrated in vacuo, and washed with ether to give N-methyl-(D)-3-(4-biphenyl) thioalanyl-(L)-tryptophan methyl ester hydrochloride.

A stirred solution of N-methyl-(D)-3-(4-biphenyl) thioalanyl-(L)-tryptophan methyl ester hydrochloride (150 mg) is treated with 3,5-dimethylbenzoic acid (50 mg, 0.33 mmol), 1-hydroxybenzotriazole (45 mg, 0.33 mmol), and 1-(dimethylaminopropyl)-3-ethyl-carbodiimide (60μ, 0.33 mmol) in DMF (1 ml) at room temperature under nitrogen atmosphere overnight. The mixture is diluted with ethyl acetate and washed with sat. sodium bicarbonate solution and with water, then dried over magnesium sulfate and concentrated in vacuo. The residue is chromatographed on silica with ethyl acetate/hexane (1:2) to give N-(3,5-dimethylbenzoyl)-N-methyl-(D)-3-(4-biphenyl)thioalanyl-(L)-tryptophan methyl ester.

Hydrolysis of N-(3,5-dimethylbenzoyl)-N-methyl-(D)-3-(4-biphenyl)-thioalanyl-(L)-tryptophan methyl ester (40 mg, 0.066 mmol) with lithium hydroxide hydrate (4 mg, 0.099 mmol) affords N-(3,5-dimethylbenzoyl)-N-methyl-(D)-3-(4-biphenyl)-thioalanyl-(L)-tryptophan; FAB-MS m/e 590 (M−H)⁺.

Example 113

According to the procedure described in example 112, N-BOC-N-methyl-(L)-3-(4-biphenyl)thioalanyl-(L)-tryptophan methyl ester (obtained in example 112) is BOC-deprotected, N-3,5-dimethylbenzoylated, and hydrolysed according to example 1 to give N-(3,5-dimethylbenzoyl)-N-methyl-(L)-3-(4-biphenyl)-thioalanyl-(L)-tryptophan; FAB-MS m/e 590 (M−H)⁺.

Example 114

To a solution of (D)-tyrosine methyl ester hydrochloride (6.95 g, 30 mmol) and 3,5-dimethylbenzoic acid (4.73 g, 31.5 mmol) in DMF (15 ml) is slowly dropped 1-(3-dimethylaminopropyl)-3-ethyl-carbodiimide (5.46M solution) (5.77 ml, 31.5 mmol) at 0° C. under nitrogen atmosphere. The reaction mixture is allowed to stir at 0° C. for 1 h, then at room temperature overnight. The mixture is diluted with 250 ml of ice-water and extracted with ethyl acetate twice. The organic layer is dried over magnesium sulfate and concentrated in vacuo. The residue is chromatographed on silica with ethyl hexane/ethyl acetate (1:1) to give N-3,5-dimethylbenzoyl-tyrosine methyl ester.

To a solution of N-3,5-dimethylbenzoyl-tyrosine methyl ester (4.11 g, 12.6 mmol) and pyridine (5 ml) in methylene chloride (25 ml) is added triflic anhydride (2.2 ml, 13.2 mmol) at 0° C. under nitrogen atmosphere. After being stirred at room temperature for 4 h, the reaction mixture is washed with H₂O, 0.5N NaOH, H₂O, 1N HCl, and H₂O succesively. The organic layer is dried over magnesium sulfate and concentrated in vacuo. The residue is chromatographed on silica with ethyl hexane/ethyl acetate (2:1) to give N-3,5-dimethylbenzoyl-O-trifluoromethansulfonyl-tyrosine methyl ester.

To a suspension of N-3,5-dimethylbenzoyl-O-trifluoromethansulfonyl-tyrosine methyl ester (1.84 g, 4 mmol), furanboronic acid (0.90 g, 8 mmol) (prepared according to the literature procedure: W. Thompson, et al, J. Org. Chem., 1984, 49, 5237), potassium carbonate (0.83 g, 6 mmol), and toluene (50 ml) is added tetrakis (triphenylphosphine)palladium (0) (0.14 g, 0.12 mmol) under nitrogen atmosphere. The mixture is healed at 90° C. for 2 h, then diluted with ethyl acetate and washed with sat. NaHCO₃, H₂O, 10% citric acid, and H₂O, successively. The organic layer is dried over magnesium sulfate and concentrated in vacuo. The residue is chromatographed on silica with hexane/ethyl acetate (1:1) to give a N-3,5-dimethylbenzoyl-|4-(2-furyl)phenyl|alanine methyl ester.

Methyl iodide (0.55 ml, 8.82 mmol), then sodium hydride (oil free: 70.6 mg, 2.94 mmol) in DMF (3 ml) at 0° C. under nitrogen atmosphere. The reaction mixture is allowed to stir at 0° C. for 1 h, then at room temperature overnight. The mixture is diluted with H₂O and extracted with ethyl acetate twice. The organic layer is dried over magnesium sulfate and concentrated in vacuo. The residue is chromatographed on silica with hexane/ethyl acetate (1:1) to give N-3,5-dimethylbenzoyl-N-methyl-|4-(2-furyl)phenyl|alanine methyl ester which is hydrolysed with lithium hydroxide hydrate (118 mg, 2.82 mmol) to N-3,5-dimethylbenzoyl-N-methyl-|4-(2-furyl)phenyl|alanine.

To a solution of N-3,5-dimethylbenzoyl-N-methyl-|4-(2-furyl)phenyl|alanine (0.64 g, 1.7 mmol) in DMF are successively added tryptophan methyl ester hydrochloride (0.56 g, 2.2 mmol), 1-hydroxybenzotriazole (0.504 g, 3.73 mmol), and 1-(3-dimethylaminopropyl)-3-ethyl-carbodiimide (5.46M solution) (0.37 ml, 2.03 mmol) at 0° C. under nitrogen atmosphere. The reaction mixture is allowed to stir at 0° C. for 2 h, then at room temperature overnight. The mixture is diluted with ethyl acetate and washed with 10% citric acid twice. The organic layer is dried over magnesium sulfate and concentrated in vacuo. The residue is chromatographed on silica with hexane/ethyl acetate (1:1) to give N-3,5-dimethylbenzoyl-N-methyl-3-|4-(2-furyl)phenyl| alanyl-tryptophan methyl ester s a mixture of diastereoisomers which are separated by HPLC into (D,L)-isomer. Hydrolysis of (D,L)-isomer (102 mg, 0.18 mmol) with lithium hydroxide hydrate (7.8 mg, 0.185 mmol) gives N-(3,5-dimethylbenzoyl)-N-methyl-(D)-3-|4-(2-furyl) phenyl)-alanyl-(L)-tryptophan.

Example 115

Hydrolysis of (L,L)-isomer (20 mg, 0.035 mmol) obtained in example 114 with lithium hydroxide hydrate (1.52 mg, 0.036 mmol) gives N-(3,5-dimethylhenzoyl)-N-methyl-(L)-3-|4-(2-furyl)phenyl)-alanyl-(L)-tryptophan.

Example 116

To a suspension of sodium hydride (60% in oil: 0.82 g, 20.5 mmol) in dry DMF (4.5 ml) under nitrogen atmosphere is added imidazole (1.37 g, 20.1 mmol) with stirring at room temperature. After being stirred for 20 min. 4-bromobenzaldehyde dimethyl acetal (4.63 g, 20 mmol) and copper powder (0.13 g, 2.0 mmol) are added and the reaction mixture is stirred at 130° C. for 2 h, then at 150° C. for 2.5 h. The mixture is cooled to room temperature, diluted with chloroform and water. The solution is stirred for 1 h and filtered on Celite. The organic layer is separated, washed wit water, dried over sodium sulfate, and concentrated in vacuo. The residue is dissolved in 1N hydrochloric acid (20 ml) and stirred at room temperature for 4 h. The reaction mixture is diluted with 5N NaOH (4 ml), and extracted with ethyl acetate. The organic layer is washed with brine, dried over sodium sulfate, and concentrated in vacuo. The solid obtained is washed with hexane and dried in vacuo to give 4-(1-imidazolyl)benzaldehyde.

To a cooled (0° C.) solution of 4-(1-imidazolyl) benzaldehyde (1.41 g, 8.16 mol) and ethyl azidoacetate (10.6 g, 81.7 mmol) in MeOH (50 ml) under nitrogen atmosphere is added sodium methoxide (28 wt. % solution in MeOH, 13.2 ml, 65 mmol) dropwise. Stirring is continued for 1.5 h. Then, the reaction mixture is diluted with brine (100 ml) and extracted with three portions of ether. The organic layer is dried over magnesium sulfate and concentrated in vacuo to give methyl 2-azido-3-|4-(1-imidazolyl) phenyl|-2-propenate.

A solution of 2-azido-3-|4-(1-imidazolyl)phenyl|-2-propenate (0.56 g, 2.09 mmol) in acetic acid (2 ml) and MeOH (30 ml) is hydrogenated over platinum oxide (0.18 g) under 30 atm hydrogen pressure overnight. Catalyst is removed by filtration, and the filtrate is concentrated in vacuo. The crude residue is dissolved in methylene chloride and washed with two portions of sat. sodium bicarbonate solution. The organic layer is dried over sodium sulfate and concentrated in vacuo to give 3-|4-(1-imidazolyl)phenyl| alanyl methyl ester.

A solution of 3-|4-(1-imidazolyl)phenyl|alanyl methyl ester (0.69 g, 2.8 mmol) in 1N hydrochloric acid (2.7 ml) and water (1.8 ml) is added freshly distilled cyclopentadiene (0.50 ml, 6.1 mmol) and formaldehyde (37% an aqueous solution) (0.24 ml, 30 mmol) with vigorous stirring. After being stirred for 1 h at room temperature, the reaction mixture is washed with hexane, neutralised with sat. sodium bicarbonate solution, and extracted with methylene chloride. The organic layer is dried over magnesium sulfate and concentrated in vacuo to give a cycloadduct.

To a solution of the above crude material (0.39 g) in chloroform (5.7 ml) under nitrogen atmosphere is added trifluoroacetic acid (5.7 ml) and triethylsilane (0.55 ml, 3.42 mmol) with stirring at room temperature. The mixture is stirred for 20 h, then concentrated under reduced pressure. The crude product is dissolved in 1N hyrochloric acid and washed with hexane/ether, 1:1. The aqueous layer is neutralised with sat. sodium bicarbonat solution, and extracted with methylene chloride. The organic layer is dried over magnesium sulfate and concentrated in vacuo to give 3-|4-(1-imidazolyl)phenyl|-N-methyl-alanyl methyl ester.

To a cooled (0° C.) solution of 3-|4-(1-imidazolyl)phenyl|-N-methyl-alanyl methyl ester (0.28 g) and 3,5-dimethylbenzoic acid (0.175 g, 1.17 mmol) in methylene chloride (2.0 ml) under nitrogen atmosphere is added 1-(3-dimethylaminopropyl)-3-ethyl-carbodiimide (0.21 ml, 1.15 mmol) with stirring. After 30 min, the reaction mixture is slowly warmed to room temperature and further stirred overnight. The reaction mixture is diluted with ethyl acetate and washed with two portions of water and brine. The organic layer is dried over magnesium sulfate and concentrated in vacuo. The crude material is purified by column chromatography on silica with methylene chloride/MeOH, 30:1 to give N-(3,5-dimethylbenzoyl)-N-methyl-3-|4-(1-imidazolyl)-phenyl|-alanine methyl ester.

The above ester is hydrolyzed at room temperature with lithium hydroxide (19 mg, 0.45 mmol) in MeOH/THF/water, 2:2:1 (2.5 ml) overnight. The reaction mixture is acidified with 1N hydrochloric acid (0.45 ml), diluted with water, and extracted with two portions of ethyl acetate. The organic layer is dried over magnesium sulfate and concentrated in vacuo to give N-(3,5-dimethylbenzoyl)-N-methyl-3-|4-(1-imidazolyl)-phenyl|-alanine.

To a stirred solution of the above acid (60 mg, 0.16 mmol) in dry DMF (3 ml) under nitrogen atmosphere are added (L)-tryptophan methyl ester hydrochloride (61 mg, 0.24 mmol) and 1-hydroxybenzotriazole (38 mg, 0.28 mmol). The mixture is cooled to 0° C. and 1-(3-dimethylaminopropyl)-3-ethyl-carbodiimide (0.029 ml, 0.16 mmol) is added dropwise. After being stirred for 1 h, the reaction mixture is slowly warmed to room temperature and further stirred overnight. The mixture is diluted with ethyl acetate and washed with water and brine. The organic layer is dried over magnesium sulfate and concentrated in vacuo. The crude material purified by preparative thin layer chromatography with methylene chloride/MeOH, 9:1 to give N-(3,5-dimethylbenzoyl)-N-methyl-3-|4-(1-imidazolyl)-phenyl|-(D.L)-alanyl-(L)-tryptophan methyl ester. The above ester (0.1 g, 0.173 mmol) is hydrolysed at 0° C. with lithium hydroxide (13.5 mg, 0.32 mmol) in MeCOH/water, 5:1 (5.0 ml). After 2 h, the reaction mixture is slowly warmed to room temperature and further stirred for 1 h. The reaction mixture is acidified with 1N hydrochloric acid (0.35 ml), diluted with water, and extracted with ethyl acetate. The organic layer is dried over magnesium sulfate and concentrated in vacuo. The residue is washed with ether and dried in vacuo to give N-(3,5-dimethylbenzoyl)-N-methyl-3-|4-(1-imidazolyl)-phenyl|-(D.L)-alanyl-(L)-tryptophan; FAB-MS m/e 564 (M-H)$^+$.

Example 117

A solution of N-(3,5-dimethylbenzoyl)-N-methyl-(D)-tyrosine methyl ester (253 mg, 0.74 mmol) (prepared from (D)-tyrosine following the procedure described in example 55), Ph$_3$Bi(OAc)$_2$ |triphenylbismuth diacetate| (895 mg, 1.6 mmol) (prepared according to the literature procedure; H. Brunner, U. Obermann, and P. Winner, *Organometallics* 1989, 8, 821–826), and Cu powder (43 mg, 0.68 mmol) in methylene chloride (15 ml) is stirred at room temperature under nitrogen atmosphere overnight. This reaction mixture is concentrated in vacuo and the crude material is chromatographed on silica with hexane/ethylacetate (3:1) to give N-(3,5-dimethylbenzoyl)-N-methyl-O-phenyl-(D)-tyrosine methyl ester as a colorless oil. Hydrolysis of the methyl ester obtained above (294 mg, 0.70 mol) by lithium hydroxide hydrate (31 mg, 0.74 mol) gives a corresponding acid.

To a solution of the acid obtained above (215 mg, 0.53 mmol) in DMF are successively added tryptophan methyl ester hydrochloride (177 mg, 0.70 mmol), 1-hydroxybenzotriazole (160 mg, 1.2 mmol), and 1-(3-dimethylaminopropyl)-3-ethylcarbodiimide (5.46M solution) (0.12 ml, 0.66 mmol) at 0° C. under nitrogen atmosphere. The reaction mixture is allowed to stir at 0° C. for 2 h, then at room temperature overnight. The mixture is diluted with ethyl acetate and washed with 10% citric acid and 4% sodium bicarbonate. The organic layer is dried over magnesium sulfate and concentrated in vacuo. The residue is chromatographed on silica with hexane/ethyl acetate (2:1) to give a (phenoxyphenyl)alanyl-tryptophan methyl ester (325 mg, 98%)

Hydrolysis of the methyl ester (325 mg, 0.52 mmol) with lithium hydroxide hydrate (23 ml, 0.55 mmol) gives N-(3,5-dimethylbenzoyl)-N-methyl-(D)-3-(4-phenoxyphenyl)-alanyl-(L)-tryptophan.

Example 118

To a stirred solution of L-alanine t-butyl ester hydrochloride (1.03 g, 5.69 mmol), triethylamine (0.792 ml, 5.69 mmol) and magnesium sulfate (463 mg) in methylene chloride (11 ml) is added benzaldehyde (0.549 ml, 5.40 mmol) at room temperature under nitrogen atmosphere. The reaction mixture is stirred at room temperature for 17 hours, then diluted with water (10 ml), and brine, successively, and dried over magnesium sulfate and concentrated in vacuo to give N-(phenylmethylene)alanine t-butyl ester as a colorless oil.

To a solution of N-(phenylmethylene)alanine t-butyl ester (210 mg, 0.90 mmol), 4-(3-thienyl)phenylmethyl bromide (250 mg, 0.99 mmol), and pyridine (7 ml, 0.09 mmol) in methylene chloride (1.8 ml) are added potassium hydroxide (505 mg, 9.0 mmol) and potassium carbonate (1.24 g, 9.0 mmol). The mixture is stirred at room temperature for 2 days, then filtered and washed with methylene chloride. The filtrate and washings are concentrated in vacuo to give a crude 3-|4-(3-thienyl)phenyl|alanine as a yellow oil.

A solution of 3-|4-(3-thienyl)phenyl|alanine in methanol (2 ml) is slowly added to a solution of thionyl chloride (6.8 ml, 94 mmol) in methanol (5 ml) at -10° C. The mixture is slowly warmed to room temperature, then refluxed overnight. The reaction mixture is concentrated in vacuo, diluted with ethyl acetate (10 ml), and extracted with water (10 ml×3). The aqueous layer is made basic with sodium bicarbonate and extracted with ethyl acetate (10 ml×3). The organic layer is dried over magnesium sulfate and concentrated in vacuo to give a crude 3-|4-(3-thienyl)phenyl|-alanine methyl ester.

A stirred solution of 3-[4-(3-thienyl)phenyl|-alanine methyl ester (650 mg) and triethylamine (1.64 g, 11.8 mmol) in 1,4-dioxane (10 ml) is added 3,5-dimethylbenzoyl chloride (517 mg, 3.07 mmol) at room temperature. The mixture is stirred at room temperature overnight. The reaction mixture is diluted with ether and washed with 1N hydrochloric acid, sat. sodium bicarbonate and water. The organic layer is dried over magnesium sulfate and concentrated in vacuo. The residue is chromatographed on silica with ethyl acetate/ hexane (1:2) to give N-(3,5-dimethylbenzoyl)-2-methyl-3-|4-(3-thienyl)phenyl|alanine methyl ester.

To a cooled (0° C.) solution of N-(3,5-dimethylbenzoyl)-2-methyl-3-|4-(3-thienyl)phenyl|alanine methyl ester (200 mg, 0.49 mmol) and methyl iodide (0.122 ml, 1.96 mmol) in DMF (2 ml) is added 60% sodium hydride (39 mg, 0.98 mmol) under nitrogen atmosphere. The reaction mixture is slowly warmed to room temperature and stirred for 2 days. The mixture is diluted with water and extracted with ethyl acetate (10 ml×2). The organic layer is washed with (5 ml×2), dried over magnesium sulfate and concentrated in vacuo. The residue is chromatographed on silica with ethyl acetate/hexane (1:2) to give N-(3,5-dimethylbenzoyl)-N-ethyl-2-methyl-3-|4-(3-thienyl)phenyl|alanine methyl ester.

A stirred solution of N-(3,5-dimethylbenzoyl)-N-methyl-2-methyl-3-|4-(3-thienyl)phenyl|alanine methyl ester (100 mg, 0.245 mmol) and potassium hydroxide (40 mg, 0.72 mmol) in ethanol (5 ml) is refluxed overnight. The mixture is diluted with water and washed with ether. The aqueous layer is washed with brine, dried over magnesium sulfate, and concentrated in vacuo to give the corresponding crude N-(3,5-dimethylbenzoyl)-N-methyl-2-methyl-3-|4-(3-thienyl)phenyl|alanine To a solution of N-(3,5-dimethylbenzoyl)-N-methyl-2-methyl-3-|4-(3-thienyl)phenyl|alanine (135 mg, 0.33 mmol) in DMF are successively added tryptophan methyl ester hydrochloride (110 ml, 0.43 mmol), 1-Hydroxybenzotriazole (58 mg, 0.43 mmol), and 1-(3-dimethylaminopropyl)-3-ethylcarbodiimide (5.46M solution) 79μ, 0.43 mmol) at 0° C. under nitrogen atomosphere. The reaction mixture is allowed to stir at 0° C. for 2 h, then at room temperature overnight. The mixture is diluted with ethyl acetate and washed with 10% citric acid twice. The organic layer is dried over magnesium sulfate and concentrated in vacuo. The residue is chromatographed on silica with hexane/ethyl acetate (1:1) to give (D,L)-isomer (55 mg) and (L,L)-isomer (80 mg; including 15% of (D,L) -isomer) (total 67%) of 3-|4-(3-thienyl)phenyl|alanyl-tryptophan methyl ester. Hydrolysis of (D,L)-isomer (55 mg, 0.09 mmol) with lithium hydroxide hydrate (6 mg, 0.14 mmol) affords N-(3,5-Dimethylbenzoyl)-N-methyl-(D)-2-methyl-3-|4-(3-thienyl)phenyl)-alanyl-(L)-tryptophan FAB-MS m/e 592 (M–H)+.

Example 119

Hydrolysis of (L,L)-isomer (80 mg, 0.13 mmol) obtained in example 118 with lithium hydroxide hydrate (8 mg, 0.20 mmol) gives N-(3,5-Dimethylbenzoyl)-N-methyl-(L)-2-methyl-3-|4-(3-thienyl)phenyl)alanyl-(L)-tryptophan; FAB-MS m/e 594 (M–H)+.

Example 120

To a solution of 5-(4-methylphenyl)-isoxazole (17 g) and N-bromosuccinimide (19 g) in tetrachlormethane (500 ml) under nitrogen, bisbenzoyl peroxide (0.43 g) is added, and the mixture heated on reflux over night. The solvent is evaporated, and the residue purified by flash chromatography (silica gel, hexane/ethyl acetate 4:1) to give pure 5-(4-bromomethylphenyl)-isoxazole. NMR (CDCl$_3$, 400 MHz) δ |ppm| 8.32 (d, 1.8 Hz, 1H), 7.78 (d, 8.2 Hz, 2H), 7.51 (d, 8.2 Hz, 2H), 6.54 (d, 1.8 Hz, 1H), 4.52 (s, 2H).

5-(4-bromomethylphenyl)-isoxazole (700 mg) and N-diphenylmethylene-glycine ethyl ester (890 mg) are dissolved in dichloromethane (20 ml) and stirred vigorously with a solution of tetrabutylammonium hydrogensulfate in 2.5 molar aqueous sodium hydroxide, at room temperature, over night. The organic layer is then separated off and concentrated. The residue is partitioned between ether and water, the etherphase washed with water and brine, dried over magnesium sulfate and evaporated to give crude N-diphenylmethylene-3-|4-(5-isoxazolyl)-phenyl|-alanine ethyl ester, which is used for the next step without further purification.

Crude N-diphenylmethylene-3-|4-(5-isoxazolyl)-phenyl| -alanine ethyl ester (280 mg) was treated with p-toluenesulfonic acid monohydrate (100 mg) in acetonitrile (35 ml) and water (3,5 ml) at ambient temperature for 3.5 hours. After concentration the residue is extracted with ether and 1N sodium hydroxide, washed with brine, dried concentrated to give crude 3-|4-(5-isoxazolyl)-phenyl|-alanine ethyl ester, which is used for the next step without further purification.

Crude 3-|4-(5-isoxazolyl)-phenyl|-alanine ethyl ester (660 mg) is dissolved in chloroform (6.6 ml), stirred vigorously with 2N aqueous sodium carbonate (1,4 ml), and after cooling to 10° C., 3,5-dimethylbenzoylchloride (0.7 ml) is added. Stirring is continued for 1 hour at 10° C. and for 2 hours at ambient temperature. Then extraction with dichloromethane/water, washing with 10% aqueous citric acid, and with brine, followed by evaporation gives the crude product. Flash chromatography on silica gel, hexane/ ethyl acetate (4:1), gives pure N-(3,5-dimethylbenzoyl)-3-|4-(5-isoxazolyl)-phenyl|-alanine ethyl ester. NMR (CDCl$_3$, 400 MHz) δ |ppm| 8.28 (d, 1.8 Hz, 1H), 7.72 (d, 8.2 Hz, 2H), 7.33 (s, 2H), 7.26 (d, 8.2 Hz, 2H), 7.15 (s, 1H), 6.65 (d, 7.3 Hz, 1H), 6.50 (d, 1.8 Hz, 1H), 5.09 (m, 1H), 4.24 (q, 7.1 Hz, 2H), 3.32 (m, 2H), 2.34 (s, 6H), 1.29 (t, 7.1 Hz, 3H).

A solution of N-(3,5-dimethylbenzoyl)-3-|4-(5-isoxazolyl)-phenyl|-alanine ethyl ester (3,8 g) and methyliodide (1.8 ml) in dry N,N-dimethylformamide (40 ml) is cooled in an ice bath and sodium hydride (60% in oil, 390 mg) is added in portions. The mixture is allowed to warm to room temperature during 5 hours, then poured into water, extracted with ethyl acetate, the organic phase washed with water, and with brine, dried and evaporated. Flash chromatography of the residue on silica gel (hexane/ethyl acetate 3:1) gives pure N-(3,5-dimethylbenzoyl)-N-methyl-3-|4-(5-isoxazolyl)-phenyl|-alanine ethyl ester. NMR (CDCl$_3$, 400 MHz) δ |ppm| 8.30 (d, broad, 1H), 7.75 (m, 2H), 7.41 (d, broad, 1H), 7.12 (d, broad, 1H), 6.97 (s, 0.5H), 6.93 (s, 0.5 H), 6.70 (s, 1H), 6.53 (d, broad, 1H), 6.36 (d, broad, 1H), 5.40 (m, 0.5H), 4.58 (m, 0.5H), 4.27 (m, 2H), 3.54 (m, 0.5H), 3.25 (m, 1H), 3.05 (m, 2H), 2.78 (s, 1.5H), 2.23 (s, 3H), 2.13 (s, 3H), 1.27 (m, 3H).

N-(3,5-dimethylbenzoyl)-N-methyl-3-|4-(5-isoxazolyl)-phenyl|-alanine ethyl ester is treated with lithium hydroxide monohydrate (5 mg) in methanol (0.5 ml), tetrahydrofuran (0.25 ml), and water (0.25 ml) for 3 hours at room temperature. The mixture is then partitioned between water and ether, the water phase acidified with 1N hydrochloric acid, and subsequently extracted with ethyl acetate. The ethyl acetate phase is washed with brine, dried, and evaporated to give N-(3,5-dimethylbenzoyl)-N-methyl-3-|4-(5-isoxazolyl)-phenyl|-alanine. NMR (CDCl$_3$, 400 MHz) δ |ppm| 8.48 (s), 8.30 (s), 7.80 (m), 7.43 (m), 7.13 (m), 7.03 (s), 6.94 (s), 6.75 (s), 6.69 (s), 6.54 (s), 6.36 (s), 5.16 (m), 4.65 (m), 3.55 (m), 3.40 (m), 3.25 (m), 3.10 (m), 2.80 (s), 2.26 (s), 2.14 (s).

At 0° C., N-(3,5-dimethylbenzoyl)-N-methyl-3-|4-(5-isoxazolyl)-phenyl|-alanine (445 mg) is stirred in N,N-dimethylformamide (24 ml) together with (L)-tryptophane methyl ester hydrochloride (400 mg), hydroxybenztriazol (330 mg), and 1-(3-dimethylaminopropyl)-3-ethylcarbodiimide (0.32 ml) for 1 hour and at ambient temperature over night. After extraction with ethyl acetate and 10% aqueous citric acid the organic phase is washed with 4% aqueous sodium bicarbonate, and with brine, dried and evaporated. Flash chromatography on silica gel (hexane/ ethyl acetate 2:1) gives the product as a mixture of diastereoisomers. Separation by medium pressure chromatography on a silica gel column, using ether/dichloromethane (1:1) as solvent gives both |N-(3,5-dimethylbenzoyl)-N-methyl-3-|4-(5-isoxazolyl)-phenyl|-(D)-alanyl|-(L)-tryptophane methyl ester. NMR (CDCl$_3$, 400 MHz) δ |ppm| 8.60 (s), 8.30 (m), 7.70 (m), 7.55 (m), 7.30 (m), 7.10 (m), 6.90 (m), 6.50 (m), 5.85 (s), 5.43 (m), 4.90 (m), 4.33 (m), 3.75 (s), 3.70 (s), 3.35 (m), 3.15 (m), 2.85 (s), 2.57 (s), 2.35 (s), 2.20 (s), 1.93 (s), 1.85 (s).

|N-(3,5-dimethylbenzoyl)-N-methyl-3-|4-(5-isoxazolyl)-phenyl|-(D)-alanyl|-(L)-tryptophane methyl ester (50 mg) is treated with lithiumhydroxide monohydrate (3.8 mg) in methanol (1 ml), tetrahydrofurane (0.5 ml), and water (0.5 ml), at 0° C. for 1 hour, and at room temperature for 2 hours. The mixture is then partitioned between water and ether, the water phase acidified with 1N hydrochloric acid, and subsequently extracted with ethyl acetate. The ethyl acetate phase is washed with brine, dried, and evaporated to give |N-(3,5-dimethylbenzoyl)-N-methyl-3-|4-(5-isoxazolyl)-phenyl|-(D)-alanyl|-(L)-tryptophane. NMR (CDCl$_3$, 400 MHz) δ |ppm| 8.29 (s), 8.12 (s), 7.70 (m), 7.55 (m), 7.28 (m), 7.17 (m), 7.07 (m), 6.98 (m), 6.86 (m), 6.61 (s), 6.53 (s), 6.49 (s), 5.97 (s), 5.43 (m), 4.87 (m), 4.40 (m), 3.90 (m), 3.33 (m), 2.08 (m), 2.77 (s), 2.18 (s), 1.89 (s).

Example 121

Tablets, each containing 50 mg of active ingredient, for example N-(3,5-Dimethylbenzoyl)-N-methyl-(D)-phenylalanyl-(L)-tryptophan, can be prepared as follows:

Composition (for 10,000 tablets)

| Active ingredient | 500.0 g |
|---|---|
| Lactose | 500.0 g |
| Potato starch | 352.0 g |
| Gelatin | 8.0 g |
| Talc | 60.0 g |
| Magnesium stearate | 10.0 g |
| Silica (highly disperse) | 20.0 g |
| Ethanol | q.s. |

The active ingredient is mixed with the lactose and 292 g of potato starch, and the mixture is moistened using an alcoholic solution of the gelatin and granulated by means of a sieve. After drying, the remainder of the potato starch, the talc, the magnesium stearate and the highly disperse silica are admixed and the mixture is compressed to give tablets of weight 145.0 mg each and active ingredient content 50.0 mg which, if desired, can be provided with breaking notches for finer adjustment of the dose.

Example 122

Coated tablets, each containing 100 mg of active ingredient, for example N-(3,5-Dimethylbenzoyl)-N-methyl-(D)-phenylalanyl-(L)-tryptophan, can be prepared as follows:

Composition (for 1000 tablets)

| Active ingredient | 100.00 g |
|---|---|
| Lactose | 100.00 g |
| Corn starch | 70.00 g |
| Talc | 8.50 g |
| Calcium stearate | 1.50 g |
| Hydroxypropylmethylcellulose | 2.36 g |
| Shellac | 0.64 g |
| Water | q.s. |
| Dichloromethane | q.s. |

The active ingredient, the lactose and 40 g of the corn starch are mixed and moistened and granulated with a paste prepared from 15 g of corn starch and water (with warming). The granules are dried, and the remainder of the corn starch, the talc and the calcium stearate are added and mixed with the granules. The mixture is compressed to give tablets (weight: 280 mg) and these are coated with a solution of the hydroxypropylmethylcellulose and the shellac in dichloromethane (final weight of the coated tablet: 283 mg).

Example 123

Tablets and coated tablets containing another compound of the formula I or a pharmaceutically acceptable salt of a compound of the formula I, for example as in one of Examples 1 to 120, can also be prepared in an analogous manner to that described in Examples 121 and 122.

Pharmacological Experiments

Endothelin (ET) receptor binding assay

The binding affinity to the ET receptor of the compounds of the present invention is determined according to the method described below (published in Takai et. al (1992) Biochem. Biophys. Res. Commun. 184, 953–959). ET-1 and ET-3 are purchased from Peptide Institute Inc. (Osaka, Japan). [$^{125}$I]ET-1 and [$^{125}$I]ET-3 (~74 TBq/mmol each) are purchased from Amersham International (Bucks, U.K.).

The plasma membrane of porcine lung (2 µg of protein) is incubated at 37° C. for 1 hour with 30 pM [$^{125}$I]ET-1 or 10 pM [$^{125}$I]ET-3 in the absence or presence of various amounts of nonlabeled ligands in a total volume of 1 ml of 20 mM HEPES (pH 7.4), containing 145 mM NaCl, 5 mM KCl, 3 mM $MgCl_2$, 1 mM EGTA, 1 mg/ml bovine serum albumin, and 0.2 mg/ml bacitracin. After the incubation, unbound [$^{125}$I]ETs are separated by centrifugation at 20,000×g for 20 min at 4° C. followed by aspiration of the supernatant. The radioactivity in the membrane pellet is measured in Wallac-1470 Wizard autogamma counter (Pharmacia). Nonspecific binding is defined as membrane-associated radioactivity in the presence of saturating concentrations of ETs (100 nM). Nonspecific binding is subtracted from the total binding and the difference is defined as specific binding. Total binding is always less than 15% of the total radioactivity added.

The binding to the $ET_A$ receptor is determined with [$^{125}$I]ET-1 in the presence of 1 nM nonlabeled ET-3 and the binding to the $ET_B$ receptor with [$^{125}$I]ET-3 alone. By Scatchard analysis, the $ET_A$ receptor shows an apparant dissociation constant (Kd) of 44 pM and maximum binding sites (Bmax) of 342 fmol/mg protein, while the $ET_B$ receptor has a Kd of 8 pM and Bmax of 362 fmol/mg protein. From the inhibition curves for the binding of [$^{125}$I]ETs, the apparant binding affinity constant (Ki) of one of the test compounds (example 55) is calculated as a parameter of the affinity for the $ET_A$ and $ET_B$ receptors.

The following table shows the results of the binding assay as % inhibition of the specific $ET_A$ and $ET_B$ receptor binding by respectively $10^{-5}$M and $10^{-7}$M of the test compounds:

| | % Inhibition of the Binding to | | $K_i$ ($ET_A$) | $K_i$ ($ET_B$) |
|---|---|---|---|---|
| Example | $ET_A$-Receptor | $ET_B$-Receptor | [nM] | [nM] |
| 1 | 37 | 55 | | |
| 4 | 74 | 93 | | |
| 7 | 77 | 87 | | |
| 12 | 36 | 91 | | |
| 55 | 94 | 100 | 440 | 1 |
| 57 | 34 | 95 | | |
| 65 | 47 | 59 | | |
| 84 | 46 | 70 | | |
| 91 | 100 | 100 | 54 | 0.23 |
| 93 | | | 87 | 0.6 |
| 95 | 98 | 98 | 45 | 0.21 |

Contraction of porcine coronary artery

The contraction assay is performed according to the published method (S. Shetty et al. Biochem. Biophys. Res. Commun. 191, 459–464, 1993) described below:

Fresh porcine hearts are obtained from a local abattoir, immediately immersed in ice-cold lactated Ringer's solution and transported to the laboratory within 30 min. of slaughter. The left anterior descending coronary artery is excised and placed in the aerated physiological salt solution. The arterial preparations are cleared of adhering connective tissues and cut into rings 0.5–1 cm long.

Two stainless steel self-closure wires are inserted through each arterial ring and the arrangement individually suspended in a constant temperature water-jacketed 20 ml organ bath for isometric force recording. The baths are filled with the physiological salt solution at 37° C. and continuously aerated with 95% $O_2$ and 5% $CO_2$. One of the wires is attached to a glass rod inside the organ bath and the other attached to a force-displacement transducer (Grass FT-03) by means of a silk thread. The tissues are subjected to resting tensions of 4 g and equilibrated for 90 min in physiological salt solution before experimental procedures are initiated.

The endothelium is removed from the preparations by gently rubbing the intimal surface with a wooden applicator. The failure of both 1 µM acetylcholine to relax mesenteric rings contracted with 1 μM phenylephrine and of 0.1 μM substance P to relax coronary rings contracted with 3 μM PGF$_{2\alpha}$ demonstrated the effectiveness of the endothelium removal. Concentration-response curves for ET-3 in the absence (vehicle control) or in the presence of 10$^{-6}$M of the test compound are generated by cumulative additions to the organ bath. The effects of the compound (example 1) are assessed in vessels under resting tension.

Contraction of guinea pig trachea

Contraction assays are performed basically according to the published method (M. Takai et al. Biochem. Biophys. Res. Commun. 184, 953–959, 1992). The trachea which is isolated from male Hartley guinea pigs weighing 350–500 g, is cut into rings of approximately 2 mm length after removal of the adherent fat and connective tissues. The epithelium is removed mechanically from the rings. The preparations are placed in organ baths containing a Krebs-Henseleit or Tyrode solution at 37° C., pH 7.4 bubbled with 95% O$_2$ and 5% CO$_2$. Tension is measured isometrically via a force-displacement transducer (Nikhon Kohden, Tokyo, TB-612T) under an initial tension of 1 g. Concentration-response curves for ET-3 are obtained by its cumulative application. Inhibitory activities of given compounds are investigated by the addition of their DMSO solutions into the baths 10 to 40 min before the addition of ET-3. These activities are evaluated numerically by pA$_2$ values which are negative logarithms of compound concentrations inducing a shift of the ET-3 concentration-effective curves toward the 2-fold higher concentration range of ET-3. Contraction produced by 60 mM KCl or 10 μM carbachol is used as a reference standard.

| | compounds of: | | |
|---|---|---|---|
| Example 1[1] | Example 55[2] | Example 91 | Example 95 |
| pA$_2$:6.3 | 7.0 | 7.0 | 7.6 |

[1]The Krebs-Henseleit solution (113.0 mM NaCl, 4.8 mM KCl, 2.5 mM CaCl$_2$, 1.2 mM KH$_2$PO$_4$, 1.2 mM MgSO$_4$, 25.0 mM NaHCO$_3$ and 5.5 mM glucose) is used. As the reference standard, 60 mM KCl is used.
[2]The Tyrode solution (137.0 mM NaCl, 2.7 mM KCl, 1.8 mM CaCl$_2$, 0.3 mM NaH$_2$PO$_4$, 0.5 mM MgCl$_2$, 11.9 mM NaHCO$_3$ and 5.5 mM glucose) with 0.01 mM EDTA.2Na is used. As the reference standard, 10 μM carbachol is used.

We claim:

1. A compound of the formula I:

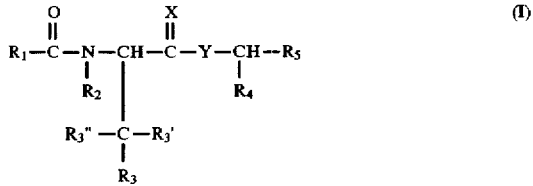

wherein
R$_1$ is phenyl substituted by halogen or C$_1$–C$_4$ alkyl;
R$_2$ is C$_1$–C$_4$ alkyl;
R$_3$ is phenyl, biphenylyl, naphthyl, thienyl, furyl, tetrazolyl, imidazolyl, pyridyl, quinolyl, pyridyl-phenyl, thienyl-phenyl, furyl-phenyl, imidazolyl-phenyl or isoxazolyl-phenyl, each of said radicals being unsubstituted or substituted by a substituent selected from the group consisting of C$_1$–C$_4$ alkyl, C$_1$–C$_4$ alkoxy, phenyl-lower alkoxy, halogen, CF$_3$, hydroxy, cyano, cyano-C$_2$-C$_5$ alkanoyl or nitro;
R$_3$' is hydrogen, phenyl or phenyl substituted by C$_1$–C$_4$ alkyl;
R$_3$" is hydrogen;
C(=X) is C(=O) or C(=S) and Y is NH or methylene; or
C(=X) is CHOH and Y is methylene;
R$_4$ is —(CH$_2$)$_s$—Ar' wherein s is the integer 1 and Ar' is phenyl, naphthyl, biphenylyl, indol-3-yl, 1-C$_1$–C$_4$-alkyl-indol-3-yl or quinolinyl, each of said radicals being unsubstituted or substituted by a substituent selected from the group consisting of C$_1$–C$_4$ alkyl, C$_1$–C$_4$ alkoxy, halogen, CF$_3$, hydroxy or nitro; and
R$_5$ is carboxy;
or a pharmaceutically acceptable salt thereof.

2. A compound according to claim 1 wherein R$_1$ represents 3,5-di-C$_1$–C$_4$-alkyl-phenyl;
R$_2$ is C$_1$–C$_4$-alkyl;
(i) R$_3$ is 4-biphenylyl, 4-(2-thienyl)-phenyl, 4-(3-thienyl)-phenyl, 4-(2-furyl)-phenyl, 4-(3-isoxazolyl)-phenyl, 4-(5-isoxazolyl)-phenyl, 4-(1-imidazolyl)-phenyl, or 4-(2-pyridyl)-phenyl;
R$_3$' is hydrogen or phenyl;
R$_3$" is hydrogen; or
(ii) R$_3$ is phenyl or phenyl substituted by cyano or cyano-C$_2$-C$_5$-alkanoyl;
R$_3$' and R$_3$" each are hydrogen;
C(=X) is (C=O) or C(=S);
Y is NH;
R$_4$ is —(CH$_2$)$_s$—Ar' wherein s is the integer 1; and Ar' is indol-3-yl; and
R$_5$ is carboxy;
or a pharmaceutically acceptable salt thereof.

3. A compound according to claim 1 wherein R$_1$ is phenyl substituted by halogen or C$_1$–C$_4$-alkyl;
R$_2$ is C$_1$–C$_4$-alkyl;
R$_3$ is phenyl being unsubstituted or substituted by halogen, C$_1$–C$_4$-alkoxy, hydroxy, or phenyl-C$_1$–C$_4$-alkoxy; biphenylyl; naphthyl; thienyl; thienyl being substituted by C$_1$–C$_4$-alkyl; pyridyl; pyridyl-phenyl; or thienyl-phenyl;
R$_3$' is hydrogen or phenyl; or
R$_3$" is hydrogen; or
C(=X) is C(=O); and Y is —NH— or —CH$_2$—; or
C(=X) is CHOH; and Y is methylene;
R$_4$ is —(CH$_2$)$_s$—Ar' wherein s is the integer 1; and Ar' is naphthyl, indolyl, or quinolinyl; and
R$_5$ is carboxy;
or a pharmaceutically acceptable salt thereof.

4. A compound according to claim 1 of formula I wherein R$_1$ represents 3,5-di-C$_1$–C$_4$-alkyl-phenyl, or 3,5-di-halophenyl;
R$_2$ is C$_1$–C$_4$-alkyl;
(i) R$_3$ is phenyl; and R$_3$' is phenyl; or (ii) R$_3$ is phenyl, 4-biphenylyl, or 4-(2-pyridyl)-phenyl; and R$_3$' is hydrogen; and
R$_3$" is hydrogen;
C(=X) is C(=O); Y is —NH—;
R$_4$ is —(CH$_2$)$_s$—Ar' wherein s is the integer 1; and Ar' is 3-indolyl; and
R$_5$ is a COOH;
or a pharmaceutically acceptable salt thereof.

5. A compound according to claim 1 wherein R$_1$ represents 3,5-di-C$_1$–C$_4$alkyl-phenyl;
R$_2$ is C$_1$–C$_2$-alkyl;
R$_3$ is 4-biphenylyl, 4-(2-thienyl)-phenyl, 4-(3-thienyl)-phenyl, 4-(2-furyl)-phenyl, 4-(3-isoxazolyl)-phenyl, 4-(5-isoxazolyl)-phenyl, or 4-(1-imidazolyl)-phenyl;
R$_3$' and R$_3$" each are hydrogen;
C(=X) is C(=O);
Y is NH;
R$_4$ is —(CH$_2$)$_s$—Ar' wherein s is the integer 1; and Ar' is 3-indolyl; and R₅ is a COOH;
or a pharmaceutically acceptable salt thereof.

6. A compound according to claim 1 wherein R₁ represents represents 3,5-dimethyl-phenyl;
R₂ is methyl;
R₃ is 4-biphenylyl, 4-(2-thienyl)-phenyl, 4-(3-thienyl)-phenyl, 4-(3-isoxazolyl)-phenyl, 4-(5-isoxazolyl)-phenyl, or 4-(1-imidazolyl)-phenyl;
R₃' and R₃" each are hydrogen;
C(=X) is C(=O);
Y is NH;
R₄ is —(CH₂)ₛ—Ar' wherein s is the integer 1; and Ar' is 3-indolyl; and
R₅ is a COOH;
or a pharmaceutically acceptable salt thereof.

7. A compound according to any one of claim 1 wherein Y is NH; having following stereochemistry:

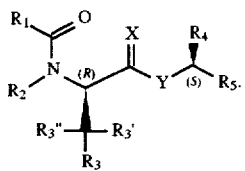

8. A compound according to claim 1 wherein Y is methylene; having following stereochemistry:

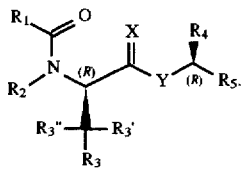

9. A compound according to claim 1 selected from the group consisting of:
N-(3,5-dimethylbenzoyl)-N-methyl-(D)-phenylalanyl-(L)-tryptophan;
N-(3,5-dimethylbenzoyl)-N-methyl-(D)-(4-phenylphenyl)alanyl-N-methyl-(L)-tryptophan;
N-(3,5-dichlorobenzoyl)-N-methyl-(D)-phenylalanyl-(L)-tryptophan;
N-(4-methoxybenzoyl)-N-methyl-(D)-phenylalanyl-(L)-tryptophan;
N-(3,5-dimethylbenzoyl)-N-methyl-(D)-(2-naphthyl)alanyl-(L)-tryptophan;
N-(3,5-dimethylbenzoyl)-N-methyl-(D)-(4-phenylphenyl)alanyl-(L)-tryptophan;
N-(3,5-dimethylbenzoyl)-N-methyl-(D,L)-(3-phenylphenyl)alanyl-(L)-tryptophan;
N-(3,5-dimethylbenzoyl)-N-methyl-(D,L)-(2-chlorophenyl)alanyl-(L)-tryptophan;
N-(3,5-dimethylbenzoyl)-N-methyl-(D,L)-|4-(2-pyridyl)phenyl|alanyl-(L)-tryptophan;
N-(3,5-dimethylbenzoyl)-N-methyl-(D)-tyrosyl-(L)-tryptophan;
N-(3,5-dimethylbenzoyl)-N-methyl-O-methyl-(D)-tyrosyl-(L)-tryptophan;
N-(3,5-dimethylbenzoyl)-N-methyl-O-benzyl-(D)-tyrosyl-(L)-tryptophan; and
N-(3,5-dimethylbenzoyl)-N-methyl-(D,L)-(2-thienyl)alanyl-(L)-tryptophan;
or a pharmaceutically acceptable salt thereof.

10. A compound according to claim 1 selected from the group consisting of:

N-(3,5-dimethylbenzoyl)-N-methyl-(D)-3-|4-(2-thienyl)phenyl|alanyl-(L)-tryptophan;
N-(3,5-dimethylbenzoyl)-N-methyl-(D)-3-|4-(3-isoxazolyl)phenyl|alanyl-(L)-tryptophan;
N-(3,5-dimethylbenzoyl)-N-methyl-(D)-3-|4-(2-furyl)phenyl|-alanyl-(L)-tryptophan; and
N-(3,5-dimethylbenzoyl)-N-methyl-3-|4-(1-imidazolyl)phenyl|-(D,L)-alanyl-(L)-tryptophan;
or a pharmaceutically acceptable salt thereof.

11. A compound according to claim 1 selected from the group consisting of:
N-(3,5-dimethylbenzoyl)-N-methyl-(D)-3-|4-(3-thienyl)phenyl|alanyl-(L)-tryptophan; and
N-(3,5-dimethylbenzoyl)-N-methyl-(D)-3-|4-(5-isoxazolyl)phenyl|alanyl-(L)-tryptophan;
or a pharmaceutically acceptable salt thereof.

12. A compound according to claim 1 selected from the group consisting of:
N-(3,5-dimethylbenzoyl)-N-methyl-(D)-3-(4-cyanophenyl)alanyl-(L)-tryptophan;
(3S)-N-(3,5-dimethylbenzoyl)-N-methyl-3-(4-biphenyl)-3-phenyl-(D)-alanyl-(L)-tryptophan;
N-(3,5-dimethylbenzoyl)-N-methyl-(D)-3-(4-biphenyl)-thioalanyl-(L)-tryptophan; and
N-(3,5-dimethylbenzoyl)-N-methyl-(D)-3-|4-(2-furyl)phenyl|-alanyl-(L)-tryptophan;
or a pharmaceutically acceptable salt thereof.

13. A pharmaceutical preparation comprising an effective amount of a compound according to claim 1, in free form or in form of a pharmaceutically acceptable salt, if appropriate in addition to customary pharmaceutical adjuncts.

14. A method of treating cerebral and coronary vasospasm, cerebral and coronary ischemia, subarachnoidal haemorrhage, various types of hypertension, pulmonary hypertention, cardiac failure, Raynand-syndrome, diabetes, atherosclerosis or restenosis due to denudation, asthma, renal failure, dialysis, glomerular injury, hepatic failure, stomach and duodenal ulcer, ulcus cruris, various brain dysfunctions, migraine, occular diseases, benign prostatic hyperplasma, or glaucoma in a subject in need of such treatment, which method comprises administering to such subject a therapeutically effective amount of a compound according to claim 1, in the free form or in form of a pharmaceutically acceptable salt.

15. A process for the manufacture of a compound of formula I according to claim 1 comprising a) reacting a compound of formula

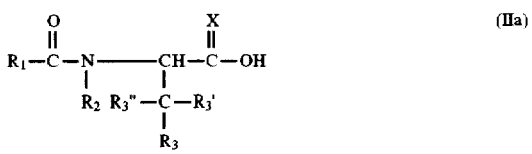

or a salt or a reactive acid derivative thereof with a compound of formula

free functional groups, with the exception of those participating in the reaction, being optionally in protected form, and any protecting groups present are removed, or b) reacting a compound of formula $$R_1-\overset{O}{\underset{\|}{C}}-OH \qquad (IIIa)$$

or a salt or reactive acid derivative thereof with a compound of formula $$H-N-\underset{\underset{\underset{R_3}{|}}{\underset{R_3''-C-R_3'}{|}}}{CH}-\overset{X}{\underset{\|}{C}}-Y-\underset{\underset{R_4}{|}}{CH}-R_5 \qquad (IIIb)$$

free functional groups, with the exception of those participating in the reaction, being optionally in protected form, and any protecting groups present are removed, and, if desired, converting a compound I obtainable according to the process or in another manner, in free form or in salt form, into another compound I, separating a mixture of isomers obtainable according to the process and isolating the desired isomer and/or converting a free compound I obtainable according to the process into a salt or converting a salt of a compound I obtainable according to the process into the free compound I or into another salt.

* * * * *